(12) United States Patent
Berezikov et al.

(10) Patent No.: US 10,583,149 B2
(45) Date of Patent: *Mar. 10, 2020

(54) MIRNA AND ITS DIAGNOSTIC AND THERAPEUTIC USES IN DISEASES OR CONDITIONS ASSOCIATED WITH MELANOMA, OR IN DISEASES OR CONDITIONS ASSOCIATED WITH ACTIVATED BRAF PATHWAY

(71) Applicants: INTERNA TECHNOLOGIES B.V., Nijmegen (NL); KONINKLIJKE NEDERLANDSE AKADEMIE VAN WETENSCHAPPEN, Amsterdam (NL)

(72) Inventors: Eugene Berezikov, Haren (NL); Jos Bernard Poell, Utrecht (NL); Willemijn Maria Gommans, Voorschoten (NL); Rick Jan van Haastert, Amersfoort (NL); Andreas Alphons F. L. van Puijenbroek, Boxtel (NL); Roeland Quirinus Jozef Schaapveld, Bussum (NL); Gregoire Pierre Andre Prevost, Antony (FR)

(73) Assignees: INTERA TECHNOLOGIES B.V., Nijmegen (NL); KONINKLIJKE NEDERLANDSE AKADEMIE VAN WETENSCHAPPEN, Amsterdam (NL)

( * ) Notice: Subject to any disclaimer, the term of this patent is extended or adjusted under 35 U.S.C. 154(b) by 14 days.

This patent is subject to a terminal disclaimer.

(21) Appl. No.: 15/625,945

(22) Filed: Jun. 16, 2017

(65) Prior Publication Data
US 2017/0304348 A1 Oct. 26, 2017

Related U.S. Application Data

(63) Continuation of application No. 13/734,414, filed on Jan. 4, 2013, now Pat. No. 9,682,095, which is a continuation of application No. PCT/NL2011/050476, filed on Jul. 1, 2011.

(60) Provisional application No. 61/361,787, filed on Jul. 6, 2010.

(30) Foreign Application Priority Data

Jul. 6, 2010 (EP) .................. 10168592

(51) Int. Cl.
*C12N 15/11* (2006.01)
*A61K 31/7088* (2006.01)
*C12N 15/113* (2010.01)
*C12Q 1/6809* (2018.01)

(52) U.S. Cl.
CPC ........ *A61K 31/7088* (2013.01); *C12N 15/111* (2013.01); *C12N 15/113* (2013.01); *C12N 15/1135* (2013.01); *C12Q 1/6809* (2013.01); *C12N 2310/113* (2013.01); *C12N 2310/141* (2013.01); *C12N 2320/10* (2013.01); *C12N 2320/31* (2013.01); *C12N 2330/10* (2013.01)

(58) Field of Classification Search
None
See application file for complete search history.

(56) References Cited

U.S. PATENT DOCUMENTS

| 2013/0197060 A1* | 8/2013 | Markel | ............... A61K 31/7105 514/44 A |
| 2014/0045924 A1* | 2/2014 | Yao | ...................... C12Q 1/6886 514/44 R |

FOREIGN PATENT DOCUMENTS

| WO | WO-2008088858 A2 * | 7/2008 | ........... C12N 15/113 |
| WO | WO-2009045356 A2 * | 4/2009 | ......... C12N 15/1136 |
| WO | WO-2011063455 A1 * | 6/2011 | ......... A61K 31/7105 |

OTHER PUBLICATIONS

Elson-Schwab et al, MicroRNA-200 Family Members Differentially Regulate Morphological Plasticity and Mode of Melanoma Cell Invasion, PLos One, Oct. 2010, v5, 10: 1-9 (Year: 2010).*
Schultz et al, MicroRNA let-7b targets important cell cycle molecules in malignant melanoma cells and interferes with anchorage independent growth, Cell Research, 2008, 18: 549-557 (Year: 2008).*
Felicetti et al , The Promyelocytic Leukemia Zinc Finger—MicroRNA-221/-222 Pathway Controls Melanoma Progression through Multiple Oncogenic Mechanisms, Cancer Research, 2008,68: 2745-2754 (Year: 2008).*

* cited by examiner

*Primary Examiner* — Ekaterina Poliakova-Georgantas
(74) *Attorney, Agent, or Firm* — Polsinelli PC; Christopher M. Cabral

(57) ABSTRACT

The invention relates to the diagnostic and therapeutic uses of a miRNA molecule, an equivalent or a source thereof in a disease and condition associated with melanoma or a disease or a condition associated with activated BRAF pathway.

16 Claims, 6 Drawing Sheets
Specification includes a Sequence Listing.

1 = Untreated
2 = BRAF siRNA
3 = mimic Ctrl
4 = miR-509-5p
5 = miR-129

MIRNA AND ITS DIAGNOSTIC AND THERAPEUTIC USES IN DISEASES OR CONDITIONS ASSOCIATED WITH MELANOMA, OR IN DISEASES OR CONDITIONS ASSOCIATED WITH ACTIVATED BRAF PATHWAY

FIELD OF THE INVENTION

The invention relates to the agnostic and therapeutic uses of a miRNA molecule, equivalent or source thereof in diseases and conditions associated with melanoma or in diseases or conditions associated with activated BRAF pathway.

SEQUENCE LISTING SUBMISSION VIA EFS-WEB

A computer readable text file, entitled "105811-5018-US-01-Revised-Seq-list" created on or about Jun. 16, 2017, with a file size of 64 KB contains the sequence listing for this application and is hereby incorporated by reference in its entirety.

BACKGROUND OF THE INVENTION

Melanoma is a common cancer of the skin resulting in high morbidity and mortality. Melanomas are malignancies of melanocytes, the specialized pigment cells of the skin, located at the basal layer of the epidermis and which originate from neural crest. Melanoma is one of the most aggressive cancer types in human. Melanoma accounts for only about 4% of skin cancer cases but for as many as 74% of all skin cancer deaths. In 2002, the WHO estimated 160,000 new cases of malignant melanoma worldwide and reported 41,000 deaths caused by this dreadful disease (Parkin D. M. et al., Cancer J. Clin. 55: 74, 2005). It is the cancer type with the highest increase in incidence: of all cancer in the United States, cutaneous melanoma ranks fifth in incidence among men and seventh among women and is the second leading cause of lost productive years. Recent estimates suggest a doubling of melanoma incidence every 10-20 years (Garbe C. and Leiter U., Clin. Dermatol. 27: 3, 2009). If melanoma can be diagnosed early, it can be cured by surgical excision and this is what occurs in appr. 80% of the cases. However, metastatic melanoma is refractory to current therapies and has a very poor prognosis with a median survival rate of 6 months. Both due to the high propensity to metastasize as well as resistance to available therapies, melanoma represents a great problem for oncology.

Several genes have been implicated in the development of melanoma. The most common tumor suppressor gene involved in melanoma is p16ink4a, encoded by the CDKN2A locus. The CDKN2A locus on human chromosome 9p21 encodes two proteins, p16ink4a and p14ARF, that mainly regulate cell cycle progression and cell survival via the pRb and p53 pathways, respectively. Loss of p16 is accomplished through deletion, mutation or promoter methylation. Mutations in the p14ARF tumor suppressor gene also play a role in melanoma, independent of the effect of the p16ink4a gene. The most commonly mutated oncogenes in melanoma are BRAF and N-RAS (Q61K/R), which are generally mutually exclusive. Interestingly, BRAF is mutated in ~70% of malignant melanomas, papillary thyroid cancer (36-53%), serous ovarian cancer (~30%) and colorectal cancer (5-22%), of which the majority is the V600E mutation. In addition, other BRAF mutations have also been detected in, serous ovarian cancer (30%) and lung cancer (3%) (Garnett M. J. et al., Cancer Cell, 2004). However, there are in at least 35 other amino acids within the BRAF protein that are targets for mutations in melanoma (Dhomen N. et al., Hematol. Oncol. Clin. North Am., 23: 529, 2009). The V600E mutation results in constitutively active BRAF and has been shown to act as an oncogene in melanocytes. As a consequence of the somatic mutations of BRAF and N-RAS, the RAS-RAF-MEK-ERK MAPK signal transduction pathway, that controls a variety of biological responses, including proliferation and survival, is constitutively active. The aberrant activation of this pathway results in increased proliferation and survival, but also represents an attractive molecular target for melanoma treatment. The importance of MAPK activation in melanoma was shown by inhibiting BRAF with RNAi and inhibiting BRAF or MEK with small molecule inhibitors (Hingorani S. R. et al., Cancer Res. 63: 5198, 2003, Karasarides M. et al., Oncogene 23: 6292, 2004). Such treatments block cell proliferation, survival, induce apoptosis and inhibit anchorage independent growth. Additional pathways that are aberrantly activated in melanoma are the PI3K/PTEN/Akt pathways. The phosphoinositide-3-kinase (PI3K) and mitogen-activated protein (MAP) kinase pathways are two key signaling cascades that have been found to play prominent roles in melanoma development. Therefore, members of the PI3K signaling pathway may also function as interesting targets for therapeutic intervention (Madhunapantula S. V. et al., Pigment Cell Melanoma Res. 22:400-19, 2009).

At present, enormous efforts are taken to unravel the molecular mechanisms that lead to changes in cellular processes and the resulting malignant behaviour of transformed melanocytes. One family of molecules involved in the genesis and progression of melanoma cells, the miRNAs, is currently attracting a lot of attention.

miRNAs are naturally occurring single-stranded, non-coding small RNA molecules that control gene expression by binding to complementary sequences in their target mRNAs, thereby inhibiting translation or inducing mRNA degradation. miRNAs have recently emerged as key regulators of gene expression during development and are frequently misexpressed in human disease states, in particular cancer.

Recently, several groups have taken a miRNA profiling approach, in which melanoma cell lines and/or melanoma samples were used to identify miRNA signatures and/or miRNAs that might play a regulatory role in melanoma. Some studies correlated expression of particular miRNAs with survival (Caramuta S. et al., J. Inv. Dermatol., 2010, Satzger I. et al., Int. J. Cancer 126: 2553, 2009 and Segura M. et al., Clin. Cancer Res. 16: 1577, 2010), mutational status (Caramuta S. et al.), progression (Mueller D. et al., J. Inv. Dermatol. 129: 1740, 2009, Segura M. et al., PNAS 106: 1814, 2009), chromosomal aberrations (Zhang L. et al., PNAS 103: 9136, 2006, Segura et al, 2009, Radhakrishnan A. et al., Mol. Vis. 15:2146, 2009) or merely described differential expression of specific miRNAs (Ma Z. et al., J. Mol. Diagn. 11:420, 2009, Stark M. et al., Plos One 5: e9685, 2010, Jukic D. et al., J. Transl. Med. 8: 27, 2010, Philippidou D. et al., Cancer Res. 70: 4163, 2010). Others identified signatures of miRNAs to distinghuis between different tissue types (Gaur A. et al., Cancer Res. 67: 2456, 2007, Blower P. et al., Mol. Cancer Ther. 6: 1483, 2007, Lu J. et al., Nature 435: 834, 2005) or different stages of development (Radhakrishnan A. et al., Caramuta S. et al.)

None of the above mentioned studies characterised melanoma-specific miRNAs in depth. The challenge is to relate specific miRNAs to their cellular function, and to unravel the impact of specific miRNAs in the formation and progression of malignant melanoma.

There is a limited amount of studies that have looked at specific miRNAs in melanoma. Some profiling studies ultimately resulted in focus on individual miRNAs and their function. Schultz et al. performed expression analysis of nevi and melanoma samples and focused on the Let-7 family, which was downregulated in melanoma. Overexpression of Let-7b in melanoma cells downregulated the expression of Cyclin D1, D3 and A and Cdk4, and consequently resulted in inhibition of cell cycle progression and anchorage independent growth (Schulz J. et al., Cell. Res. 18: 549, 2008). A similar profiling study comparing nevi and metastatic melanoma by Chen et al. resulted in identification of miR-193b downregulation in metastatic melanoma. They showed that reintroduction of miR-193b reduced proliferation and G1 arrest through regulation of Cyclin D1 (Chen J. et al., Am. J. Pathol. 176: 2520, 2010).

In uveal melanoma, miR-34a expression was found to be diminished. Reintroduction of miR-34a resulted in decreased proliferation and migration. c-Met as a target for miR-34a was suggested to be involved (Yan D. et al., Inv. Ophtamol. 50: 1559, 2009)

Other studies determined whether known melanoma specific genes are regulated by miRNAs. MITF, a transcription factor involved in melanocyte development was shown to be regulated by miR-340 (Goswami S. et al., J. Biol. Chem. 285: 20532, 2010), miR-137 (Bemis L. et al., Cancer Res. 68: 1362, 2008) as well as miR-182 (Segura M. et al., 2009). The latter also regulates FOXO3 and functional experiments showed that expression of miR-182 enhanced migration of melanoma cells and metastatic potential. Similarly, HOXB7, a transcription factor involved in melanoma, was found to be regulated by miR-196a. Inhibition of miR-196a resulted in HOXB7, its downstream target bFGF and ultimately an increased migration of a melanoma cell line. Additionally, 2 studies demonstrated that c-Kit, a receptor enhancing the tumorigenic potential of transformed melanocytes, is regulated by miR-221 and 222. Overexpression of miR-221/222 resulted in increased proliferation, migration and anchorage-independent growth in vitro and enhanced tumor growth in vivo (Igoucheva O. et al., Biochem. Biophys. Res. Com., 2009 and Felicetti F. et al., Cancer Res., 2008). Lastly, target prediction programs predicted that Integrin B3 may be regulated by Let-7a. Integrin β3 is known to play an important role in melanoma progression and invasion and its expression is increased during melanoma progression. Expression of Let-7a shows an inverse correlation in melanoma cell lines. Let-7a was able to regulate Integrin B3 and its inhibition resulted in increased migration (Muller D. et al., Oncogene 27: 6698, 2008)

Most of the studies that identified miRNAs involved with melanoma are profiling studies and/or were focussing on a specific miRNA. Most studies did not select a given miRNA based on a comparative functional analysis of a library comprising more than 1000 miRNAs. There is still a need for identifying miRNAs involved in melanoma using a functional screen, wherein the miRNA affects proliferation, apoptosis, survival, invasion and/or migration.

There is currently no effective known medicament that may be used for specifically preventing, treating, regressing, curing and/or delaying a disease or condition associated with melanoma or for diseases or conditions associated with activated BRAF pathway in a subject. The only standard treatments comprise chemotherapy, radiotherapy, surgery. Therefore, there is still a need for diagnostic markers for melanoma and for new treatments of disease or conditions associated with melanoma.

DESCRIPTION OF THE INVENTION

The invention encompasses several uses of a miRNA molecule, equivalent, mimic, isomiR or antagomir or source thereof as identified herein. The invention also encompasses each of the newly identified miRNA molecules equivalent, mimic, isomiR or antagomir per se.

In a first aspect, there is provided a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 molecule, an equivalent or a source thereof or a composition comprising said miRNA molecule, said equivalent or said source thereof for use as a medicament for preventing, treating, regressing, curing and/or delaying a disease or a condition associated with melanoma or for diseases or conditions associated with activated BRAF pathway.

MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA equivalent or a miRNA source is to be used for each of the identified miRNAs or miRNA equivalent or miRNA sources of this application: miRNA-10b, miRNA-18b, miRNA-96, miRNA-129, miRNA-128, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7, equivalents and sources thereof. Preferred mature (as identified in Table 3), seed (as identified in Table 5) or source sequences (as identified in Tables 2 (RNA precursor) or 4 (DNA encoding an RNA precursor)) or isomiR sequences (as identified in Table 6) of said miRNA molecule or equivalent thereof respectively are identified in corresponding tables. A DNA or RNA molecule encoding a RNA precursor of a miRNA molecule may be identified as a Hsa-miR-X (see for example Table 2 and Table 4) being a DNA or precursor of mir-X.

Within the whole text of the application unless otherwise indicated, a miRNA may also be named a miRNA molecule, a miR, or an equivalent thereof or a source or a precursor thereof. It is to be noted that some miRNA molecule are encoded by several precursors. For example miRNA-7 is encoded by Hsa-miR-7-1, Hsa-miR-7-2 or Hsa-miR-7-3. As another example, miRNA-128 is encoded by Hsa-miR-128-1 or Hsa-miR-128-2. As another example, miRNA-129 is encoded by Hsa-miR-129-1 or Hsa-miR-129-2. As another example, miRNA-16 is encoded by Hsa-miR-16-1 or Hsa-miR-16-2. As another example, miRNA-509 is encoded by Hsa-miR-509-1 or Hsa-miR-509-2 or Hsa-miR-509-3. As another example, miRNA-133a is encoded by Hsa-miR-133a-1 or Hsa-miR-133a-2. It is also possible that one precursor may lead to several mature miRNA molecule. An example is Hsa-miR-10b which may lead to miRNA-10b and miRNA-10*. Each sequence identified herein may be identified as being SEQ ID NO as used in the text of the application or as seq in the sequence listing.

MiRNA-221 and miRNA-222 are also referred to in the present invention. They are the only miRNA molecules of this invention whose expression is not to be upregulated/overexpressed/increased in order to be used in therapeutic applications for treatment of diseases or conditions associated with melanoma, or in diseases or conditions associated with activated BRAF pathway. In contrast, the endogenous expression of these two miRNA molecules needs to be downregulated/decreased to obtain a therapeutically desirable effect. This is preferably carried out as explained later herein using an antagomir. Therefore, in the invention when reference is made to these two miRNA molecules in a therapeutic use, one always refers to a use of an antagomir of a miRNA-221 or miRNA-222 molecule or of an equivalent of an antagomir of miRNA-221 or miRNA-222 molecule or a source of an antagomir of miRNA-221 or miRNA-222 molecule. Accordingly, when one refers to an antagomir one always refers to a use of an antagomir of a miRNA-221 or miRNA-222 molecule or an equivalent thereof or a source thereof. Each definition given herein concerning a given antagomir of a miRNA molecule also holds for other antagomir of distinct miRNA molecule all as defined herein.

In the context of the invention, a miRNA molecule or an equivalent or a mimic or an antogomir or an isomiR thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or a body fluid (i.e. endogenous human miRNA molecule). A human miRNA molecule may also be a human miRNA molecule derived from an endogenous human miRNA molecule by substitution, deletion and/or addition of a nucleotide. A miRNA molecule or an equivalent or a mimic or an antagomir thereof may be a single stranded or double stranded RNA molecule.

In an embodiment, a miRNA molecule or an equivalent, or a mimic or an antagomir thereof can be from 6 to 30 or 12 to 30 nucleotides in length, preferably 15 to 28 nucleotides in length, more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Preferably an antagomir of a miRNA molecule is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96 molecule or equivalent or mimic or isomiR thereof is represented by a sequence comprising SEQ ID NO: 103 or 104 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, a miRNA-96 molecule, equivalent or source thereof is intended to encompass a miRNA-96 or a mi-RNA-96* molecule, equivalent or source thereof, preferably a miRNA-96 molecule, equivalent or source thereof.

Accordingly a preferred miRNA-203 molecule or equivalent or mimic or isomiR thereof is represented by a sequence comprising SEQ ID NO: 111 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-10b molecule or equivalent or mimic or isomiR thereof is represented by a sequence comprising SEQ ID NO: 99 or 100 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-10b molecule, equivalent or source thereof is intended to encompass a miRNA-10b or a mi-RNA-10b* molecule, equivalent or source thereof.

Accordingly a preferred miRNA-18b molecule or equivalent or mimic or isomiR thereof is represented by a sequence comprising SEQ ID NO: 101 or 102 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-18b molecule, equivalent or source thereof is intended to encompass a miRNA-18b or a mi-RNA-18b* molecule, equivalent or source thereof.

Accordingly a preferred miRNA-129 molecule or equivalent or mimic or isomiR thereof is represented by a sequence comprising SEQ ID NO: 106, 107 or 108 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-129 molecule, equivalent or source thereof is intended to encompass a miRNA-129-5p, miRNA-129* or a miRNA-3p molecule, equivalent or source thereof. A miRNA-129-5p molecule, equivalent or source thereof is preferred.

Accordingly a preferred miRNA-128 molecule or equivalent or mimic or isomiR thereof is represented by a sequence comprising SEQ ID NO: 105 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-184 molecule or equivalent or mimic or isomiR thereof is represented by a sequence comprising SEQ ID NO: 109 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-190b molecule or equivalent or mimic or isomiR thereof is represented by a sequence comprising SEQ ID NO: 110 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157 molecule or equivalent or mimic or isomiR thereof is represented by a sequence comprising SEQ ID NO: 112 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-133a molecule or equivalent or mimic or isomiR thereof is represented by a sequence comprising SEQ ID NO: 116 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-200c molecule or equivalent or mimic or isomiR thereof is represented by a sequence comprising SEQ ID NO: 122 or 123 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-200c molecule, equivalent or source thereof is intended to encompass a miRNA-200c or a miRNA-200c* molecule, equivalent or source thereof. A miRNA-200c* molecule, equivalent or source thereof is preferred.

Accordingly a preferred miRNA-610 molecule or equivalent or mimic or isomiR thereof is represented by a sequence comprising SEQ ID NO: 129 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-182 molecule or equivalent or mimic or isomiR thereof is represented by a sequence comprising SEQ ID NO: 125 or 126 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-182 molecule, equivalent or source thereof is intended to encompass a miRNA-182 or a miRNA-182* molecule, equivalent or source thereof. A miRNA-182 molecule, equivalent or source thereof is preferred.

Accordingly a preferred miRNA-16 molecule or equivalent or mimic or isomiR thereof is represented by a sequence comprising SEQ ID NO: 113, 114 or 115 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-16 molecule, equivalent or source thereof is intended to encompass a miRNA-16, miRNA-16-1* or a miRNA-16-2* molecule, equivalent or source thereof. A miRNA-16 molecule, equivalent or source thereof is preferred.

Accordingly a preferred miRNA-95 molecule or equivalent or mimic or isomiR thereof is represented by a sequence comprising SEQ ID NO: 124 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-193a molecule or equivalent or mimic or isomiR thereof is represented by a sequence comprising SEQ ID NO: 127 or 128 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-193a molecule, equivalent or source thereof is intended to encompass a miRNA-193a-3p or a mi-RNA-193a-5p molecule, equivalent or source thereof. A miRNA-193a-3p molecule, equivalent or source thereof is preferred.

Accordingly a preferred miRNA-497 molecule or equivalent or mimic or isomiR thereof is represented by a sequence comprising SEQ ID NO: 120 or 121 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-497 molecule, equivalent or source thereof is intended to encompass a miRNA-497 or a mi-RNA-497* molecule, equivalent or source thereof. A miRNA-497 molecule, equivalent or source thereof.

Accordingly a preferred miRNA-509 molecule or equivalent or mimic or isomiR thereof is represented by a sequence comprising SEQ ID NO: 117, 118 or 119 or part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-509 molecule, equivalent or source thereof is intended to encompass a miRNA-509-3p, miRNA-509-5p or a miRNA-509-3-5p molecule, equivalent or source thereof. A miRNA-509-3p or miRNA-509-5p molecule, equivalent or source thereof is preferred.

Accordingly a preferred miRNA-7 molecule or equivalent or mimic or isomiR thereof is represented by a sequence comprising SEQ ID NO: 96, 97 or 98 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. In the context of the invention, miRNA-7 molecule, equivalent or source thereof is intended to encompass a miRNA-7, miRNA-7-1* or a miRNA-7-2* molecule, equivalent or source thereof. A miRNA-7 molecule, equivalent or source thereof is preferred.

For each of the miRNA molecule identified above, a part of a SEQ ID NO as identified may be at least 19 nucleotides of this SEQ ID NO.

In an embodiment, a miRNA molecule or equivalent or a mimic or an isomiR thereof comprises at least 6 of the 7 nucleotides present in the seed sequence of said miRNA molecule or equivalent or mimic or isomiR thereof (Table 5 shows preferred seed sequence of each of the miRNAs molecule identified herein). Preferably in this embodiment, a miRNA molecule or an equivalent or a mimic or isomiR thereof is from 6 to 30 nucleotides in length and more preferably comprises at least 6 of the 7 nucleotides present in the seed sequence of said miRNA molecule or equivalent thereof. Even more preferably a miRNA molecule or an equivalent or a mimic or isomiR thereof is from 15 to 28 nucleotides in length and more preferably comprises at least 6 of the 7 nucleotides present in the seed sequence, even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96 (i.e. miRNA-96 or miRNA-96*) molecule or equivalent or mimic or isomiR thereof comprises at least 6 of the 7 nucleotides present in the seed sequence identified as SEQ ID NO: 164 or 165 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-203 molecule or equivalent or mimic or isomiR thereof comprises at least 6 of the 7 nucleotides present in the seed sequence identified as SEQ ID NO: 172 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-10b (i.e. miRNA-10b or miRNA-10b*) molecule or equivalent or mimic or isomiR thereof comprises at least 6 of the 7 nucleotides present in the seed sequence identified as SEQ ID NO: 160 or 161 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-18b (i.e. miRNA-18b or miRNA-18b*) molecule or equivalent or mimic or isomiR thereof comprises at least 6 of the 7 nucleotides present in the seed sequence identified as SEQ ID NO: 162 or 163 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-129 (i.e. miRNA-129-5p, miRNA-129* or miRNA-129-3p) molecule or equivalent or mimic or isomiR thereof comprises at least 6 of the 7 nucleotides present in the seed sequence identified as SEQ ID NO: 167, 168 or 169 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-128 molecule or equivalent or mimic or isomiR thereof comprises at least 6 of the 7 nucleotides present in the seed sequence identified as SEQ ID NO: 166 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-184 molecule or equivalent or mimic or isomiR thereof comprises at least 6 of the 7 nucleotides present in the seed sequence identified as SEQ ID NO: 170 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-190b molecule or equivalent or mimic or isomiR thereof comprises at least 6 of the 7 nucleotides present in the seed sequence identified as SEQ ID NO: 171 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157 molecule or equivalent or mimic or isomiR thereof comprises at least 6 of the 7 nucleotides present in the seed sequence identified as SEQ ID NO: 173 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-133a molecule or equivalent or mimic or isomiR thereof comprises at least 6 of the 7 nucleotides present in the seed sequence identified as SEQ ID NO: 177 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-200c (i.e. miRNA-200c or miRNA-200c*) molecule or equivalent or mimic or isomiR thereof comprises at least 6 of the 7 nucleotides present in the seed sequence identified as SEQ ID NO: 183 or 184 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-610 molecule or equivalent or mimic or isomiR thereof comprises at least 6 of the 7 nucleotides present in the seed sequence identified as SEQ ID NO: 190 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-182 (i.e. miRNA-182 or miRNA-182*) molecule or equivalent or mimic or isomiR thereof comprises at least 6 of the 7 nucleotides present in the seed sequence identified as SEQ ID NO: 186 or 187 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-16 (i.e. miRNA-16, miRNA-16-1* or miRNA-16-2*) molecule or equivalent or mimic or isomiR thereof comprises at least 6 of the 7 nucleotides present in the seed sequence identified as SEQ ID NO: 174, 175 or 176 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-95 molecule or equivalent or mimic or isomiR thereof comprises at least 6 of the 7 nucleotides present in the seed sequence identified as SEQ ID NO: 185 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-193a (i.e. miRNA-193a-3p or miRNA-193a-5p) molecule or equivalent or mimic or isomiR thereof comprises at least 6 of the 7 nucleotides present in the seed sequence identified as SEQ ID NO: 188 or 189 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-497 (i.e. miRNA-497 or miRNA-497*) molecule or equivalent or mimic or isomiR thereof comprises at least 6 of the 7 nucleotides present in the seed sequence identified as SEQ ID NO: 181 or 182 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-509 (i.e. miRNA-509-3p, miRNA-509-5p or miRNA-509-3-5p) molecule or equivalent or mimic or isomiR thereof comprises at least 6 of the 7 nucleotides present in the seed sequence identified as SEQ ID NO: 178, 179 or 180 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-7 (i.e. miRNA-7, miRNA-7-1*, miRNA-7-2*) molecule or equivalent or mimic or isomiR thereof comprises at least 6 of the 7 nucleotides present in the seed sequence identified as SEQ ID NO: 157, 158, or 159 or a part thereof and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

For each of the miRNA molecule identified above, a part of a SEQ ID NO as identified may be at least 19 nucleotides of this SEQ ID NO.

In another preferred embodiment, a miRNA molecule or an equivalent or a mimic thereof comprises at least 6 of the 7 nucleotides present in a given seed sequence and has at least 70% identity over the whole mature sequence (Table 3 shows preferred mature sequences of each of the miRNAs identified herein and Table 6 shows preferred IsomiR equivalents of each of the mature miRNAs identified). Preferably, identity is at least 75%, 80%, 85%, 90%, 95% or higher. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-96 (i.e. miRNA-96 or miRNA-96*) molecule or equivalent or mimic or isomiR thereof comprises at least 6 of the 7 nucleotides present in the seed sequence identified as SEQ ID NO: 164 or 165 or a part thereof and/or has at least 70%, 75%, 80%, 85%, 90%, 95%, 97%, 98%, 99% or 100% identity over SEQ ID NO: 103 or 104 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-203 molecule or equivalent or mimic or isomiR thereof comprises at least 6 of the 7 nucleotides present in the seed sequence identified as SEQ ID NO: 172 or a part thereof and/or has at least 70%, 75%, 80%, 85%, 90%, 95%, 97%, 98%, 99% or 100% identity over SEQ ID NO: 111 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-10b (i.e. miRNA-10b or miRNA-10b*) molecule or equivalent or mimic or isomiR thereof comprises at least 6 of the 7 nucleotides present in the seed sequence identified as SEQ ID NO: 160 or 161 or a part thereof and/or has at least 70%, 75%, 80%, 85%, 90%, 95%, 97%, 98%, 99% or 100% identity over SEQ ID NO: 99 or 100 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-18b (i.e. miRNA-18b or miRNA-18b*) molecule or equivalent or mimic or isomiR thereof comprises at least 6 of the 7 nucleotides present in the seed sequence identified as SEQ ID NO: 162 or 163 or a part thereof and/or has at least 70%, 75%, 80%, 85%, 90%, 95%, 97%, 98%, 99% or 100% identity over SEQ ID NO: 101 or 102 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-129 (i.e. miRNA-129-5p, miRNA-129* or miRNA-129-3p) molecule or equivalent or mimic or isomiR thereof comprises at least 6 of the 7 nucleotides present in the seed sequence identified as SEQ ID NO: 167, 168, or 169 or a part thereof and/or has at least 70%, 75%, 80%, 85%, 90%, 95%, 97%, 98%, 99% or 100% identity over SEQ ID NO: 106, 107 or 108 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-128 molecule or equivalent or mimic or isomiR thereof comprises at least 6 of the 7 nucleotides present in the seed sequence identified as SEQ ID NO: 166 or a part thereof and/or has at least 70%, 75%, 80%, 85%, 90%, 95%, 97%, 98%, 99% or 100% identity over SEQ ID NO: 105 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-184 molecule or equivalent or mimic or isomiR thereof comprises at least 6 of the 7 nucleotides present in the seed sequence identified as SEQ ID NO: 170 or a part thereof and/or has at least 70%, 75%, 80%, 85%, 90%, 95%, 97%, 98%, 99% or 100% identity over SEQ ID NO: 109 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-190b molecule or equivalent or mimic or isomiR thereof comprises at least 6 of the 7 nucleotides present in the seed sequence identified as SEQ ID NO: 171 or a part thereof and/or has at least 70%, 75%, 80%, 85%, 90%, 95%, 97%, 98%, 99% or 100% identity over SEQ ID NO: 110 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-3157 molecule or equivalent or mimic or isomiR thereof comprises at least 6 of the 7 nucleotides present in the seed sequence identified as SEQ ID NO: 173 or a part thereof and/or has at least 70%, 75%, 80%, 85%, 90%, 95%, 97%, 98%, 99% or 100% identity over SEQ ID NO: 112 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-133a molecule or equivalent or mimic or isomiR thereof comprises at least 6 of the 7 nucleotides present in the seed sequence identified as SEQ ID NO: 177 or a part thereof and/or has at least 70%, 75%, 80%, 85%, 90%, 95%, 97%, 98%, 99% or 100% identity over SEQ ID NO: 116 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-200c (i.e. miRNA-200c or miRNA-200c*) molecule or equivalent or mimic or isomiR thereof comprises at least 6 of the 7 nucleotides present in the seed sequence identified as SEQ ID NO: 183 or 184 or a part thereof and/or has at least 70%, 75%, 80%, 85%, 90%, 95%, 97%, 98%, 99% or 100% identity over SEQ ID NO: 122 or 123 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-610 molecule or equivalent or mimic or isomiR thereof comprises at least 6 of the 7 nucleotides present in the seed sequence identified as SEQ ID NO: 190 or a part thereof and/or has at least 70%, 75%, 80%, 85%, 90%, 95%, 97%, 98%, 99% or 100% identity over SEQ ID NO: 129 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-182 (i.e. miRNA-182 or miRNA-182*) molecule or equivalent or mimic or isomiR thereof comprises at least 6 of the 7 nucleotides present in the seed sequence identified as SEQ ID NO: 186, 187 or a part thereof and/or has at least 70%, 75%, 80%, 85%, 90%, 95%, 97%, 98%, 99% or 100% identity over SEQ ID NO: 125 or 126 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-16 (i.e. miRNA-16, miRNA-16-1* or miRNA-16-2*) molecule or equivalent or mimic or isomiR thereof comprises at least 6 of the 7 nucleotides present in the seed sequence identified as SEQ ID NO: 174, 175 or 176 or a part thereof and/or has at least 70%, 75%, 80%, 85%, 90%, 95%, 97%, 98%, 99% or 100% identity over SEQ ID NO: 113, 114 or 115 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-95 molecule or equivalent or mimic or isomiR thereof comprises at least 6 of the 7 nucleotides present in the seed sequence identified as SEQ ID NO: 185 or a part thereof and/or has at least 70%, 75%, 80%, 85%, 90%, 95%, 97%, 98%, 99% or 100% identity over SEQ ID NO: 124 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-193a (i.e. miRNA-193a-3p or miRNA-193a-5p) molecule or equivalent or mimic or isomiR thereof comprises at least 6 of the 7 nucleotides present in the seed sequence identified as SEQ ID NO: 188 or 189 or a part thereof and/or has at least 70%, 75%, 80%, 85%, 90%, 95%, 97%, 98%, 99% or 100% identity over SEQ ID NO: 127, 128 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-497 (i.e. miRNA-497 or miRNA-497*) molecule or equivalent or mimic or isomiR thereof comprises at least 6 of the 7 nucleotides present in the seed sequence identified as SEQ ID NO: 181 or 182 or a part thereof and/or has at least 70%, 75%, 80%, 85%, 90%, 95%, 97%, 98%, 99% or 100% identity over SEQ ID NO: 120 or 121 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-509 (i.e. miRNA-509-3p, miRNA-509-5p or miRNA-5093-5p) molecule or equivalent or mimic or isomiR thereof comprises at least 6 of the 7 nucleotides present in the seed sequence identified as SEQ ID NO: 178, 179 or 180 or a part thereof and/or has at least 70%, 75%, 80%, 85%, 90%, 95%, 97%, 98%, 99% or 100% identity over SEQ ID NO: 117, 118 or 119 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-7 (i.e. miRNA-7 or miRNA-7-1* or miRNA-7-2*) molecule or equivalent or mimic or isomiR thereof comprises at least 6 of the 7 nucleotides present in the seed sequence identified as SEQ ID NO: 157, 158 or159 or a part thereof and/or has at least 70%, 75%, 80%, 85%, 90%, 95%, 97%, 98%, 99% or 100% identity over SEQ ID NO: 96, 97 or 98 or a part thereof. Preferably in this embodiment, a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

In another preferred embodiment, an isomiR of a miRNA molecule has at least 70% identity over the whole isomiR sequence (Table 6 shows preferred isomiR of each of the mature miRNAs identified as SEQ ID NO: 96-129). Preferably, identity is at least 75%, 80%, 85%, 90%, 95% or higher. Preferably in this embodiment, an isomiR of a miRNA molecule or an equivalent or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred isomiR of a miRNA-96 molecule or equivalent thereof comprises at least 6 of the 7 nucleotides present in the seed sequence identified as SEQ ID NO: 164 or 165 or a part thereof and/or has at least 70%, 75%, 80%, 85%, 90%, 95%, 97%, 98%, 99% or 100% identity over SEQ ID NO:222, 223 or 224 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-203 molecule or equivalent thereof comprises at least 6 of the 7 nucleotides present in the seed sequence identified as SEQ ID NO: 172 or a part thereof and/or has at least 70%, 75%, 80%, 85%, 90%, 95%, 97%, 98%, 99% or 100% identity over SEQ ID NO:239, 240, 241 or 242 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-10b (i.e. miRNA-10b or miRNA-10b*) molecule or equivalent thereof comprises at least 6 of the 7 nucleotides present in the seed sequence identified as SEQ ID NO: 160 or 161 or a part thereof and/or has at least 70%, 75%, 80%, 85%, 90%, 95%, 97%, 98%, 99% or 100% identity over SEQ ID NO:194, 195, 196, 197, 198, 199, 200, 201, 202, 203, 204, 205 or 206 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-18b (i.e. miRNA-18b or miRNA-18b*) molecule or equivalent thereof comprises at least 6 of the 7 nucleotides present in the seed sequence identified as SEQ ID NO: 162 or 163 or a part thereof and/or has at least 70%, 75%, 80%, 85%, 90%, 95%, 97%, 98%, 99% or 100% identity over SEQ ID NO:207, 208, 209, 210, 211, 212, 213, 214, 215, 216, 217, 218, 219, 220 or 221 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-129-5p molecule or equivalent thereof comprises at least 6 of the 7 nucleotides present in the seed sequence identified as SEQ ID NO: 167, 168 or 169 or a part thereof and/or has at least 70%, 75%, 80%, 85%, 90%, 95%, 97%, 98%, 99% or 100% identity over SEQ ID NO:230, 231, 232 or 233 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-128 molecule or equivalent thereof comprises at least 6 of the 7 nucleotides present in the seed sequence identified as SEQ ID NO: 166 or a part thereof and/or has at least 70%, 75%, 80%, 85%, 90%, 95%, 97%, 98%, 99% or 100% identity over SEQ ID NO:225, 226, 227, 228 or 229 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-184 molecule or equivalent thereof comprises at least 6 of the 7 nucleotides present in the seed sequence identified as SEQ ID NO: 170 or a part thereof and/or has at least 70%, 75%, 80%, 85%, 90%, 95%, 97%, 98%, 99% or 100% identity over SEQ ID NO:234, 235 or 236 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-190b molecule or equivalent thereof comprises at least 6 of the 7 nucleotides present in the seed sequence identified as SEQ ID NO: 171 or a part thereof and/or has at least 70%, 75%, 80%, 85%, 90%, 95%, 97%, 98%, 99% or 100% identity over SEQ ID NO:237 or 238 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-3157 molecule or equivalent thereof comprises at least 6 of the 7 nucleotides present in the seed sequence identified as SEQ ID NO: 173 or a part thereof and/or has at least 70%, 75%, 80%, 85%, 90%, 95%, 97%, 98%, 99% or 100% identity over SEQ ID NO:243, 244, 245, 246 or 247 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-133a molecule or equivalent thereof comprises at least 6 of the 7 nucleotides present in the seed sequence identified as SEQ ID NO: 177 or a part thereof and/or has at least 70%, 75%, 80%, 85%, 90%, 95%, 97%, 98%, 99% or 100% identity over SEQ ID NO:252, 253, 254, 255 or 256 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-200c* molecule or equivalent thereof comprises at least 6 of the 7 nucleotides present in the seed sequence identified as SEQ ID NO: 183 or a part thereof and/or has at least 70%, 75%, 80%, 85%, 90%, 95%, 97%, 98%, 99% or 100% identity over SEQ ID NO:271, 272 or 273 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-610 molecule or equivalent thereof comprises at least 6 of the 7 nucleotides present in the seed sequence identified as SEQ ID NO: 190 or a part thereof and/or has at least 70%, 75%, 80%, 85%, 90%, 95%, 97%, 98%, 99% or 100% identity over SEQ ID NO:285, 286, 287, 288, 289, 290, 291, 292, 293 or 294 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-182 molecule or equivalent thereof comprises at least 6 of the 7 nucleotides present in the seed sequence identified as SEQ ID NO: 186 or 187 or a part thereof and/or has at least 70%, 75%, 80%, 85%, 90%, 95%, 97%, 98%, 99% or 100% identity over SEQ ID NO:276, 277, 278, 279, 280, 281 or 282 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-16 molecule or equivalent thereof comprises at least 6 of the 7 nucleotides present in the seed sequence identified as SEQ ID NO: 174, 175 or 176 or a part thereof and/or has at least 70%, 75%, 80%, 85%, 90%, 95%, 97%, 98%, 99% or 100% identity over SEQ ID NO:248, 249, 250 or 251 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-95 molecule or equivalent thereof comprises at least 6 of the 7 nucleotides present in the seed sequence identified as SEQ ID NO: 185 or a part thereof and/or has at least 70%, 75%, 80%, 85%, 90%, 95%, 97%, 98%, 99% or 100% identity over SEQ ID NO:274 or 275 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-193a-3p molecule or equivalent thereof comprises at least 6 of the 7 nucleotides present in the seed sequence identified as SEQ ID NO: 188 or 189 or a part thereof and/or has at least 70%, 75%, 80%, 85%, 90%, 95%, 97%, 98%, 99% or 100% identity over SEQ ID NO:283 or 284 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-497 molecule or equivalent thereof comprises at least 6 of the 7 nucleotides present in the seed sequence identified as SEQ ID NO: 181 or 182 or a part thereof and/or has at least 70%, 75%, 80%, 85%, 90%, 95%, 97%, 98%, 99% or 100% identity over SEQ ID NO:266, 267, 268, 269 or 270 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-509 (i.e. miRNA-509-3p, miRNA-509-5p) molecule or equivalent thereof comprises at least 6 of the 7 nucleotides present in the seed sequence identified as SEQ ID NO: 178, 179 or 180 or a part thereof and/or has at least 70%, 75%, 80%, 85%, 90%, 95%, 97%, 98%, 99% or 100% identity over SEQ ID NO:257, 258, 259, 260, 261, 262, 263, 264 or 265 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred isomiR of a miRNA-7 molecule or equivalent thereof comprises at least 6 of the 7 nucleotides present in the seed sequence identified as SEQ ID NO: 157, 158 or 159 or a part thereof and/or has at least 70%, 75%, 80%, 85%, 90%, 95%, 97%, 98%, 99% or 100% identity over SEQ ID NO:191, 192 or 193 or a part thereof and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

For each of the miRNA molecule identified above, a part of a SEQ ID NO as identified may be at least 19 nucleotides of this SEQ ID NO.

Each of the miRNA molecules or equivalents or mimics thereof as identified herein has an acceptable level of an activity of a given miRNA they derive from.

A preferred miRNA molecule or equivalent or a mimic thereof is derived from a given seed sequence (Table 5) or from a given mature sequence (Table 3) or from a given isomiR sequence (Table 6) or from a precursor sequence (Table 2) or from a DNA encoding an RNA precursor (Table 4) by substitution, deletion and/or addition of 1, 2, 3 or more nucleotides and has still an acceptable activity.

Another preferred miRNA molecule or equivalent or mimic thereof has at least 60% identity with a seed sequence (as identified in Table 5) or with a mature sequence (as identified in Table 3) or with a precursor sequence (as identified in Table 2) or with a DNA encoding an RNA precursor (as identified in Table 4) or with an isomiR sequence (as identified in Table 6). Identity may be at least 65%, 70%, 75%, 80%, 85%, 90%, 95%, 99% or 100%. Identity is preferably assessed on the whole SEQ ID NO as identified in a given Table. However, identity may also be assessed on part of a given SEQ ID NO. Part may mean at least 50% of the length of the SEQ ID NO, at least 60%, at least 70%, at least 80%, at least 90% or 100%.

An equivalent of a miRNA molecule may be an isomiR or a mimic. A precursor sequence may result in more than one isomiR sequences depending on the maturation process (see for example miRNA-203, where in certain tissues mulptiple isomiRs have been identified (Table 6). A mimic is a molecule which has a similar or identical activity with a miRNA molecule. In this context a similar activity is given the same meaning as an acceptable level of an activity. A mimic is, in a functional determination, opposed to an antagomir. An antagomir of a miRNA molecule or equivalent or source thereof is therefore a molecule which has an activity which is opposite or reverse to the one of the corresponding miRNA molecule it derives from. An antagomir of a miRNA molecule or equivalent thereof may also be defined as a molecule which is able to antagonize or silence or decrease an activity of said miRNA molecule or equivalent thereof. An activity which is opposite or reverse to the one of the corresponding miRNA molecule it derives from or an activity which is able to antagonize an activity of said miRNA molecule it derives from is preferably an activity which is able to decrease an activity of said miRNA molecule, equivalent or source thereof. In this context, decrease means at least 5%, 10%, 20%, 30%, 40%, 50%, 60%, 70%, 80%, 90%, 95% or 100% decrease of the activity of said miRNA molecule or equivalent or source thereof.

Within the context of the invention, "increasing an activity or the steady-state level of an antagomir or equivalent thereof or of said source thereof" could be replaced by "decreasing an activity or the steady-state level of the corresponding miRNA molecule or equivalent thereof".

The chemical structure of the nucleotides of an antagomir of a miRNA molecule or equivalent or source thereof may be modified to increase stability, binding affinity and/or specificity. Said antagomir may comprise or consists of a RNA molecule or preferably a modified RNA molecule. A preferred modified RNA molecule comprises a modified sugar. One example of such modification is the introduction of a 2'-O-methyl or 2'-O-methoxyethyl group or 2'fluoride group on the nucleic acid to improve nuclease resistance and binding affinity to RNA. Another example of such modification is the introduction of a methylene bridge connecting the 2'-O atom and the 4'-C atom of the nucleic acid to lock the conformation (Locked Nucleic Acid (LNA)) to improve affinity towards complementary single-stranded RNA. A third example is the introduction of a phosphorothioate group as linker between nucleic acid in the RNA-strand to improve stability against a nuclease attack. A fourth modification is conjugation of a lipophilic moiety on the 3' end of the molecule, such as cholesterol to improve stability and cellular delivery. In a preferred embodiment, an antagomir of miRNA molecule consists of a fully LNA-modified phosphorotioate oligonucleotide, termed tiny LNA as described in Obad et al (Obad S. et al, Nature Genetics, on line, 20 Mar. 2011, 43: 371-37). An antagomir as defined herein may comprise 1, 2, 3, 4, 5, 6, 7, 8, 9, 10 or more sugar modifications. It is also encompassed by the invention to introduce more than one distinct sugar modification in one antagomir.

An acceptable level of an activity is preferably that said miRNA or equivalent thereof (miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 or an equivalent thereof) is still able to exhibit an acceptable level of said activity of said miRNA. An activity of a given miRNA (i.e. a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) or equivalent or a mimic thereof is for example the ability to inhibit proliferation, survival, invasion and/or migration and/or to induce apoptosis and/or to interfere with the constitutively active BRAF-MEK-ERK pathway as later defined herein. An acceptable level of an activity is preferably at least 30%, 40%, 50%, 60%, 70%, 80%, 90%, 95% or 100% of the activity of the miRNA they derive from. An antagomir of a miRNA molecule induces a decreased activity of a miRNA molecule it derives from. For example in the context of the invention, an antagomir of a miRNA-221 or of a miRNA-222 is a molecule which induces a decreased activity of a miRNA-221 or of a miRNA-222. Preferably an antagomir of a miRNA-221 or of a miRNA-222 has the ability to inhibit proliferation, survival, invasion and/or migration and/or to induce apoptosis and/or to interfere with the constitutively active BRAF-MEK-ERK or as later described herein for a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 molecule.

Such activity may be as measured in a melanoma cell of an individual or in vitro in a cell by comparison to the activity of the miRNA they derive from. The assessment of the activity may be carried out at the mRNA level, preferably using RT-qPCR. The assessment of the activity may be carried out at the protein level, preferably using assays detecting protein expression, such as Western blot analysis, ELISA, immunohistochemistry or immunofluorescence analysis of cross-sections and/or using an assay as defined later herein (proliferation test, assay for differentiation capacity of a cell, assay for assessing cell death/cell viability, assay for assessing the occurrence of metastases, assay for assessing tumor cell migration, assay for assessing tumor growth, assay for assessing patient survival). The assessment of the activity may be carried out using A375 cells as used in the experimental part.

A preferred activity of a miRNA molecule or equivalent or mimic thereof as identified herein (i.e. miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 or an equivalent or a mimic thereof) or of an antagomir of miRNA-221, miRNA-222 is to induce a detectable inhibition of the proliferation, survival, invasion and/or migration and/or induce apoptosis and/or to interfere with the constitutively active BRAF-MEK-ERK pathway in a subject as later defined herein. A preferred antagomir of miRNA-221 comprises or consists of 5'-GAAACCCAGCAGACAAUGUAGCU-3' (SEQ ID NO:295).

A preferred antagomir of miRNA-222 comprises or consists of 5'-GAGACCCAGUAGCCAGAUGUAGCU-3' (SEQ ID NO:296) (Felicetti F. et al., Cancer Res. 68:2745, 2008).

Preferably, an antagomir is from 23, 24, 25, 26, 27, 28, 29, 30, 31, 32, 33, 34, 35, 36, 37, 38, 39, 40, 41, 42, 43, 44, 45, 46, 47, 48, 49, 50 nucleotides or more and has at least 60% identity with an antagomir sequence SEQ ID NO:295 or 296 as identified above. Identity may be at least 65%, 70%, 75%, 80%, 85%, 90%, 95%, 99% or 100%. Identity is preferably assessed on the whole SEQ ID NO. However, identity may also be assessed on a part of a given SEQ ID NO. A part may mean at least 50% of the length of the SEQ ID NO, at least 60%, at least 70%, at least 80%, at least 90% or 100%.

A source of a miRNA molecule or a source of an equivalent or a source of a mimic of a miRNA molecule may be any molecule which is able to induce the production of a miRNA molecule or of an equivalent thereof as identified herein and which comprises a hairpin-like structure and/or a double stranded nucleic acid molecule. The presence of a hairpin-like structure, may be assessed using the RNAshapes program (Steffen P., et al., Bioinformatics, 22:500, 2006) using sliding windows of 80, 100 and 120 nt or more. The presence of a hairpin-like structure is usually present in a natural or endogenous source of a miRNA molecule whereas a double-stranded nucleic acid molecule is usually present in a recombinant or synthetic source of a miRNA molecule or of an equivalent thereof.

A source of an antagomir of a miRNA molecule or a source of an equivalent of an antagomir of a miRNA molecule may be any molecule which is able to induce the production of said antagomir. Examples of a suitable source of an antagomir are identified in Surdziel E et al (Surdziel E, et al Lentivirus-mediated antagomir expression. M. Methods Mol Biol. 2010; 667:237-48) and in Scherr M et al (Scherr M et al, Lentivirus-mediated antagomir expression for specific inhibition of miRNA function. Nucleic Acids Res. 2007; 35(22):e149. Epub 2007 Nov. 19).

A source of a miRNA molecule or of an equivalent thereof may be a single stranded, a double stranded RNA or a partially double stranded RNA or comprise three strands, an example of which is described in WO2008/10558. In an embodiment, a single stranded miRNA molecule consists of a single stranded miRNA molecule and is therefore not a double stranded miRNA molecule. As used herein partially double stranded refers to double stranded structures that also comprise single stranded structures at the 5' and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure.

Alternatively, a source of a miRNA molecule or of an equivalent or a mimic or an isomiR is a DNA molecule encoding a precursor of a miRNA molecule or of an equivalent or a mimic or an isomiR. Preferred DNA molecules in this context are identified in Table 4. The invention encompasses the use of a DNA molecule encoding a precursor of a miRNA molecule that has at least 70% identity with said sequence as identified in Table 4. Preferably, the identity is at least 75%, 80%, 85%, 90%, 95% or higher. Preferably in this embodiment, a DNA molecule has a length of at least 50, 55, 60, 70, 75, 80, 85, 90, 95, 100, 130, 150, 200, 250, 300, 350, 400, 450, 500 nucleotides or more and has at least 70% identity with a DNA sequence as identified in Table 4 as SEQ ID NO:130-156.

The induction of the production of a given miRNA molecule or of an equivalent or a mimic or an isomiR or an antagomir thereof is preferably obtained when said source is introduced into a cell using an assay as defined below. Cells encompassed by the present invention are later on defined.

A preferred source of a miRNA molecule or of an equivalent or a mimic or an isomiR thereof is a precursor thereof, more preferably a nucleic acid encoding said miRNA molecule or an equivalent or a mimic or an antagomir thereof or a source thereof. A preferred precursor is a naturally-occurring precursor. A precursor may be a synthetic or recombinant precursor.

A preferred precursor of a given miRNA molecule is identified in Table 2. The invention encompasses the use of a precursor of a miRNA molecule or of an equivalent thereof that has at least 70% identity with said sequence. Preferably, identity is at least 75%, 80%, 85%, 90%, 95% or higher as 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400, 450, 500 nucleotides or more and has at least 70% identity with a sequence as identified in Table 2 as SEQ ID NO:69, 70, 71, 72, 73, 74, 75, 76, 77, 78, 79, 80, 81, 82, 83, 84, 85, 86, 87, 88, 89, 90, 91, 92, 93, 94 or 95 or a part thereof.

Accordingly, a preferred source of a miRNA-96 molecule has at least 70%, 75%, 80%, 85%, 90%, 95%, 97%, 98%, 99% or 100% identity with SEQ ID NO:74 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-203 molecule has at least 70%, 75%, 80%, 85%, 90%, 95%, 97%, 98%, 99% or 100% identity with SEQ ID NO:81 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-10b (i.e. miRNA-10b or miRNA-10b*) molecule has at least 70%, 75%, 80%, 85%, 90%, 95%, 97%, 98%, 99% or 100% identity with SEQ ID NO:72 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-18b (i.e. miRNA-18b or miRNA-18b*) molecule has at least 70%, 75%, 80%, 85%, 90%, 95%, 97%, 98%, 99% or 100% identity with SEQ ID NO:73 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-129 (i.e. miRNA-129-5p, miRNA-129* or miRNA-129-3p) molecule has at least 70%, 75%, 80%, 85%, 90%, 95%, 97%, 98%, 99% or 100% identity with SEQ ID NO:77 or 78 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-128 molecule has at least 70%, 75%, 80%, 85%, 90%, 95%, 97%, 98%, 99% or 100% identity with SEQ ID NO:75 or 76 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-184 molecule has at least 70%, 75%, 80%, 85%, 90%, 95%, 97%, 98%, 99% or 100% identity with SEQ ID NO:79 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-190b molecule has at least 70%, 75%, 80%, 85%, 90%, 95%, 97%, 98%, 99% or 100% identity with SEQ ID NO:80 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-3157 molecule has at least 70%, 75%, 80%, 85%, 90%, 95%, 97%, 98%, 99% or 100% identity with SEQ ID NO:82 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-133a molecule has at least 70%, 75%, 80%, 85%, 90%, 95%, 97%, 98%, 99% or 100% identity with SEQ ID NO:85 or 86 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-200c (i.e. miRNA-200c or miRNA-200c*) molecule has at least 70%, 75%, 80%, 85%, 90%, 95%, 97%, 98%, 99% or 100% identity with SEQ ID NO:91 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-610 molecule has at least 70%, 75%, 80%, 85%, 90%, 95%, 97%, 98%, 99% or 100% identity with SEQ ID NO:95 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-182 (i.e. miRNA-182 or miRNA-182*) molecule has at least 70%, 75%, 80%, 85%, 90%, 95%, 97%, 98%, 99% or 100% identity with SEQ ID NO:93 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-16 (i.e. miRNA-16, miRNA-16-1* or miRNA-16-2*) molecule has at least 70%, 75%, 80%, 85%, 90%, 95%, 97%, 98%, 99% or 100% identity with SEQ ID NO:83-84 and/or has a length of at least 50, 55, 60, 70, 75, 80, 85, 90, 95, 100, 130, 150, 200, 250, 300, 350, 400 nucleotides or more.

Accordingly, a preferred source of a miRNA-95 molecule has at least 70%, 75%, 80%, 85%, 90%, 95%, 97%, 98%, 99% or 100% identity with SEQ ID NO:92 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-193a (i.e. miRNA-193a-3p or miRNA-193a-5p) molecule has at least 70%, 75%, 80%, 85%, 90%, 95%, 97%, 98%, 99% or 100% identity with SEQ ID NO:94 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-497 (i.e. miRNA-497 or miRNA-497*) molecule has at least 70%, 75%, 80%, 85%, 90%, 95%, 97%, 98%, 99% or 100% identity with SEQ ID NO:90 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-509 (i.e. miRNA-509-3p, miRNA-509-5p or miRNA-509-3-5p) molecule has at least 70%, 75%, 80%, 85%, 90%, 95%, 97%, 98%, 99% or 100% identity with SEQ ID NO:87, 88 or 89 or a part thereof and/or has a length of at least 50, 55, 60, 70, 75, 80, 85, 90, 95, 100, 130, 150, 200, 250, 300, 350, 400, 450, 500 nucleotides or more.

Accordingly, a preferred source of a miRNA-7 (i.e. miRNA-7, miRNA-7-1* or miRNA-7-2*) molecule has at least 70%, 75%, 80%, 85%, 90%, 95%, 97%, 98%, 99% or 100% identity with SEQ ID NO:69, 70 or 71 or a part thereof and/or has a length of at least 50, 55, 60, 70, 75, 80, 85, 90, 95, 100, 130, 150, 200, 250, 300, 350, 400, 450, 500 nucleotides or more.

For each of the source of miRNA molecule identified above, a part of a SEQ ID NO as identified may be at least 100 or 200 nucleotides of this SEQ ID NO.

In this context, it is pointed that several precursors of a given mature miRNA molecule may lead to an identical miRNA molecule. For example, miRNA-7 (i.e. miRNA-7, miRNA-7-1* or miRNA-7-2*) may originate from precursor Hsa-miR-7-1, Hsa-miR-7-2 or Hsa-miR-7-3 (preferably identified as being SEQ ID NO: 69, 70 or 71). In a preferred embodiment, a Hsa-miR-7-3 or a molecule having at least 70%, 75%, 80%, 85%, 90%, 95%, 97%, 98%, 99% or 100% identity with Hsa-miR-7-3 or SEQ ID NO:71 is used as a precursor of a miRNA-7 molecule.

For example, miRNA-16 (i.e. miRNA-16-, miRNA-16-1* or miRNA-16-2* may originate from precursor Hsa-miR-16-1 or Hsa-miR-16-2 (preferably identified as being SEQ ID NO: 83 or 84). In a preferred embodiment, a Hsa-miR-16-2 or a molecule having at least 70%, 75%, 80%, 85%, 90%, 95%, 97%, 98%, 99% or 100% identity with Hsa-miR-16-2 or SEQ ID NO: 84 is used as a precursor of a miRNA-16 molecule.

For example, miRNA-509 (i.e. miRNA-509-3p, miRNA-509-5p or miRNA-509-3-5p) may originate from precursor Hsa-miR-509-1, Hsa-mi-R-509-2 or Hsa-miR-509-3 (preferably identified as being SEQ ID NO: 87, 88 or 89). In a preferred embodiment, a Hsa-miR-509-1 or a molecule having at least 70%, 75%, 80%, 85%, 90%, 95%, 97%, 98%, 99% or 100% identity with Hsa-miR-509-1 or SEQ ID NO: 87 is used as a precursor of a miRNA-509 molecule.

For example, miRNA-128 may originate from precursor Hsa-miR-128-1 or Hsa-mi-R-128-2 (preferably identified as being SEQ ID NO: 75 or 76). In a preferred embodiment, a Hsa-miR-128-1 or a molecule having at least 70%, 75%, 80%, 85%, 90%, 95%, 97%, 98%, 99% or 100% identity with Hsa-miR-128-1 or SEQ ID NO: 75 is used as a precursor of a miRNA-128 molecule. In a preferred embodiment, a Hsa-miR-128-2 or a molecule having at least 70%, 75%, 80%, 85%, 90%, 95%, 97%, 98%, 99% or 100% identity with Hsa-miR-128-2 or SEQ ID NO: 76 is used as a precursor of a miRNA-128 molecule.

For example, miRNA-129 (i.e. miRNA-129-5p, miRNA-129* or miRNA-129-3p) may originate from precursor Hsa-miRNA-129-1 or Hsa-mi-RNA-129-2 (preferably identified as being SEQ ID NO: 77 or 78). In a preferred embodiment, a Hsa-miRNA-129-2 or a molecule having at least 70%, 75%, 80%, 85%, 90%, 95%, 97%, 98%, 99% or 100% identity with Hsa-miRNA-129-2 or SEQ ID NO: 78 is used as a precursor of a miRNA-129 molecule.

For example, miRNA-133a may originate from precursor Hsa-miR-133a-1 or Hsa-mi-R-133a-2 (preferably identified as being SEQ ID NO: 85 or 86). In a preferred embodiment, a Hsa-miR-133a-1 or a molecule having at least 70%, 75%, 80%, 85%, 90%, 95%, 97%, 98%, 99% or 100% identity with Hsa-miR-133a-1 or SEQ ID NO: 85 is used as a precursor of a miRNA-133a molecule.

Preferred sources or precursors have been defined later herein. A preferred source includes or comprises an expression construct comprising a nucleic acid, i.e. DNA encoding said precursor of said miRNA, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or lentiviral vector. Other preferred vectors are oncolytic viral vectors. Such vectors are further described herein below.

Alternatively, a source may be a synthetic miRNA molecule or a chemical mimic or a chemical antagomir as further defined in the part dedicated to general definitions.

Within the whole invention, each time is referred to "a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 and/or an equivalent and/or a source thereof" one may further refer to the preferred subcombinations of miRNA as identified below for which best experimental results have been obtained so far:

A miRNA molecule is preferably a miRNA-16, miRNA-10b, miRNA-18bmiRNA-96, miRNA-203, miRNA-7, miRNA-190b and/or miRNA-128 and/or an equivalent and/or a source thereof.

More preferably, a miRNA molecule is:
a miRNA-96 and/or miRNA-16 and/or an equivalent and/or a source thereof or
a miRNA-16 and/or miRNA-10b and/or an equivalent and/or a source thereof or
a miRNA-96 and/or miRNA-10b and/or an equivalent and/or a source thereof or
a miRNA-96 and/or miRNA-203 and/or an equivalent and/or a source thereof or
a miRNA-128 and/or miRNA-10b* and/or an equivalent and/or a source thereof or
a miRNA-16 and/or miRNA-203 and/or an equivalent and/or a source thereof or
a miRNA-190b and/or miRNA-203 and/or an equivalent and/or a source thereof or
a miRNA-18b and/or miRNA-203 and/or equivalent and/or source thereof or
a miRNA-7 and/or miRNA-203 and/or equivalent and/or source thereof.

In another preferred embodiment, a miRNA molecule is: a miRNA-96, miRNA-129, miRNA-509, miRNA-128 and/or miRNA-16, and/or an equivalent and/or a source thereof. More preferably, in this preferred embodiment, a miRNA molecule is a miRNA-96 and/or miRNA-129 and/or equivalent and/or source thereof.

In another preferred embodiment, a miRNA molecule is: a miRNA-16, miRNA-10b, miRNA-96, miRNA-203, miRNA-129, miRNA-509, miRNA-128 and/or miRNA-18b and/or equivalent and/or source thereof. More preferably, in this preferred embodiment, a miRNA molecule is a miRNA-16 and/or miRNA-96 and/or equivalent and/or source thereof.

The detection of the presence of a miRNA molecule or of an equivalent or a mimic or an isomiR or an antagomir molecule or an equivalent thereof may be carried out using any technique known to the skilled person. The assessment of the expression level or of the presence of a miRNA molecule or of an equivalent or a mimic or an antagomir thereof is preferably performed using classical molecular biology techniques such as (real time) qPCR, microarrays, bead arrays, RNAse protection analysis or Northern analysis. The skilled person will understand that alternatively or in combination with the quantification of a miRNA molecule or of an equivalent or a mimic or an antagomir thereof, the quantification of a substrate of a corresponding miRNA molecule or of an equivalent thereof or of any compound known to be associated with a function of said miRNA molecule or of said equivalent thereof or the quantification of a function or activity of said miRNA molecule or of said equivalent thereof using a specific assay is encompassed within the scope of the invention.

Preferred compositions and formulations are all defined later herein. A miRNA molecule or an equivalent or a mimic or an isomiR or an antagomir thereof may be used as such as a naked molecule, with or without chemical modifications, or encapsulated into a particle or conjugated to a moiety. A preferred composition comprises a miRNA molecule or an equivalent or an antagomir thereof encapsulated into a nanoparticle or a liposomal structure. A miRNA molecule or equivalent or an antagomir thereof may be an aptamer-miRNA hybrid. An aptamer-miRNA is defined as a miRNA linked to a nucleic acid (RNA or DNA) oligonucleotide, the latter adopting a conformation that targets the aptamer-miRNA hybrid molecule to a cell-surface protein present on a melanoma cell. The aptamer-tagged miRNA can be linked to e.g. polyethylene glycol, which increases the chimera's circulating half-life (Dassie, J. P. et al., Nat. Biotechnol. 27:839-849, 2009).

Any disease or condition wherein melanoma is involved or associated or diseases or conditions associated with activated BRAF pathway may be prevented, delayed, cured, regressed and/or treated with a molecule as defined herein. In a disease or condition of the invention, melanoma may be detectable during the development of said disease or condition, i.e. after the apparition of a symptom of said disease or condition.

Accordingly, within the context of the invention, a melanoma encompasses each stage of said melanoma:
dysplastic or benign nevi (common acquired or congenital), or
in situ melanoma wherein melanocytes undergo radial growth phase, in which the growth expands laterally. Melanoma cells are only present in the epidermis, or
a melanoma wherein melanoma cells have progressed to the vertical growth phase and are able to invade the dermis of the skin, usually 1 to 4 mm in depth but wherein no signs of metastasis/spreading of melanoma cells are visible, or
a melanoma wherein melanoma cells already have metastasized either to a lymph node and/or to distant organs such as liver, lung and/or brain.

The skilled person will understand that each stage which could be considered as intermediate within each of the above identified stages is also encompassed by the present invention. Melanoma may be detected using any technique known to the skilled person. Alternatively, melanoma and any stage thereof as identified above may be diagnosed using a method of the invention as later identified herein. The assessment of the expression of a miRNA molecule (i.e. miRNA-10b, miRNA-18b, miRNA-96, miRNA-129, miRNA-128-1, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) is preferably carried out in a tumor biopsy or section at several time points for a given subject or at one or several time points for a given subject and a healthy control. The assessment may be carried out each week, each month. The most important prognostic measure of progression is the Breslow thickness, which measures vertical thickness of the lesion: from the upper layer of the epidermis to the innermost depth of invasion (Balch C. M. et al., J. Clin. Oncol., 2001). Other prognostic factors are the mitotic rate of the lesion (Scolyer R. A. et al., Am. J. Surg. Pathol. 2003) and vascular invasion (Mraz-Gernhard S. et al., Arch. Dermatol., 1998).

A disease or condition wherein melanoma is involved or associated could also be named cutaneous melanoma, a tumor of melanocytes, an uveal melanoma (i.e. tumor of melanocytes found in the eye), a tumor of melanocytes found in the bowel, Lentigo maligna, Lentigo maligna melanoma, superficially spreading melanoma, acral lentiginous melanoma, mucosal melanoma, modular melanoma, polypoid melanoma, desmoplastic melanoma, amelanotic melanoma, soft-tissue melanoma, melanoma with small nevus-like cells or melanoma with features of a Spitz nevus.

Within the context of the invention, a melanoma is a cancer present in or originating from melanocytes. Melanocytes are the cells that produce the skin coloring or pigment known as melanin. Melanin helps protect the deeper layers of the skin from the harmful effects of the sun.

By contrast to melanoma, there exist other types of skin cancers classified as non-melanomas skin cancer, usually starting in either basal cells or squamous cells. These cells are located at the base of the outer layer of the skin or cover the internal and external surfaces of the body. Most non-melanoma skin cancers develop on sun-exposed areas of the body, like the face, ear, neck, lips, and the backs of the hands. Depending on the type, they can be fast or slow growing, but they rarely spread to other parts of the body. Non-melanoma skin cancers may include benign, pre-malignant and malignant tumours of keratinocytes, which are the predominant type of cutaneous epithelial cells. Keratinocyte cancers include epidermal tumours such as basal cell carcinoma (BCC), squamous cell carcinoma (SCC) or a pre-malignant lesion thereof, hair follicle tumors, such as trichoblastoma, trichoepitelioma, pilomatrixoma, pilomatrixcarcinoma, trichoadenoma, trichofolliculoma; sweat gland tumors such as adnexcarcinoma, mucinous eccrin carcinoma, porocarcinoma; and premalignant lesions of the skin such as actinic keratosis, morbus Bowen, and erythroplasia Queyrat.

These two types of skin cancers (melanoma versus non-melanoma skin cancers) are totally irrelated from a biological point of view. Accordingly, preferably the invention relates to melanoma and not to non-melanoma skin cancer originating from basal or squamous cells and called BCC or SCC.

A disease or condition associated with activated BRAF pathway may be a melanoma as identified herein or papillary thyroid cancer, colorectal cancer, serous ovarian cancer or lung cancer.

There is currently no effective known medicament that may be used for specifically preventing, treating, regressing, curing and/or delaying a disease or condition associated with melanoma or a disease or condition associated with activated BRAF pathway in a subject. The invention encompasses to use a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 molecule, an equivalent or a mimic or an isomiR or a source thereof or a composition comprising said miRNA molecule or equivalent thereof or a source thereof to this end. This use includes pharmacologically increasing an activity or the steady-state level of said miRNA molecule or equivalent or mimic or isomiR thereof or of said source thereof in a subject, in a cell of said subject, in a tissue of said subject or in body fluid of said subject.

In this use, an activity or steady-state level of said miRNA molecule or equivalent or mimic or isomiR thereof or source thereof is increased in order to induce a detectable decrease of proliferation, survival, invasion and/or migration and/or to induce apoptosis and/or to interfere with the constitutively active BRAF-MEK-ERK pathway in a subject, preferably in melanoma cells or tumor cells from said subject.

The assessment of the expression of said miRNA molecule is preferably carried out in a tumor biopsy or section at several time points for a given subject or at one or several time points for a given subject and a healthy control. The assessment may be carried out at regular time intervals, e.g. each week, each month. The increase/decrease may therefore be assessed regularly, e.g. each week, each month. A detectable decrease of proliferation and/or a detectable decrease of survival and/or a detectable increase in apoptosis and/or a detectable decrease in invasion and/or migration is preferably assessed as later explained herein to define an anti-tumor effect. In order to assess an interference with the constitutively active BRAF-MEK-ERK pathway, the activation state of this pathway is preferably assessed before treatment in melanoma or tumor cells from said subject. The activation of said pathway may be detected by direct measurement of phosphorylation of MEK and/or ERK1 and/or ERK2 in vitro and/or stimulation of ERK signalling in vivo (Davies H. et al., Nature 417: 949, 2002, Ikenoue T. et al., Cancer Res. 63: 8132, 2003, Houben R. et al., J. Carcinogen. 3: 6, 2004, Wan P. T. et al., Cell 116: 855, 2004) or by measurement of phosphorylation of transcription factors downstream of ERK1/2. In a preferred embodiment, there is an interference with a constitutively active BRAF-MEK-ERK pathway when MEK phosphorylation and/or activity of the ERK signalling is reduced compared to cells with an unencumbered constitutively active BRAF-MEK-ERK pathway, which consequently results in inhibition of proliferation and induction of apoptosis (Hingorani S. R. et al., and Karasarides M. et al.).

An activity or steady-state level of said miRNA molecule (i.e. a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) or equivalent or mimic or isomiR thereof or source thereof may be increased at the level of the miRNA molecule (or equivalent thereof) itself, e.g. by providing said miRNA molecule or equivalent thereof to a subject, preferably to a cell of a subject, or to a tissue of said subject, or to an organ of said subject or to said subject said miRNA molecule or equivalent thereof being from an exogenous source. For provision of a miRNA molecule or equivalent thereof from an exogenous source, said miRNA molecule or equivalent thereof may conveniently be produced by expression of a nucleic acid encoding said miRNA molecule or equivalent thereof or encoding a source of said miRNA molecule or equivalent thereof in a suitable host cell as described below or as completely synthetic molecules by chemical synthesis.

Preferably, however, an activity or steady-state level of said miRNA molecule (a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) or equivalent thereof is increased by regulating the expression level of a nucleotide sequence encoding said miRNA molecule or equivalent thereof or encoding a source of said miRNA molecule or equivalent thereof. Preferably, the expression level of a nucleotide sequence is regulated in a cell of said subject or in a tissue of said subject or in the subject. The expression level of a miRNA molecule or equivalent thereof or a source of said miRNA molecule or equivalent thereof may be increased by introduction of a miRNA, and equivalent, or a source thereof, or an expression construct (or vector) into a cell, tissue, organ or body fluid of said subject, or in the subject whereby an expression vector comprises a nucleotide sequence comprising said miRNA molecule (i.e. a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) or equivalent thereof or comprising a source of said miRNA molecule or equivalent thereof, and whereby a nucleotide sequence is under control of a promoter capable of driving expression of a nucleotide sequence in said cell, tissue, organ, subject. The expression level of said miRNA molecule or equivalent thereof or source thereof may also be increased by introduction of an expression construct into a cell, tissue, organ, subject, whereby a construct comprises a nucleotide sequence encoding a factor capable of transactivation of an endogenous nucleotide sequence encoding a miRNA molecule or equivalent thereof.

A use of the invention preferably comprises the step of administering to a subject a therapeutically effective amount of a pharmaceutical composition comprising a nucleic acid construct for increasing the activity or steady state level of a miRNA molecule or equivalent as defined herein (i.e. miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7). A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is an AAV or lentiviral vector. Alternatively, a use of the invention preferably comprises the step of administering to a subject a therapeutically effective amount of a pharmaceutical composition comprising a miRNA molecule (i.e. a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7), an equivalent or a source thereof as defined herein.

In a use of the invention, a cell, a tissue, an organ or body fluid is preferably from a subject suspected to have a high risk of having a melanoma or of having a disease or condition associated with melanoma or having a disease or condition associated with activated BRAF pathway due for example to its age or its genetic background or to its diet or to the country wherein he lives or to his frequency of sun exposition or to his frequency of use of tanning salons. Alternatively, in another preferred embodiment, use of the invention is applied on a cell, tissue, organ or body fluid from a subject diagnosed as either having a predictive risk for developing later a disease or condition associated with melanoma or having a disease or condition associated with activated BRAF pathway. A diagnostic method used is preferably one of the inventions as described herein. Alternatively, a cell, a tissue or organ to be treated may be selected based on risk of progression of the disease or condition associated with melanoma or having a disease or condition associated with activated BRAF pathway. Such risk of progression may be assessed using classical clinic-pathological criteria or biomarker-based prognosis known to the skilled person. It is also encompassed by the invention to administer a miRNA molecule (i.e. a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7) or equivalent thereof or a precursor thereof or a composition comprising said miRNA molecule or equivalent thereof or source thereof into a tissue or organ of said subject. In the invention, a preferred cell, tissue or organ is a cell, tissue or organ that is or comprises a melanoma or skin or eye cell or tissue or is or comprises the eye or the skin as organ. In the invention, another preferred cell or tissue is a cell or tissue organ that is or comprises a tumor and that is a thyroid gland, a colon, a lung or an ovary cell or tissue, or a cell or tissue that is or comprises a tumor that is derived from a thyroid gland tumor, a colon tumor, a lung tumor or an ovary tumor. A preferred organ may be or may comprise the thyroid gland, the colon, the lung or the ovary as organ, or an organ that is or comprises a tumor that is derived from a thyroid gland tumor, a colon tumor, a lung tumor or an ovary tumor.

A treatment of a disease or condition associated with melanoma may include a treatment that prevents melanoma in a tumor cell that has not yet metastasized or regresses melanoma in a tumor cell that has already formed metastases and/or is migrating from the primary tumor to distant sites in the body.

A treatment of a disease or condition associated with activated BRAF pathway may include a treatment that regresses such diseases or conditions in a tumor cell that has already formed metastases and/or is migrating from the primary tumor to distant sites in the body.

In another use, the invention mentioned herein may be combined with standard treatments of disease or condition associated with melanoma or of a disease or condition associated with activated BRAF pathway such as chemotherapy, radiotherapy or surgery. Examples of chemotherapeutic agents are exemplified later herein.

Although gene therapy is a possibility for preventing, treating, regressing, curing and/or delaying a condition or a disease associated with melanoma or of a disease or condition associated with activated BRAF pathway, other possible treatments may also be envisaged. For example, treatment by "small molecule" drugs to steer certain molecular pathways in the desired direction, is also preferred. These small molecules are preferably identified by the screening method of the invention as defined later herein.

In the context of the invention, preventing, treating, regressing, curing and/or delaying a disease or condition associated with melanoma or a disease or condition associated with activated BRAF pathway may mean that:

at least a symptom of this disease or condition has been improved, and/or at least a parameter associated with this disease or condition has been improved.

The improvement may be measured during at least one week, one month, six months of treatment or more. A symptom may be the presence of metastases as explained below.

A parameter may be the assessment of the interference with constitutive active BRAF-MEK-ERK pathway as explained herein. In the context of the invention, preventing, treating, regressing, curing and/or delaying a disease or condition associated with melanoma or a disease or condition associated with activated BRAF pathway may be replaced by achieving an anti-tumor effect. Unless otherwise indicated, an anti-tumor effect is preferably assessed or detected before treatment and after at least one week, two weeks, three weeks, fours weeks, one month, two months, three months, four months, five months, six months or more in a treated subject. An anti-tumor effect is preferably identified in a subject as:

an inhibition of proliferation or a detectable decrease of proliferation of tumor cells or a decrease in cell viability of tumor cells or melanocytes, and/or an increase in the capacity of differentiation of tumor cells, and/or an increase in tumor cell death, which is equivalent to a decrease in tumor cell survival, and/or a delay in occurrence of metastases and/or of tumor cell migration, and/or an inhibition or prevention or delay of the increase of a tumor weight or growth, and/or a prolongation of patient survival of at least one month, several months or more (compared to those not treated or treated with a control or compared with the subject at the onset of the treatment).

In the context of the invention, a patient may survive and may be considered as being disease free. Alternatively, the disease or condition may have been stopped or delayed or regressed. An inhibition of the proliferation of tumor cells may be at least 20%, 30%, 40%, 50%, 55%, 60%, 65%, 70% or 75% or more. Proliferation of cells may be assessed using known techniques. An decrease in cell viability of tumor cells or melanocytes may be a decrease of at least 20%, 30%, 40%, 50%, 55%, 60%, 65%, 70% or 75% or more. Such decrease may be assessed 4 days after transfection with a given miRNA molecule, equivalent or source thereof. Cell viability may be assessed via known techniques such as the MTS assay, preferably as used in the experimental part.

An induction of tumor cell death may be at least 1%, 5%, 10%, 15%, 20%, 25%, or more. A decreased in tumor cell survival may be a decrease of at least 1%, 5%, 10%, 15%, 20%, 25%, or more. Tumor cell death may be assessed by measurement of radiolabeled Annexin A5, a molecular imaging agent to measure cell death in vitro, and non-invasively in patients with cancer (Schutters K. et al., Apoptosis 2010 and de Saint-Hubert M. et al., Methods 48: 178, 2009).

Tumor growth may be inhibited at least 5%, 10%, 20%, 30%, 40%, 50%, 55%, 60%, 65%, 70% or 75%, or more. Tumor growth may be assessed using techniques known to the skilled person. Tumor growth may be assessed using MRI (Magnetic Resonance Imaging) or CT (Computer Tomography).

In certain embodiments, tumor weight increase or tumor growth may be inhibited at least 20%, 30%, 40%, 50%, 55%, 60%, 65%, 70% or 75%, or more. Tumor weight or tumor growth may be assessed using techniques known to the skilled person.

The detection of tumor growth or the detection of the proliferation of tumor cells may be assessed in vivo by measuring changes in glucose utilization by positron emission tomography with the glucose analogue 2-[18F]-fluor-2-deoxy-D-glucose (FDG-PET) or [18F]-'3-fluoro-'3-deoxy-L-thymidine PET. An ex vivo alternative may be staining of a tumor biopsy with Ki67.

A delay in occurrence of metastases and/or of tumor cell migration may be a delay of at least one week, one month, several months, one year or longer. The presence of metastases may be assessed using MRI, CT or Echography or techniques allowing the detection of circulating tumour cells (CTC). Examples of the latter tests are CellSearch CTC test (Veridex), an EpCam-based magnetic sorting of CTCs from peripheral blood. An increase in the capacity of differentiation of tumor cells may be assessed using a specific differentiation marker and following the presence of such marker on cells treated. Preferred markers or parameters have already been identified herein, i.e. p16 (Oshie S. et al., J. Cut. Pathol. 35: 433, 2008), Trp-1 and PLZF (Felicetti F., Oncogene 23: 4567, 2004), c-Kit, MITF, Tyrosinase (Felicetti F., Cancer Res. 68: 2745, 2008) and Melanin. This may be done using RT-PCR, western blotting or immunohistochemistry. An increase of the capacity of differentiation may be at least a detectable increase after at least one week of treatment using any of the identified techniques. Preferably, the increase is of 1%, 5%, 10%, 15%, 20%, 25%, or more, which means that the number of differentiated cells within a given sample will increase accordingly. In certain embodiments, tumor growth may be delayed at least one week, one month, two months or more. In a certain embodiment, an occurrence of metastases is delayed at least one week, two weeks, three weeks, fours weeks, one months, two months, three months, four months, five months, six months or more.

In a further preferred embodiment, there is provided a composition further comprising another miRNA molecule selected from:

a) at least one of miRNA-13, Let-7 and Let-7a and/or an equivalent or a source thereof, and/or b) at least one antagomir of miRNA-221 and miRNA-222 and/or an equivalent or a source thereof.

Since not each of the identified miRNAs molecules or equivalents thereof is expected to have the same target genes, in a preferred embodiment of the invention it is assumed that the use of at least one miRNA molecule selected from the group consisting of a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and a miRNA-7 or equivalent thereof of source thereof optionally combined with at least one of the miRNA molecules, or equivalents thereof or sources thereof identified above under a) and/or b) allows a more effective treatment of a disease or condition associated with melanoma or of a disease or condition associated with activated BRAF pathway. A tumor treated by a composition or a cocktail of at least a miRNA-molecule such as a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7, or equivalent or source thereof is expected to have fewer possibilities to escape or to resist said treatment. In a further preferred embodiment, it is encompassed to diagnose the expression of each of the miRNA molecules or of their target genes as identified herein and depending on the outcome to adapt the identity of the miRNA molecules used for the treatment.

When the invention relates to a composition comprising more than one miRNA molecule or equivalent thereof or source thereof, it is encompassed that each miRNA molecule or equivalent thereof or source thereof may be present each in a separate composition, each composition being sequentially or simultaneously administered to a subject. Alternatively, it is also encompassed that more than one miRNA molecules or equivalents thereof or sources thereof is present in a composition as defined herein.

In a further aspect, there is provided the use of a miRNA molecule such as a miRNA-10b, miRNA-18b, miRNA-96, miRNA-129, miRNA-128-, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7, an equivalent or a source thereof or a composition comprising said miRNA molecule, an equivalent or a source thereof for the manufacture of a medicament for preventing, treating, regressing, curing and/or delaying a disease or a condition associated with melanoma or a disease or condition associated with activated BRAF pathway. Each feature of this further aspect has already been described herein.

In a further aspect, there is provided a method for preventing preventing, treating, regressing, curing and/or delaying a condition or disease associated with melanoma or a disease or condition associated with activated BRAF pathway by administering a miRNA molecule such as a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 or equivalent thereof or source thereof or composition as earlier defined herein to a subject in the need thereof. Each feature of this further aspect has already been described herein.

In a further aspect, there is provided a method for diagnosing melanoma or a disease or condition associated with melanoma or a disease or condition associated with activated BRAF pathway in a subject, the method comprising the steps of:
(a) determining the expression level of a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7, an equivalent or a source thereof in a subject, and optionally
(b) comparing the expression level of said molecule or equivalent thereof or source thereof as defined in (a) with a reference value for the expression level of said molecule, equivalent or source thereof, the reference value preferably being the average value for the expression level of said molecule, equivalent or source thereof in a healthy subject.

In the context of the invention, diagnosis means either a predictive risk assessment of a subject for developing a disease or a condition associated with melanoma or for developing melanoma itself or for developing a disease or condition associated with activated BRAF pathway. In the context of the invention, a subject may be an animal or a human being. Preferably, a subject is a human being.

Since the expression levels of these nucleotide sequences and/or amounts of corresponding miRNA molecule or equivalent thereof or source thereof may be difficult to be measured in a subject, a sample from a subject is preferably used. A corresponding sample is used from a healthy subject.

According to another preferred embodiment, the expression level (of a nucleotide sequence or miRNA molecule or equivalent or source thereof) is determined ex vivo in a sample obtained from a subject. The sample preferably comprises a body fluid of a subject. A body fluid may comprise or be derived from blood, serum, plasma, CSF, stool, urine or a tissue biopsy or a tumor biopsy of a subject. Preferred tissue comprises a, is derived from a or consists of skin, eye, thyroid gland, colon, lung or ovary cell. It is specifically contemplated that the invention can be used to evaluate or diagnose differences between stages of disease or condition associated with melanoma or of a disease or condition associated with activated BRAF pathway, such as between pre-cancer and cancer, or between a primary tumor and a metastasized tumor and/or between any of the specific melanoma stages earlier identified herein.

An increase or decrease of the expression level of a nucleotide sequence (or steady state level of an encoded miRNA molecule or equivalent or source thereof) is preferably defined as being a detectable change of the expression level of a nucleotide (or steady state level of an encoded miRNA molecule or equivalent or source thereof or any detectable change in a biological activity of a miRNA molecule or equivalent or source thereof) using a method as defined earlier on as compared to the expression level of a corresponding nucleotide sequence (or steady state level of a corresponding encoded miRNA molecule or equivalent or source thereof) in a corresponding sample from a healthy subject. A preferred nucleotide sequence is a sequence encoding a precursor of a miRNA molecule or equivalent thereof. According to a preferred embodiment, an increase or decrease of a miRNA activity is quantified using a specific assay for a miRNA activity. A preferred assay for the assessment of a miRNA activity had already been defined earlier herein.

Preferably, a decrease of the expression level of a nucleotide sequence means a decrease of at least 5% of the expression level of the nucleotide sequence using arrays or qPCR. More preferably, a decrease of the expression level of a nucleotide sequence means an decrease of at least 10%, even more preferably at least 20%, at least 30%, at least 40%, at least 50%, at least 70%, at least 90%, or 100%. In this case, there is no detectable expression.

Preferably, a decrease of the expression level of a miRNA molecule or equivalent or source thereof means a decrease of at least 5% of the expression level of the miRNA using qPCR, microarrays or Northern analysis. Preferably qPCR is stem-loop RT qPCR. More preferably, a decrease of the expression level of a miRNA molecule or equivalent or source thereof means a decrease of at least 10%, even more preferably at least 20%, at least 30%, at least 40%, at least 50%, at least 70%, at least 90%, or 100%. In this case, there is no detectable expression.

Preferably, a decrease of a miRNA activity means a decrease of at least 5% of a miRNA activity using a suitable assay. More preferably, a decrease of a miRNA activity means a decrease of at least 10%, even more preferably at least 20%, at least 30%, at least 40%, at least 50%, at least 70%, at least 90%, or 100%. In this case, there is no detectable activity.

Preferably, an increase of the expression level of a nucleotide sequence means an increase of at least 5% of the expression level of the nucleotide sequence using any of the techniques mentioned herein. More preferably, an increase of the expression level of a nucleotide sequence means an increase of at least 10%, even more preferably at least 20%, at least 30%, at least 40%, at least 50%, at least 70%, at least 90%, at least 150% or more.

Preferably, an increase of the expression level of a miRNA molecule or equivalent or source thereof means an increase of at least 5% of the expression level of the miRNA molecule or equivalent or source thereof using RT-qPCR, preferably stem-loop RT qPCR. More preferably, an increase of the expression level of a miRNA molecule or equivalent or source thereof means an increase of at least 10%, even more preferably at least 20%, at least 30%, at least 40%, at least 50%, at least 70%, at least 90%, at least 150% or more.

Preferably, an increase of a miRNA activity means an increase of at least 5% of a miRNA activity using a suitable assay. More preferably, an increase of a miRNA activity means an increase of at least 10%, even more preferably at least 20%, at least 30%, at least 40%, at least 50%, at least 70%, at least 90%, at least 150% or more.

Preferably, an expression level is determined ex vivo in a sample obtained from a subject. More preferably, the sample is as earlier defined herein and wherein subsequently, a given nucleotide sequence and/or miRNA molecule or equivalent or source thereof is extracted and purified using known methods to the skilled person. More preferably, the sample is or comprises or is derived from a tumor biopsy, blood or urine.

In a diagnostic method of the invention preferably the expression level of more than one, more preferably of at least 2, 3, 4, 5, 6, 7, 8, 9, 10, 11, 12, 13, 14, 15 miRNAs molecule or equivalent or source thereof and/or the steady state levels of the corresponding miRNAs molecule or equivalent or source thereof are determined.

Accordingly in a preferred method, in step (a) one determines the expression level of another miRNA molecule or equivalent or source thereof selected from:
a) at least one of miRNA-13, Let-7, and Let-7a and/or an equivalent or a source thereof and/or,
b) at least one of miRNA-221 and miRNA-222 and/or an equivalent or a source thereof.

In a further preferred method, melanoma or a disease or condition associated with melanoma or a disease or condition associated with activated BRAF pathway is diagnosed when the comparison leads to the finding of a decrease of the expression level of a miRNA-10b, miRNA-18b, miRNA-96, miRNA-129, miRNA-128-, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7, an equivalent or a source thereof.

In a further preferred method, melanoma or a disease or condition associated with melanoma or a disease or condition associated with activated BRAF pathway is diagnosed when the comparison leads to the finding of a decrease of the expression level of said miRNA molecule, equivalent or a source thereof and a decrease of the expression level of at least one of another miRNA selected from:
a) at least one of miRNA-13, Let-7, and Let-7a and/or an equivalent or a source thereof, and/or an increase of the expression level of at least one of another miRNA selected from:
b) at least one miRNA-221 and miRNA-222 and/or an equivalent or a source thereof.

In a further aspect, there is provided a method for identification of a substance or a molecule capable of preventing, treating, regressing, curing and/or delaying melanoma or a condition or disease associated with melanoma or a disease or condition associated with activated BRAF pathway in a subject, the method comprising the steps of:
(a) providing a test cell population capable of expressing a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 molecule or equivalent thereof or source thereof, preferably the test population comprises melanoma, or skin, or eye cells, and/or the test cell population comprises cancer cells, e.g. or thyroid gland, or colon, or lung or ovary cancer cells and/or the test cell population comprises mammalian cells, and/or the test cell population comprises human cells;
(b) contacting the test cell population with the substance;
(c) determining the expression level of said miRNA molecule or equivalent thereof or source thereof or the activity or steady state level of said miRNA molecule or equivalent thereof or source thereof in the test cell population contacted with the substance;
(d) comparing the expression, activity or steady state level determined in (c) with the expression, activity or steady state level of said miRNA molecule or equivalent thereof or source thereof in a test cell population that is not contacted with the substance; and,
(e) identifying a substance that produces a difference in expression level, activity or steady state level of said miRNA molecule or equivalent thereof or source thereof, between the test cell population that is contacted with the substance and the test cell population that is not contacted with the substance.

Preferably, in step a), a test cell comprises a nucleic acid construct comprising a source or a precursor of a miRNA-10b, miRNA-18b, miRNA-96, miRNA-129, miRNA-128, miRNA-184, miRNA-190b, miRNA-203, miRNA-3157, miRNA-133a, miRNA-200c, miRNA-610, miRNA-182, miRNA-16, miRNA-95, miRNA-193a, miRNA-497, miRNA-509 and/or a miRNA-7 molecule or an equivalent thereof or a precursor of said miRNA as identified earlier herein. More preferably, a test cell is A375 as used in the experimental part. Preferably, in a method the expression levels, an activity or steady state levels of more than one nucleotide sequence or more than one miRNA molecule, equivalent or source thereof are compared. Preferably, in a method, a test cell population comprises mammalian cells, more preferably human cells. Alternatively or in addition to previous mentioned cells, in one aspect the invention also pertains to a substance that is identified in the aforementioned methods. A substance tested may be any substance. It may be a miRNA molecule, an equivalent or a source thereof as defined herein.

In a preferred method, the expression levels, activities or steady state levels of at least another one miRNA molecule or equivalent or source thereof is compared, preferably wherein the other miRNA molecule or equivalent or source thereof is selected from:
a) at least one of miRNA-13, Let-7, and Let-7a and/or an equivalent or a source thereof and/or,
b) at least one miRNA-221 and miRNA-222 and/or an equivalent or a source thereof.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are generally transcribed from non-protein-encoding genes. Occasionally, introns of protein coding genes are the source of miRNA transcription. A precursor may have a length of at least 70, 75, 80, 85 nucleotides. The precursor miRNAs have two regions of complementarity that enables them to form a stem-loop- or fold-back-like structure, which is cleaved by enzymes called Dicer and Drosha in animals. Dicer and Drosha are ribonuclease III-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or equivalents or source thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand. Two designs incorporate chemical modifications of the complementary strand. The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others. The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand. Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

MiRNA Libraries

A key application for the miRNAs as identified herein is the assessment or diagnosis of the presence of one individual or groups of miRNAs in a sample. Cell populations with each of the different miRNAs can then be assayed to identify miRNAs whose presence affects a cellular phenotype (i.e. EMT). The number of different miRNAs in the libraries is variable. It is contemplated that there may be, be at least, or be at most 1, 2, 3, 4, 5, 6, 7, 8, 9, 10, 11, 12, 13, 14, 15, 16, 17, 18, 19, 20 or more, or any range derivable therein, different miRNA-specific molecules in the library. In specific embodiments, libraries have 1 to 20 different miRNA-specific molecules, or 5 to 20 different miRNA-specific molecules. "Different" miRNA-specific molecules refers to nucleic acids that specifically encode miRNAs with different sequences.

miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs. Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or equivalent thereof has a sequence that derives from any of SEQ ID NOs: 96-129 (as identified in Table 3) or from any of SEQ ID NO: 191-294 (as identified in Table 6).

A miRNA molecule or equivalent thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

Libraries of the invention can contain miRNA sequences from any organism having miRNAs, specifically including but not limited to, mammals such as humans, non human primates, rats and mice. Specifically contemplated are libraries having, having at least, or having at most 1, 2, 3, 4, 5, 6, 7, 8, 9, 10, 11, 12, 13, 14, 15, 16, 17, 18, 19, 20 or more different miRNAs (that is, miRNA-specific molecules having different sequences derived from different miRNA genes). Specifically contemplated are such libraries described in the previous sentence with respect to any of SEQ ID NOs:96-129, particularly those corresponding to miRNA sequences (mature sequence).

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 2 indicates which SEQ ID NO corresponds to a particular precursor sequence of a miRNA (SEQ ID NO:69-95 and Table 3 which SEQ ID NO corresponds to the mature sequence of a miRNA (SEQ ID NO: 96-129). Table 4 identifies the cloned DNA sequences into the lentiviral vector (SEQ ID NO: 130-156), which were used in the functional screen as described in the examples. Table 5 identifies the preferred seed sequence of each of the mature miRNAs of Table 3 (SEQ ID NO:157-190). Table 6 shows preferred IsomiR equivalents of each of the mature miRNAs identified (SEQ ID NO:191-294). The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below. Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs:63-79 or are described in SEQ ID NO:69-95 or in SEQ ID NO:130-156 or in SEQ ID NO:157-190 or in SEQ ID NO:113-146. It is contemplated that nucleic acids sequences of the invention derived from SEQ ID NO:96-129 can have, have at least, or have at most 5, 6, 7, 8, 9, 10, 11, 12, 13, 14, 15, 16, 17, 18, 19, 20, 21, 22, 23, contiguous nucleotides from SEQ ID NOs:96-129 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs:96-129 or to the precursor sequence of any of SEQ ID NO:69-95 or any combination or range derivable therein.

Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2' and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' NH2, 2'N3,4'thio, or 2' O—CH3) and 2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5'OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acids

A nucleic acid may be made by any technique known to one of ordinary skill in the art, such as for example, chemical synthesis, enzymatic production or biological production. Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. Nos. 4,704,362, 5,221,619, and 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers.

Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, NH2, biotin, an amine group, a lower alkylamine group, an acetyl group, 2' O-Me, DMTO, fluoroscein, a thiol, or acridine or any other group with this type of functionality.

Other sense strand modifications. The introduction of nucleotide modifications like 2'-O Me, 2'-deoxy, T-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), NH2, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell. More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, stem cells, liver, lung, bone, breast, cervix, colon, endometrium, epithelial, esophagus, goblet cells, kidney, ovaries, pancreas, prostate, bladder, skin, small intestine, stomach, testes, heart.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a screening method, or it may be related to a therapeutic or diagnostic application.

RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targetting molecule. A targetting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209). Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S., et al, Trends Mol. Med., (2009), 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonucleotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospholipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic acid to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, *Drosphila antennapedia*, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4',5,5'-hexachlorobiphenyl (Borlakoglu et al, 1990) could enhance cellular uptake, and improve nuclease resistance by promoting lipoprotein association.

Screening with miRNA Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development. In some embodiments, there is a multi-step process for screening, in certain embodiments, there are four general steps:

(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium. Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes.

(2) Optimize Transfection Conditions for the Desired Cells.

The first step in this process is identifying a transfection reagent and plating conditions that maximize the uptake of synthetic miRNAs while maintaining high cell viability. We find it useful to test 2-5 different transfection reagents when using cell lines or 5-10 elelctroporation conditions when using primary or suspension cells. Transfection can be optimized for the reagent or electroporation condition that worked best among the conditions tested. Screening miRNA-specific libraries requires conditions for high-throughput transfection.

(3) Screen

Once the assay and transfection process have been developed, a library of synthetic miRNAs or miRNAs expressed by viruses can be introduced sequentially into cells in a 24- or 96-well plate. Triplicate transfections for each reagent provide enough data for reasonable statistical analysis.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed.

Labeling and Labeling Techniques

In some embodiments, the present invention concerns miRNAs that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNAs may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and NEN. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$-[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N-(4-amino)butyl-dATP, $N^6$-(6-amino)butyl-dATP, $N^4$-[2,2-oxy-to-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled, in embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNAs is how to label the already existing molecule. To this end, we may use an enzyme capable of using a di- or tri-phosphate ribonucleotide or deoxyribonucleotide as a substrate for its addition to an miRNA, a small RNA molecule. Moreover, in specific embodiments, it involves using a modified di- or triphosphate ribonucleotide, which is added to the 3' end of an miRNA. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed. Poly(A) polymerase has been cloned from a number of organisms from plants to humans. It has been shown to catalyze the addition of homopolymer tracts to RNA (Martin et al, RNA, 4(2):226-30, 1998). Terminal transferase catalyzes the addition of nucleotides to the 3' terminus of a nucleic acid. Polynucleotide phosphorylase can polymerize nucleotide diphosphates without the need for a primer.

Labels and Tags miRNAs or miRNA probes may be labeled with a positron emitting (including radioactive), enzymatic, colorimetric (includes visible and UV spectrum, including fluorescent), luminescent or other label or tag for detection or isolation purposes. The label may be detected directly or indirectly. Radioactive labels include $^{125}I$, $^{32}P$, $^{33}P$, and $^{35}S$. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, AMCA, Alexa Fluor dyes, BODIPY dyes, such as BODIPY FL, BODIPY 630/650, BODIPY 650/665, BODIP Y-R6G, BODIPY-TRX; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODEPY 530/550, BODEPY 558/568, BODIPY 564/570, BODDPY 576/589, BODIPY 581/591, BODEPY 630/650, BODIPY 650/655, BODIPY FL, BODIPY R6G, BODEPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODEPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP. Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODEPY FL-14-dUTP, Rhodamine Green-5-dUTP, Alexa Fluor 532-5-dUTP, BODEPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODEPY TR-14-dUTP, Alexa Fluor 594-5-dUTP, BODEPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. It is contemplated that nucleic acids may be labeled with two different labels.

It is contemplated that synthetic miRNAs may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference). Fluorescent energy transfer dyes, such as thiazole orange-ethidium heterodimer; and, TOTAB may be used.

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al, 1997, spectroscopy, capillary gel electrophoresis (Cummins et ah, 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule.

Array Preparation

The present invention can be employed with miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference. It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments, hi certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$. Moreover, a person of ordinary skill in the art could readily analyze data generated using an array. Such protocols are disclosed above, and include information found in WO 9743450; WO 03023058; WO 03022421; WO 03029485; WO03067217; WO 03066906; WO 03076928; WO 03093810; WO 03100448A1, all of which are specifically incorporated by reference.

Sample Preparation

It is contemplated that the miRNA of a wide variety of samples can be analyzed using assays described herein. While endogenous miRNA is contemplated for use with some embodiments, recombinant miRNA—including nucleic acids that are identical to endogenous miRNA or precursor miRNA—can also be handled and analyzed as described herein. Samples may be biological samples, in which case, they can be from blood, tissue, organs, semen, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

Cell Assays to Identify miRNAs with Ties to Disease

Specifically contemplated applications include identifying miRNAs that contribute to a melanoma that are themselves parts of a disease or conditions or might otherwise be associated with a particular disease state. Additionally, a contemplated application includes the identification of miRNAs that are able to treat, prevent, cure a melanoma or a condition associated thereof. Also, miRNA functions may be compared between a sample believed to be susceptible to a particular disease or condition associated with melanoma or a disease or condition associated with activated BRAF pathway and one believed to be not susceptible or resistant to that disease or condition. It is specifically contemplated that RNA molecules of the present invention can be used to treat any of the diseases or conditions discussed in the previous section or modulate any of the cellular pathways discussed in the previous section. Specifically contemplated applications include identifying miRNAs that contribute to a cellular process associated with melanoma such as the BRAF-MEK-ERK pathway that are themselves parts of a disease or might otherwise be associated with a particular disease state. Also, miRNA functions may be compared between a sample believed to be susceptible to a particular disease or condition associated with a melanoma and one believed to be not susceptible or resistant to that disease or condition.

The efficacy of different therapeutic drugs is altered by miRNAs according to the present invention. Moreover, it has been described that tumor cells with BRAF mutations may become resistant to chemo- and immunotherapy (Abrams S. L. et al., Cell cycle 9:1781, 2010, McCubrey J. A. et al., Adv. Enzyme Regul. 46: 249, 2006). Therefore, miRNA based drugs that affect the active BRAF pathway may enhance susceptibility to e.g. chemo- and immunotherapy. Such therapeutic drugs include, but are not limited to, chemotherapeutic drugs. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma and calicheamicin omega); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholmo-doxorubicm, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-II); topoisomerase inhibitor RFS 2000; difluorometlhylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LY1 17018, onapristone, and toremifene; aromatase inhibitors that inhibit the enzyme aromatase, which regulates estrogen production in the adrenal glands, such as, for example, 4(5)-imidazoles, aminoglutethimide, megestrol acetate, exemestane, formestanie, fadrozole, vorozole, letrozole, and anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-α, Raf and H-Ras; ribozymes such as a VEGF expression inhibitor and a HER2 expression inhibitor; vaccines such as gene therapy vaccines and pharmaceutically acceptable salts, acids or derivatives of any of the above. A list of U.S. FDA approved oncology drags with their approved indications can be found on the World Wide Web at accessdata.fda.gov/scripts/cder/onctools/druglist.cfm. Moreover, it is contemplated that samples that have differences in the activity of certain pathways may also be compared. Such cellular pathways include but are not limited to the following: any adhesion or motility pathway including but not limited to those involving cyclic AMP, protein kinase A, G-protein couple receptors, adenylyl cyclase, L-selectin, E-selectin, PECAM, VCAM-I, α-actinin, paxillin, cadherins, AKT, integrin-α, integrin-β, RAF-I, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, Rho A, Rac, myosin light chain kinase, platelet-derived growth factor receptor or ezrin; any apoptosis pathway including but not limited to those involving AKT, Fas ligand, NFKB, caspase-9, PB kinase, caspase-3, caspase-7, ICAD, CAD, EndoG, Granzyme B, Bad, Bax, Bid, Bak, APAF-I, cytochrome C, p53, ATM, Bcl-2, PARP, Chk1, Chk2, Rho-21, c-Jun, Rho73, Rad51, Mdm2, Rad50, c-Abl, BRCA-I, perforin, caspase-4, caspase-8, caspase-6, caspase-1, caspase-2, caspase-10, Rho, Jun kinase, Jun kinase kinase, Rip2, lamin-A, lamin-B1, Lamin-B2, Fas receptor, H2O2, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RTP, cyclin-D1, PCNA, BcI-XL, PIP2, PIP3, PTEN, ATM, Cdc2, protein kinase C, calcineurin, IKKα, IKKβ, IKKγ, SOS-I, c-FOS, Traf-1, Traf-2, IκBβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p34, p20, PP2A, angiotensin, angiotensin-converting enzyme, protease-activated receptor-1, protease-activated receptor-4, Ras, RAF-I, PLCβ, PLCγ, COX-I, G-protein-coupled receptors, phospholipase A2, IP3, SUMOI, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCC1, CD40, CD40 ligand, p38, DCKα, IKKβ, NFKB, TRAF2, TRAF3, TRAF5, TRAF6, IL-4, IL-4 receptor, CDK5, AP-I transcription factor, CD45, CD4, T cell receptors, MAP kinase, nerve growth factor, nerve growth factor receptor, c-Jun, c-Fos, Jun kinase, GRB2, SOS-I, ERK-I, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p27, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-I, BRCA-2, SKP1, the proteasome, CUL1, E2F, pi 07, steroid hormones, steroid hormone receptors, IκBα, IκBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCCl, Sonic Hedgehog, Crml, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, 1 KB, NFKB, RACl, RAFl, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-I receptor, the urea cycle, vesicular transport, or salvage pathways. It is further contemplated that nucleic acids molecules of the invention can be employed in diagnostic and therapeutic methods with respect to any of the above pathways or factors. Thus, in some embodiments of the invention, a miRNA inhibits, eliminate, activates, induces, increases, or otherwise modulates one or more of the above pathways or factors is contemplated as part of methods of the invention. The nucleic acid can be used to diagnosis a disease or condition based on the relation of that miRNA to any of the pathways described above.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic and Diagnostic Applications miRNAs that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with a melanoma as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention.

Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen. For topical administration the proteins of the invention may be formulated as solutions, gels, ointments, creams, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed. Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organelles by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin A5 (targeting phophatidylserine exposing membranes, Gamier B. et al., Biocon-jug Chem., 2009, 11:2114-22), WO 2009/126933 describing compositions and methods for site-specific delivery of nucleic acids by combining them with targeting ligands and endosomolytic components. Targeting ligands that are preferentially suitable are tumor associated cell surface proteins, more preferably prostate tumor associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The chimeric molecules may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. 1, p. 1).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-ammoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe (II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Kits

Any of the compositions described herein may be comprised in a kit. In a non-limiting example, individual miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the miRNA to cells.

In another non-limiting example, multiple synthetic miRNAs are included in a kit. The kit may further include one or more negative control synthetic miRNAs that can be used to control for the effects of synthetic miRNA delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: miRNA, library of miRNAs, combination library of miRNA, negative control miRNA, nuclease-free water; RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA, an equivalent, a mimic, an isomiR or an antagomir or a source thereof or a composition as defined herein may comprise additional component(s) than the ones specifically identified, said additional component(s) not altering the unique characteristic of the invention. In addition the verb "to consist" may be replaced by "to consist essentially of" meaning that a method as defined herein may comprise additional step(s) than the ones specifically identified, said additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

In total 1120 viral preparations each containing an individual miRNA construct were screened at a predetermined volume amount of virus stock solution. Data analysis was done on absolute values to get a Z-score obtained through statistical methods 1-4. MiRNAs that were below (Z score<−2) or above (Z score>2) a predetermined threshold were selected as hit, Only a small population of miRNAs was below or above this threshold. Negative controls (closed triangles and diamonds) were around the median, whereas the positive control shRNA for BRAF was always below the threshold (Z score<−2). A representative example of such an analysis is shown for a selection (2 plates, miRNAs from $1^{st}$ plate represented by open triangles, miRNAs from $2^{nd}$ plate represented by open diamonds) of viral solutions containing miRNAs. This graph demonstrates the fact that the majority of miRNAs do not have any effect on cell growth. MiRNAs on these plates that affected cell growth have been indicated (miR-129-2, miR-184 and miR-203).

FIG. 2

A375 melanoma cells were infected with a selection of virus containing miRNAs at a predetermined volume amount of virus stock solution (MOI differs per viral stock solution, as indicated in the graph on the x-axe), in addition to viruses with a predetermined MOI (MOI of 100 and 200). Inhibition of cell viability (as shown on the y-axe) was calculated compared to a control population of several empty vector constructs. Most selected miRNAs show a trend towards dose-dependency.

FIG. 3

The effect of miR-203 on cell growth was validated using a mature miRNA mimic at several concentrations in the same cell growth assay (MTS). Inhibition of cell viability was calculated against mimic controls. Positive control shRNA for BRAF and mir-203 show a strong inhibition of cell viability, with a tendency towards dose dependency.

FIG. 4

Figure 4A:
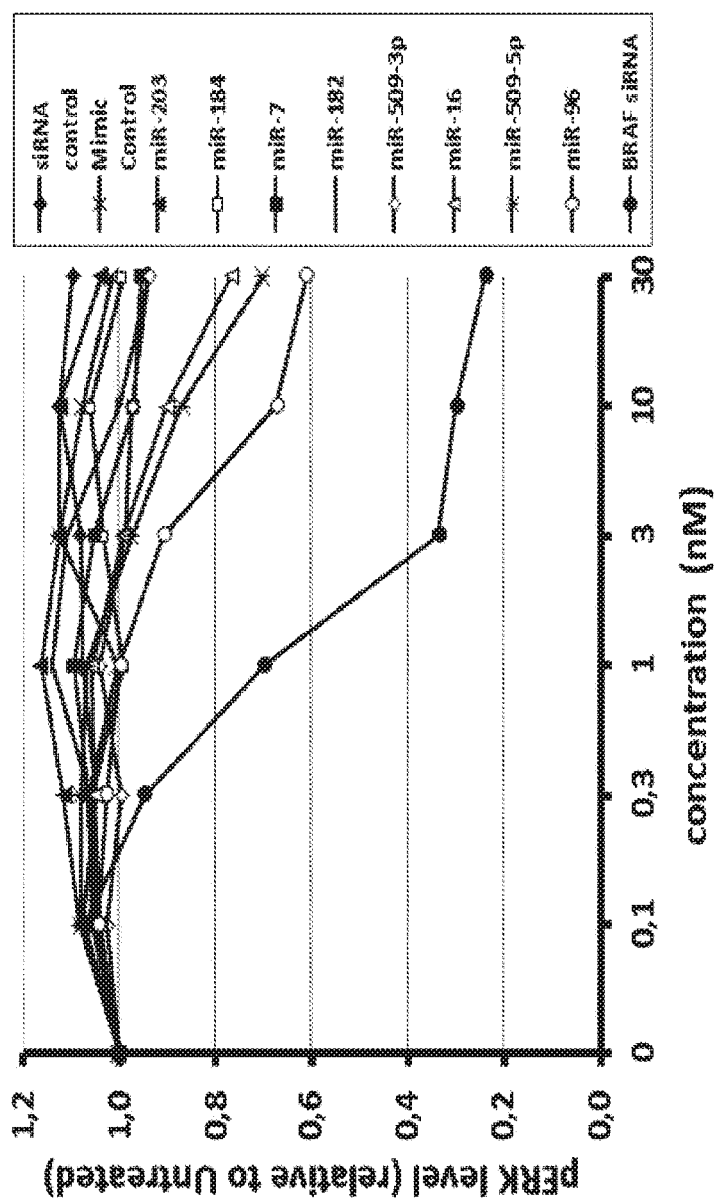
Figure 4B:
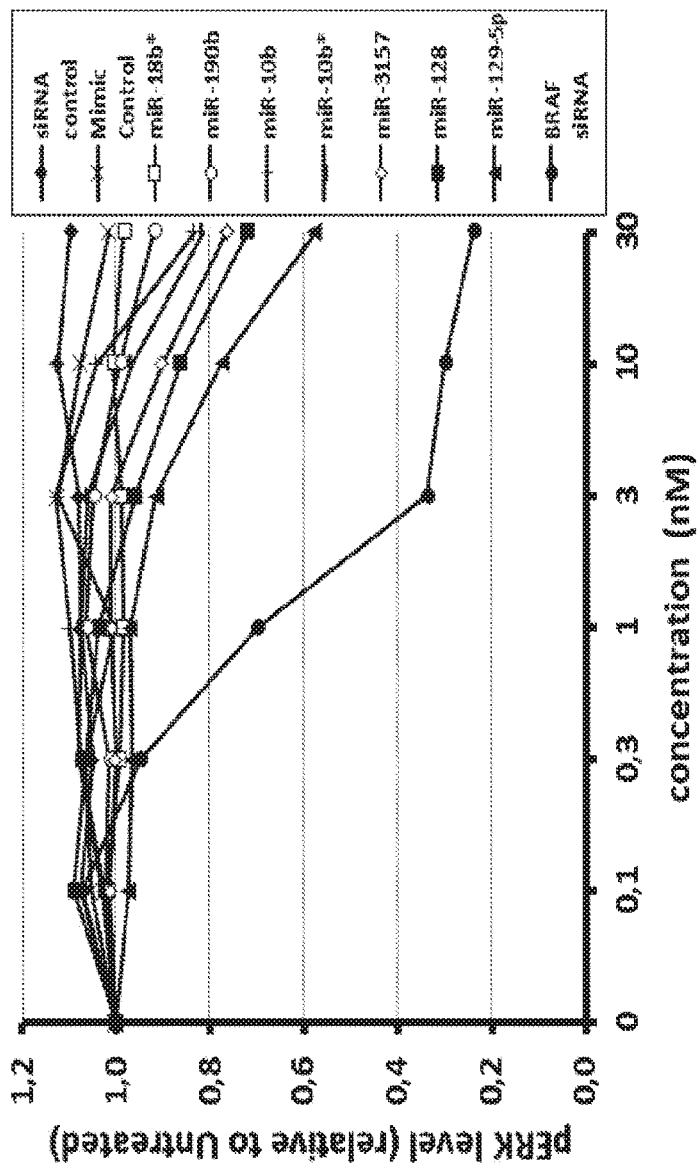

FIGS. 4A-4B: Effect of overexpression of the specified miRNA mimics on pERK levels in the melanoma cell line A375 (from the Hubrecht laboratory) detected by ELISA. The BRAF-specific siRNA was included as positive control. The order of the mimics/siRNAs is according to their effect on pERK levels.

FIG. 5

Western blot analysis of BRAF and pERK levels after transfection of the melanoma cell line A375 (from the Hubrecht laboratory or from the ATCC (CRL-1619™)), with the indicated miRNAs. A375 cells were transfected with 100 nM miRNA in 6-well plates. Proteins were isolated three days after transfection. The BRAF siRNA was included as positive control and tubulin was used as loading control.

FIG. 6

Western blot analysis of BRAF and pERK levels after transfection of the melanoma cell line SKMEL-28 with miR-129, miR-509-5p or controls. SKMEL-28 cells were transfected with 100 nM miRNA in 6-well plates. Proteins were isolated three days after transfection. The BRAF siRNA was included as positive control and tubulin was used as loading control.

EXAMPLE 1

Material and Methods
Generation of the Lentiviral Library Encoding miRNAs

Human miRNAs were selected from both the public miRNA repository (www.mirbase.org) and proprietary small RNA deep sequencing data (see WO 2007/081204). The miRNA sequences were amplified from their genomic location with amplicons containing the full-length pre-miRNA hairpin and a flanking sequence on both sides of 50-150 basepairs. The primers for the amplicons were designed using Primer3 software (www.geneious.com). If the primer design program could not find appropriate primers in the designated sequences, the requirements for the flanking sequences were adjusted to 0-200 basepairs. The designed primers were complemented with a 5' GCGC overhang and a restriction site for directional cloning. As default the primer upstream of the miRNA was complemented with a BamHI restriction site (GGATCC) and the primer downstream of the miRNA was complemented with an EcoRI restriction site (GAATTC). Primers of amplicons with internal BamHI or EcoRI restriction sites (i.e. occurring in the genomic sequence) were complemented with either a BglII site (AGATCT) or a XbaI site (TCTAGA) respectively. The miRNAs were amplified using the abovementioned primers from human genomic DNA of a single individual in the following PCR reaction:

| constituent | concentration | volume | supplier/cat # |
| --- | --- | --- | --- |
| buffer | 10X | 1 µl | Stratagene/600159 |
| dNTPs | 10 mM each | 0.2 µl | GE Healthcare/27-18(5-8)0-04 |
| fwd primer | 10 uM | 0.2 µl | IDT (Integrated DNA Technologies) |
| rev primer | 10 uM | 0.2 µl | IDT (Integrated DNA Technologies) |
| gDNA | 100 ng/µl | 0.1 µl | private source |
| Pfu DNA pol | 2.5 U/µl | 0.1 µl | Stratagene/600159 |
| H$_2$O | N/A | 8.2 µl | N/A |

| temp (° C.) | time | cycles |
| --- | --- | --- |
| 95 | 2 min | |
| 95 | 15 s | 40 |
| 59* | 15 s | 40 |
| 72 | 90 s | 40 |
| 72 | 15 min | |
| 4 | ∞ | |

*−0.1° C./cycle

All miRNA loci were amplified in separate 10 µl PCR reactions. The products were purified using the Qiagen PCR Clean-Up buffer set and Whatman Unifilter GF/C filter plates (cat #7700-1101). DNA was eluted with 17 µl H$_2$O per well. The separate eluates were used in the following restriction reaction:

| constituent | concentration | volume | supplier/cat # |
| --- | --- | --- | --- |
| buffer E | 10X | 2 µl | Promega/R005A |
| EcoRI* | 12 U/µl | 0.1 µl | Promega/R6017 |
| BamHI* | 10 U/µl | 0.1 µl | Promega/R6025 |
| eluate | N/A | 16 µl | N/A |
| H$_2$O | N/A | 1.8 µl | N/A |

*Amplicons with internal restriction sites for EcoRI or BamHI were cut with XbaI or BglII respectively instead. The EcoRI + BglII reaction was done with Promega buffer D. The BamHI + XbaI reaction was done with Promega buffer E.

Restriction for 2 hours at 37° C. The separate 20 µl restriction reactions were purified using the Qiagen PCR Clean-Up buffer set and Whatman Unifilter GF/C filter plates (cat #7700-1101). DNA was eluted with 20 µl H$_2$O per well. The separate eluates were used in the following ligation reaction:

| constituent | concentration | volume | supplier/cat # |
| --- | --- | --- | --- |
| buffer | 10X | 2 µl | Promega/C1263 |
| T4 DNA ligase | 1-3 U/µl | 0.2 µl | Promega/M1804 |
| Crestricted pCDH* | 1 ng/µl | 7.8 µl | System Biosciences/CD510B-1 |
| eluate | N/A | 10 µl | N/A |

Ligation overnight at 4° C.
*For directional cloning, pCDH was cut with both EcoRI and BamHI. An alternate construct called pCDH- was made with reversed EcoRI and BamHI restriction sites so that the amplicons with 5' BamHI and 3' EcoRI were cloned in the proper direction. The amplicons with an internal EcoRI site were cut with XbaI and ligated into a pCDH vector that was restricted with XbaI and BamHI.

The resulting ligates were transformed separately into bacteria (Promega Single Step (KRX) competent cells, cat # L3002). 50 µl competent cells was diluted with 950 µl transformation buffer II (10 mM MOPS, 75 mM CaCl$_2$, 10 mM RbCl, 15% glycerol, filter-sterilized). Per 20 µl ligate 20 µl diluted competent cells was added. The mix was incubated for 15 minutes on ice, heat-shocked at 37° C. for 30 seconds, and put back on ice. After 2 minutes the transformed bacteria were reconstituted in 150 µl lysogeny broth (LB). The bacteria were allowed to recover for 20 minutes at 37° C. after which they were plated out separately on ampicillin-containing (50 ug/mL) LB-agar plates and grown overnight at 37° C.

Single colonies of each plate are picked and subcultured overnight in 400 µl ampicillin-containing (50 ug/mL) LB. 1 µl of subculture is lysed in 100 µl water for sequencing purposes. Bacterial lysate is used in the following PCR reaction:

| constituent | concentration | volume | supplier/cat # |
|---|---|---|---|
| buffer | 5X | 1 µl | private source |
| dNTPs | 10 mM each | 0.1 µl | GE Healthcare/27-18(5-8)0-04 |
| pCDH-fwd | 10 uM | 0.1 µl | IDT (Integrated DNA Technologies) |
| pCDH-rev | 10 uM | 0.1 µl | IDT (Integrated DNA Technologies) |
| lysate | 1:100 | 1 µl | N/A |
| Taq DNA pol | unknown | 0.02 µl | private source |
| H$_2$O | N/A | 2.68 µl | N/A |

| temp (° C.) | time | cycles |
|---|---|---|
| 95 | 2 min | |
| 95 | 15 s | 40 |
| 59* | 15 s | 40 |
| 72 | 90 s | 40 |
| 72 | 15 min | |
| 4 | ∞ | |
| pCDH-fwd | CACGCTGTTTTGACCTCCATAGA | |
| pCDH-rev | CACTGACGGGCACCGGAG | |
| (SEQ ID NOs: 1 and 2) | | |

*-0.1° C./cycle

The PCR products were diluted 25x. 1 µl of diluted PCR product was used in the following Sanger Sequencing reaction:

| constituent | concentration | volume | supplier/cat # |
|---|---|---|---|
| buffer | N/A | 1.9 µl | private source |
| BigDye v3.1 | N/A | 0.1 µl | ABI/4336921 |
| pCDH-seq | 10 um | 0.1 µl | IDT (Integrated DNA Technologies) |
| PCR product | 1:25 | 1 µl | N/A |
| H$_2$O | N/A | 1.9 µl | N/A |

| temp (° C.) | time | cycles |
|---|---|---|
| 94 | 10 sec | |
| 50 | 5 s | 40 |
| 60 | 2 min | 40 |
| 10 | ∞ | |
| pCDH-seq | GACCTCCATAGAAGATTCTAGAGCTAGC | |
| (SEQ ID NO: 3) | | |

30 µl precipitation mix (80% ethanol, 50 mM sodium acetate pH 5.5) was added to each of the sequencing reaction products. The mixes were vortexed for 10 seconds and spun down at 5000 rcf for 45 minutes at 4° C. Supernatant was aspirated and DNA pellets were washed with 30 µl ice cold 80% ethanol and spun at 5000 rcf for 5 minutes at 4° C. Supernatant was aspirated and the DNA pellet was dried on a heat block for 10 minutes. The dry DNA pellet was dissolved in 10 µl H$_2$O. The resulting DNA solution was sequenced on an ABI 3730XL DNA Analyzer. Sequences were compared to the expected genomic sequences. Correct clones were added to the library. For incorrect clones an additional 4 bacterial colonies were picked, and analyzed for insert sequence.

Library constructs were subcultured overnight in 50 mL ampicillin-containing (100 ug/mL) LB and isolated with the Qiagen QIAfilter Plasmid Midi Kit (cat #12245) supplemented with the Qiagen EndoFree Plasmid Buffer Set (cat #19048) according to the instructions of the manufacturer. DNA was dissolved in the supplied TE buffer and brought to a final concentration of 500 ng/µl.

We ordered constructs that we were not able to clone ourselves as minigenes from Integrated DNA Technologies. In these cases, the full-length hairpin plus 20 basepairs flanking each site were cloned into our vector as a service by IDT.

Packaging and virus production was performed by System Biosciences as described in the user manual of CD-500B1-CD523-A1.

Cell Culture

A375 cells were cultured in DMEM Glutamax (Invitrogen, 31966), supplemented with essential amino acids (Invitrogen, 11140) and 10% Fetal Bovine Serum (Sigma, F7524). Cells were maintained in an incubator at 37° C., 5% CO2. Cells were split twice a week (1:8-1:10).

Chemicals

Polybrene (2 µg/ml; Sigma, H9268) was used to increase the efficiency of infection with the miRNA-encoding lentiviral particles.

As positive technical control a shRNA sequence against BRAF was obtained (Sharma et al. Cancer Res 2006) and ordered from IDT as oligo. The oligo was cloned and packaged as described for miRNA constructs.

Viral Transduction and Screening

Day 0

A375 cells were plated at a density of 1000 cells per well of a 96 well plate in 100 µl DMEM containing 5% FCS.

Packaged lentiviral constructs were stored at −80° C. as frozen VSV-G pseudotyped viral particles in 96 well plates, where each well contained an individual miRNA. The viral plates were thawed and resuspended. 95 µl PBS-Polybrene mastermix was prepared in a separate 96 well plate at a concentration of 60 µg/mL. 5 µl virus was added to the mastermix.

Viral transduction was performed in duplicate 4 hours after plating of the cells by adding 10 µl of virus/polybrene mix to each well. Per well, this accomplished a final concentration of 5.5 µg/mL Polybrene and 0.5 µl virus. The plates were rocked gently to evenly distribute the virus in each well.

Day 1

Medium was completely aspirated and replaced with 150 µl fresh DMEM 5% FCS.

Day 5

100 µl medium was aspirated and replaced with 100 µl fresh DMEM 5% FCS.

Day 6

For the Hoechst assay (Sigma, B2261), plates were fixated by adding 100 µl of 8% PFA solution (Sigma, 16005) to each well. After 20 minutes, plates were aspirated and 150 µl PBS was added. Plates were stored at 4° C.

For Hoechst staining the plates were completely aspirated and 50 µl of working solution was added and incubated for 20 minutes. The Hoechst solution was completely aspirated and replaced with 150 µl PBS. Plates were stored at 4° C. until measurement with the Cellomics® ArrayScan® VTI (Thermo Scientific) could be performed.

For the MTS assay (MTS CellTiter 96® AQueous One Solution Cell Proliferation Assay, Promega, G3582) the plates were completely aspirated and 100 µl fresh 5% FCS DMEM was added after which immediately 30 µl of MTS solution was added. After 3, 4 and 5 hours incubation at 37° C., absorbance was measured at 492 nm with the FC Multiskan absorbance reader (Thermo Scientific).

Hit Selection

To select miRNAs that affect cell growth, the Z-score was chosen. To evaluate the normal distribution per plate and of combined plates, a distribution plot was made with the calculated median and standard deviation and with the actual values.

Several methods to calculate the Z-score were evaluated with different cut-offs. The standard Z-score uses the mean and the SD of the population and the Robust Z-score uses the median and instead of the SD the median absolute deviation (MAD) multiplied with a given number (1.48) to simulate a normal population (Chung N. et al., J Biomol Screen 13:149-58, 2008).

For the MTS assay the duplicate correlation was good enough to calculate the average per well. For the Hoechst the duplicates were considered separately.

Method 1:

The individual miRNA Robust Z-score was calculated per plate.

Method 2:

The individual miRNA Z-score was calculated per experimental day using all the read-out values of each miRNA.

Method 3:

The data was transformed making one plate by combining the values per well of all individual plates per day. The individual miRNA Z-score was calculated per experimental day using the median and SD of the combined plate.

Method 4:

MAD-scores (Hoechst and MTS) were calculated for each measurement and the ratio. These scores were calculated against the plate median of that particular variable. The MAD-scores are transformed to a probability score using a normal distribution graph. The probabilities of the duplicates are multiplied and then corrected if they lie far apart by dividing with the probability score of the standard deviation between the two.

The abovementioned methods were used to select the significant inhibitors and significant stimulators for the MTS screen. The hits for each method were given a rank score to represent hit strength and the rank sum was used to combine the four methods.

Eventually, 56 miRNAs that are able to inhibit cell growth most effectively were chosen from the MTS screen and supplemented with 7 hits as selected from the Hoechst screen.

In addition, 26 of the strongest stimulators were chosen from the MTS screen, supplemented with 4 hits from the Hoechst screen.

Hit Confirmation

For confirmation of the above selected hits, several steps were taken. The first step contained a rescreen of the selected hits, using the viral stocks without normalization for viral titer.

All miRNAs, empty vector virus samples and shRNA BRAF control were combined into two plates. The edges of the plates were filled with medium only to minimize evaporation artifacts. An additional control plate with empty vectors and 24 miRNA which previously showed no effect in the MTS screen. The control plate was used to determine the difference between an empty vector control population and a miRNA control population.

The second step in confirmation of the selected hits concerned a rescreen of the selected miRNAs at a predetermined MOI of 100 and 200. This was done to exclude viral toxicity or dose-dependent effects of individual miRNAs. A master dilution plate was made with PBS to dilute each individual construct to a titer of 1×10E8 infectious units (IFU) per mL.

All miRNAs, empty vector virus samples and shRNA BRAF control were combined into two plates. Edges were filled with medium only to minimize evaporation artifacts. The control plate from confirmation 1 was used to calculate the mean, median, SD and MAD for the (Robust) Z-score.

Viral transduction was done for the MTS assay as described in duplicate with 2 µl diluted virus for a MOI of 200 and with 1 µl diluted virus for a MOI of 100.

Statistical analysis was done using the miRNA control population, the empty vector control population and the standard and Robust Z-score from this and from previous experiments.

Total RNA Isolation

A375 cells were seeded in a 24-well plate and were transduced at a MOI of 30 according to previous transduction protocols. At day 6 cells, cells were washed with ice cold PBS, 1 ml of PBS was added and the plate was put on ice. Cells were collected using a cell scraper and pipetted in an eppendorf tube. Cells were pelleted, PBS was aspirated and cells were frozen at −80° C.

For RNA isolation, cells were thawed on ice, 200 µl Trizol (Invitrogen) was added followed by a 5 minute incubation at room temperature. 40 µl chloroform was added and tubes were shaken and incubated for 3 minutes. Samples were centrifuged at 12000×g for 15 minutes at 4° C. and two thirds of the upper aqueous layer was transferred to a non-stick RNAse free tube. The remaining aqueous layer was transferred to a different tube as back up.

1 µl of Glycoblue (Applied Biosystems, AM9510) was added to all samples together with 100 µl RNAse free iso-propanol and the RNA was precipitated at −20° C. overnight for the first batch and for two weeks for the backup batch. Samples were centrifuged at max speed for minimally 45 minutes at 4° C. and the pellet was washed with 200 µl 70% RNAse free ethanol. Samples were centrifuged at 7400×g for 5 minutes at 4° C. and supernatant was removed. The pellet was dried and dissolved in 25 μl H₂O for the first batch and 15 μl DEPC treated H₂O for the backup batch.

The RNA kit for the Qubit (Invitrogen) was used according to protocol to measure the final RNA concentration.

Stem-Loop RT-PCR

MicroRNA expression was determined by stem-loop RT-PCR as described (Chen, C. et al Nucleic Acids Res. 33: e179 (2005). For the stem loop RT-PCR, stem loop primers were designed for each individual miRNA according to the mature sequences in mirBase 15 and an isoform thereof and for a household gene, U6: For the qPCR individual forward primers were designed according to the mature miRNA sequence in mirBase 15 (Seq ID NOs: 4-35). The universal reverse primer was designed for the stem-loop sequence (SEQ ID NO: 58).

MiR-7-3:
SL-primer:
5'-GTCGTATCCAGTGCAGGGTCCGAGGTATTCGCACTGGATACGAACAACA-3'

Forward primer:
5'-GCCCGCTTGGAAGACTAGTGATTTTG-3'

MiR-10b:
SL-primer:
5'-GTCGTATCCAGTGCAGGGTCCGAGGTATTCGCACTGGATACGACACAAA-3'

Forward primer:
5'-GCCCGCTTACCCTGTAGAACCGAATT-3'

MiR-10b_star sequence:
SL-primer:
5'-GTCGTATCCAGTGCAGGGTCCGAGGTATTCGCACTGGATACGAATTCCC-3'

Forward primer:
5'-GCCCGCTACAGATTCGATTCTAGGG-3'

MiR-18b:
SL-primer:
5'-GTCGTATCCAGTGCAGGGTCCGAGGTATTCGCACTGGATACGACTAACT-3'

Forward primer:
5'-GCCCGCTTAAGGTGCATCTAGTGCAG-3'

MiR-18b_star sequence:
SL-primer:
5'-GTCGTATCCAGTGCAGGGTCCGAGGTATTCGCACTGGATACGAGCCAGA-3'

Forward primer:
5'-GCCCGCTTGCCCTAAATGCCCCTTC-3'

MiR-96
SL-primer:
5'-GTCGTATCCAGTGCAGGGTCCGAGGTATTCGCACTGGATACGAAGCAAA-3'

Forward primer:
5'-GCCCGCTTTTGGCACTAGCACATTTT-3'

MiR-96_isoform:
SL-primer:
5'-GTCGTATCCAGTGCAGGGTCCGAGGTAATTCGCACTGGATACGACCAAAAA-3'

Forward primer:
5'-TGCCAGTTTGGCACTAGCACATT-3'

MiR-128-1:
SL-primer:
5'-GTCGTATCCAGTGCAGGGTCCGAGGTATTCGCACTGGATACGAAAAGA-3'

Forward primer:
5'-GCCCGCTTCACAGTGAACCGGTCT-3'

MiR-128-1_isoform:
SL-primer:
5'-GTCGTATCCAGTGCAGGGTCCGAGGTAATTCGCACTGGATACGACGAAAGA-3'

Forward primer:
5'-TGCCAGTCACAGTGAACCGGTCTC-3'

MiR-128-2:
SL-primer:
5'-GTCGTATCCAGTGCAGGGTCCGAGGTATTCGCACTGGATACGAAAAGA-3'

Forward primer:
5'-GCCCGCTTCACAGTGAACCGGTCT-3'

MiR-128-2_isoform:
SL-primer:
5'-GTCGTATCCAGTGCAGGGTCCGAGGTAATTCGCACTGGATACGACAAGAGA-3'

Forward primer:
5'-TGCCAGTCACAGTGAACCGGTC-3'

MiR-129-2-5p:
SL-primer:
5'-GTCGTATCCAGTGCAGGGTCCGAGGTATTCGCACTGGATACGAGCAAGC-3'

Forward primer:
5'-TGCCAGCTTTTTGCGGTCTGGGC-3'

MiR-184:
SL-primer:
5'-GTCGTATCCAGTGCAGGGTCCGAGGTATTCGCACTGGATACGAACCCTT-3'

Forward primer:
5'-GCCCGCTTGGACGGAGAACTGATAA-3'

MiR-190b:
SL-primer:
5'-GTCGTATCCAGTGCAGGGTCCGAGGTATTCGCACTGGATACGAAACCCA-3'

Forward primer:
5'-GCCCGCTTGATATGTTTGATATTG-3'

MiR-203:
SL-primer:
5'-GTCGTATCCAGTGCAGGGTCCGAGGTATTCGCACTGGATACGACTAGTG-3'

Forward primer:
5'-GCCCGCTGTGAAATGTTTAGGACCA-3'

MiR-3157:
SL-primer:
5'-GTCGTATCCAGTGCAGGGTCCGAGGTAATTCGCACTGGATACGACA

```
-continued

GACTG-3'

Forward primer:
5'-TGCCAGTTCAGCCAGGCTAGTGCA-3'

A universal reverse primer was used:
5'-GTGCAGGGTCCGAGGT-3'

U6:
                                    (SEQ ID NOs: 59-61)
RT primer:
5'-GTCATCCTTGCGCAGG-3' forward
5'-CGCTTCGGCAGCACATATAC-3' reverse
5'-AGGGGCCATGCTAATCTTCT-3'
```

For the RT reaction 100 ng of RNA sample was used in a reaction with 0.375 pmol SL-RT primer, 5×RT Buffer (Promega M1705), 0.25 mM dNTPs (Promega U1240), 25 units of SuperScript II Reverse Transcriptase (Promega M1705), 1.88 units of RNasin (Promega N2611) and $H_2O$. The PCR was conducted for 30 min at 16° C., 30 min at 42° C. and 5 min at 85° C.

qPCR

To determine the presence of the mature form of the transduced miRNA, a quantitative RT-PCR was performed. For the qPCR individual forward primers were designed according to the mature miRNA sequence in mirBase 15 (Seq ID NOs: 4-35). The reverse primer was designed for the stem-loop sequence (SEQ ID NO:58).

For the qPCR 1 μl of RT-PCR product was used in a reaction with 25 pmol forward en reverse primer, $H_2O$ and 2×iQ SYBR Green supermix (Bio-rad, 170-8880).

PCR reaction was done on a BioRad CFX96 with a initial 5 minute step of 95° C., 45 cycli of 10 seconds 95° C., 20 seconds 60° C. and 10 seconds 72° C., after which a melting curve analysis was preformed. Relative miR expression levels were calculated according to the model described by. CT values for miRNA induced and empty vector samples were obtained and the corresponding U6 CT value was subtracted. The difference between empty vector miRNA levels and miRNA levels in transduced samples were calculated as a measure for overexpression.

DNA Sequence Analysis

The sequence of the cloned miRNAs in the lentiviral vectors for the hits as described in Table 1 was verified as follows. Proviral DNA was amplified by PCR on the fraction of genomic DNA in the RNA samples, using 1 μl RNA sample as input, and pCDH lentiviral vector-specific primers (forward: 5'-CACGCTGTTTTGACCTCCATAGA-3', reverse: 5'-CACTGACGGGCACCGGAG-3', (SEQ ID NO's: 62-63)) for 30 cycles at an annealing temperature of 58° C. DNA sequence analysis was performed using 01-1 μl of PCR product, 0.5 μl of 10 uM pCDH-specific primer (5'-GACCTCCATAGAAGATTCTAGAGCTAGC-3', (SEQ ID NO: 3)), and the Big Dye v3.1 kit (Applied Biosystems). Products were analyzed on a 3730 DNA Analyzers (Applied Biosystems). Data were collected using the Collection Software v3.0 and analyzed using the Sequencing Analysis v5.3.1 program (Applied Biosystems). The sequence for all cloned miRNAs was correct and is given in Table 4.

Synthetic Mimic Transfection

To validate the selected miRNAs, transfection using a synthetic mimic was performed using Lipofectamine RNAiMAX (Invitrogen, 13778150) according to manufacturers protocol (0.1 μl lipofectamine for each 96-well). Mimics (miRIDIAN) and siRNA's (ON-TARGETplus SMARTpool) with available controls were ordered from Dharmacon and tested at different concentrations. Cell viability was determined with the MTS assay as described above.

Results

Figure 1:
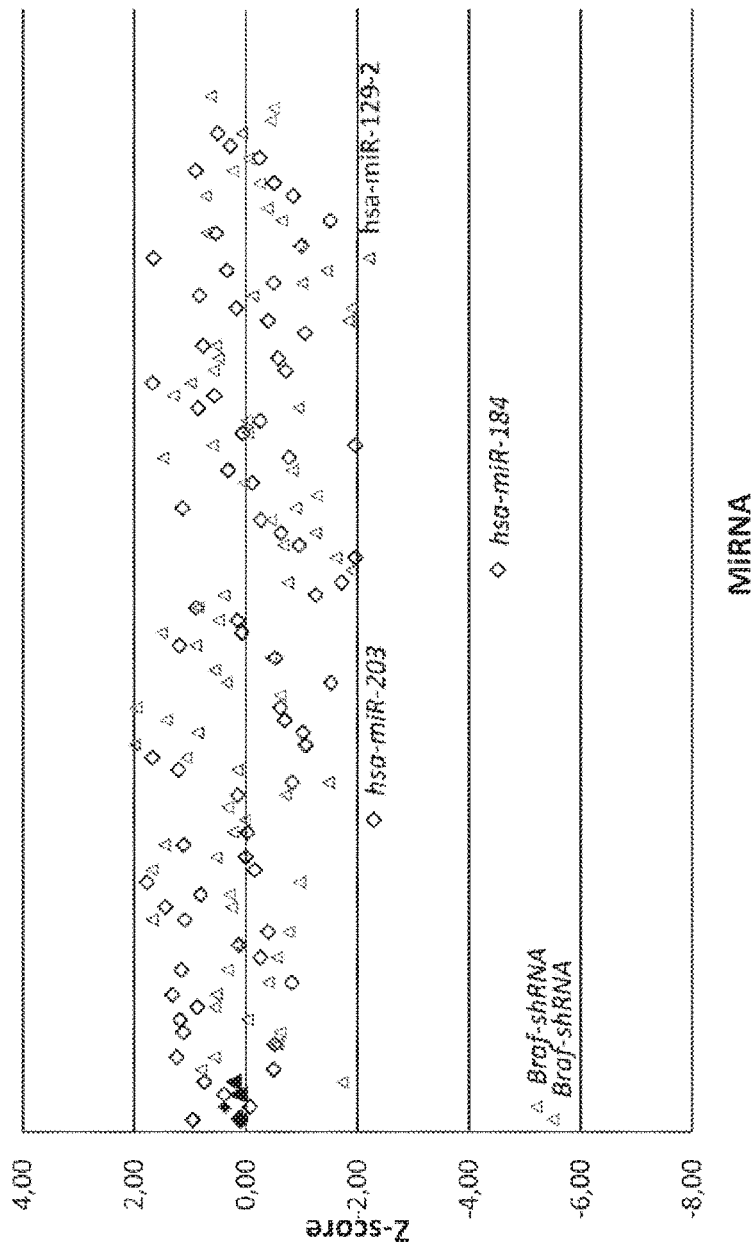
FIG. 1.

There has been evidence that miRNAs play a role in melanoma development. However, no systematic study has been performed to determine the role of all known miRNAs in melanoma cells. Therefore, we undertook the exercise of generating a library of in lentiviral constructs comprising in total 1120 miRNAs (14 plates, each containing 80 miR vectors), among which miRNAs as described in miRBase v12, supplemented by a selection of miRNAs that were previously discovered by our team (WO2007/081204, WO2007/081196). We examined the effect of the overexpression of these miRNAs on cell growth in a melanoma cell line containing a BRaf mutation, A375. A screen was performed where melanoma cells were infected with lentiviruses encoding a miRNA at varying MOI in a 96 well plate, where each well contained cells infected with an individual miRNA. As a negative control, cells infected with a lentivirus containing an empty vector were used. As a technical positive control, cells infected with a BRaf specific shRNA were used. 93 miRNAs had either a Z-score<−2 (for inhibitors of cell viability) or >2 (for stimulators of cell viability) and these were selected for confirmation in a second screen. An example of the distribution of the Z-score of miRNAs for on of the calculation methods in two of the 14 screened plates is shown in FIG. 1. This shows that the majority of the miRNAs do not have a significant affect cell growth. miRNAs 129-2, 203 and 184 were selected from these plates, since they showed a Z-score below the threshold of −2.

In this second screen, the first screen was repeated with the same viral titers as used previously, in addition to a screen with fixed MOI (100 and 200). miRNAs that showed the same effect in two of these confirmatory screens were further selected for additional confirmation experiments. This concerned 20 miRNAs.

To determine whether the observed effect on cell growth could indeed be attributed to the expression of the mature miRNA, a quantitative RT-PCR was performed for cells infected with each of these 20 miRNAs. This confirmed for the miRNAs as listed in Table 1 that the precursor sequence as introduced by the lentivirus was expressed and indeed resulted in processing into a mature miRNA.

Additionally, DNA sequencing on cells infected with miRNAs as listed in Table 1 confirmed the sequence of these miRNAs as introduced.

Figure 2:
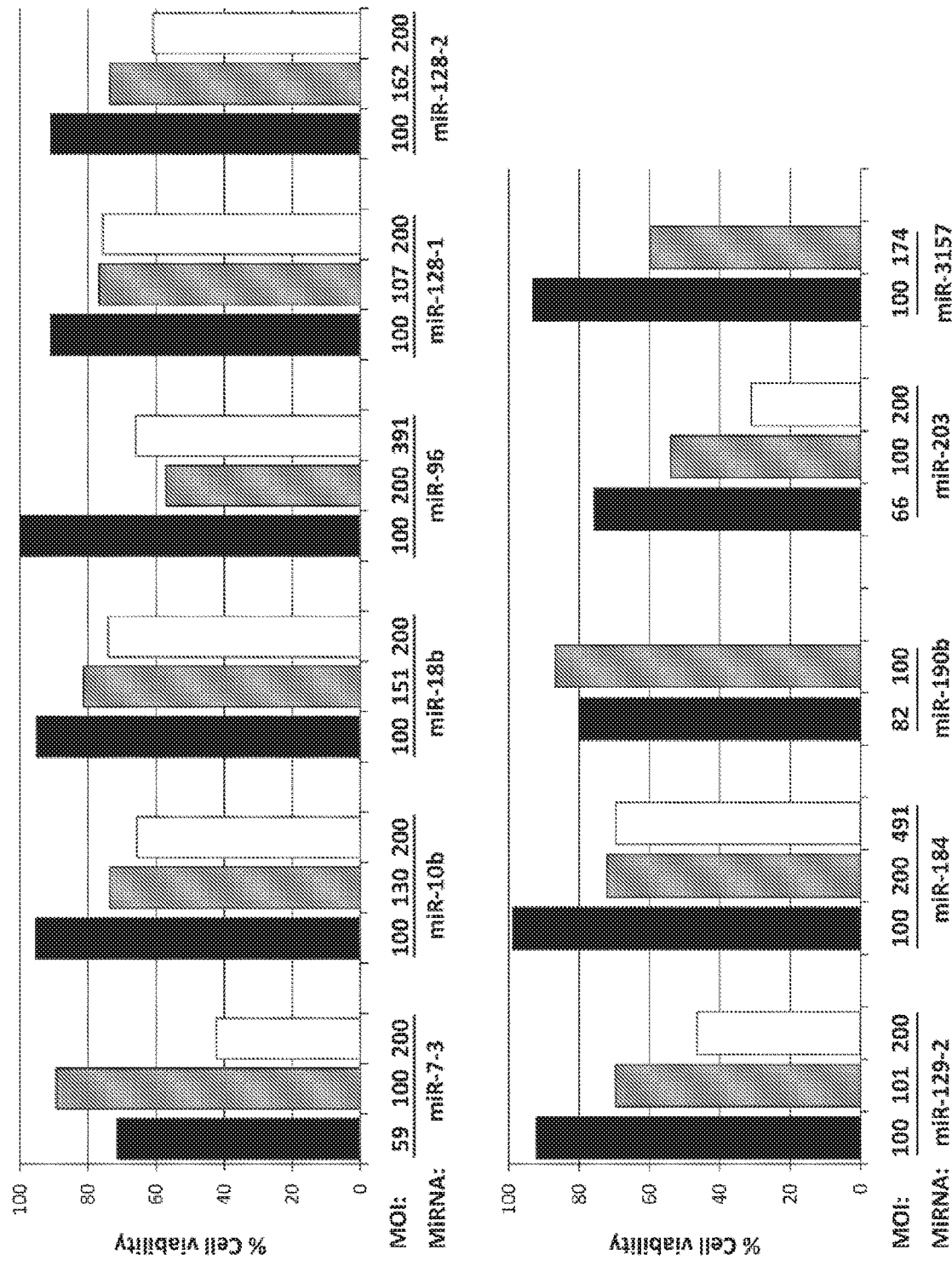

For the selected miRNAs as listed in Table 1, inhibition of cell growth was calculated as compared to growth in cells infected with empty vector. FIG. 2 shows a compilation of the 2 screens at the different MOIs used in those screens. For most of these miRNAs a significant inhibition was obtained with a range of 100-500. More importantly, when correlating the levels of inhibition with MOI, a trend towards dose dependency can be observed. In other words, when the expression of the miRNA is increased, the effect is also enhanced.

Figure 3:
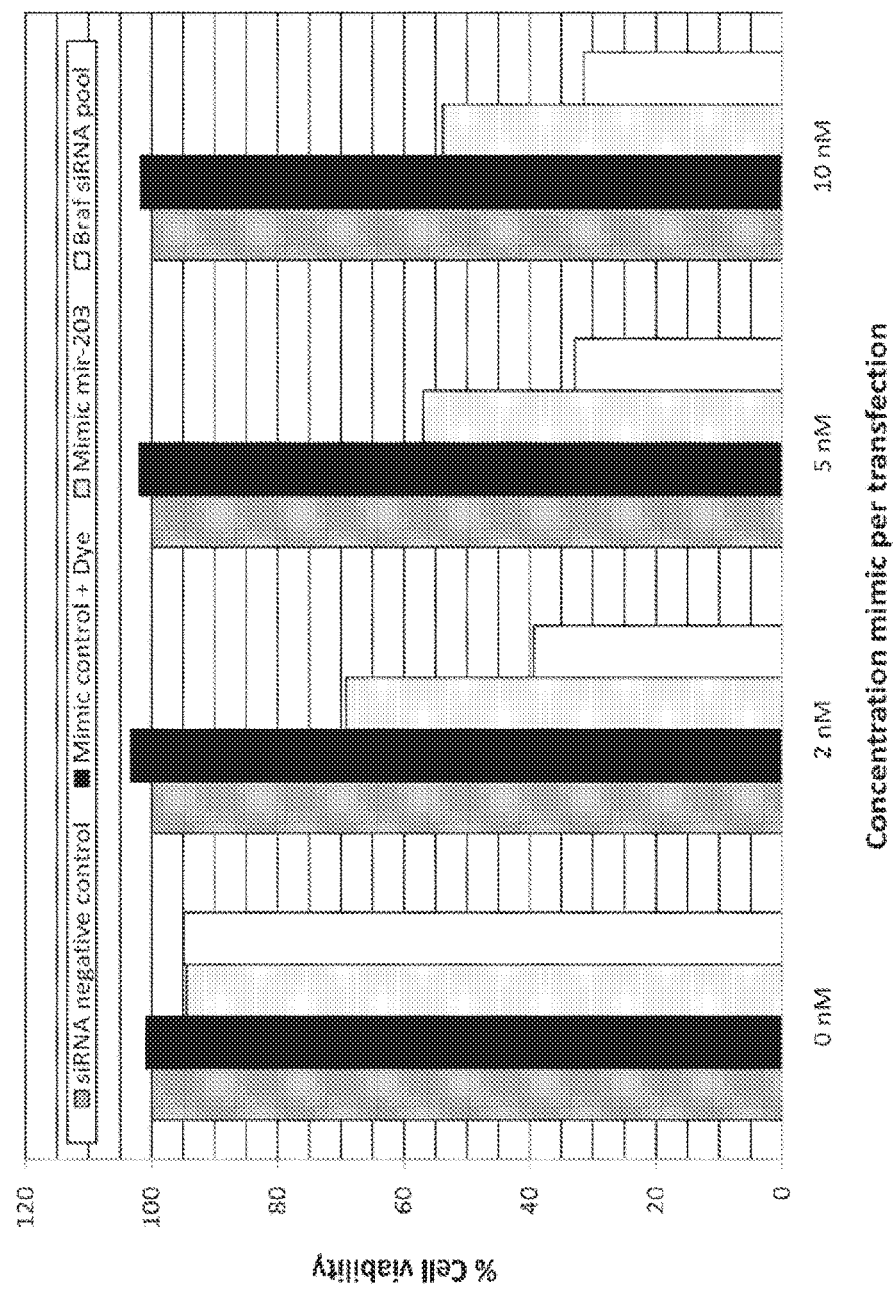

To further validate the function of the selected miRNAs, a synthetic mimic molecule for miR-203 was used. In the same cell growth assay, a synthetic mimic as well as a control miRNA and, as a positive control, a BRAF siRNA was added to melanoma cells in increasing concentrations (FIG. 3). Both the negative miRNA control as well as the siRNA negative control showed no effect on cell growth.

The siRNA for BRAF showed a significant inhibition of cell growth in a dose dependent manner (60-70%). Similarly, the mimic for miR-203 also showed a significant reduction of cell growth in a dose dependent manner (30-45%). This experiment will also be repeated for mimics derived from the other miRNAs as listed in Table 1.

EXAMPLE 2

Material and Methods

The same procedure as described in Example 1 was used to identify another set of miRNAs that inhibit cell growth. The primers used for the quantitative RT-PCR experiment were (Seq ID NOs: 36-57):

```
MiR-16
SL-primer:
5'-GTCGTATCCAGTGCAGGGTCCGAGGTATTCGCACTGGATACGACCG
CCAA-3'

Forward primer:
5'-GCCCGCCCAATATTACTGTGCTGC-3'

MiR-133a:
SL-primer:
5'-GTCGTATCCAGTGCAGGGTCCGAGGTATTCGCACTGGATACGACCA
GCTG-3'

Forward primer:
5'-GCCCGCTTTGGTCCCCTTCAACCA-3'

MiR-509-3p:
SL-primer:
5'-GTCGTATCCAGTGCAGGGTCCGAGGTATTCGCACTGGATACGACCT
ACCC-3'

Forward primer:
5'-TGCCAGTGATTGGTACGTCTGTGG-3'

MiR-509-5p:
SL-primer:
5'-GTCGTATCCAGTGCAGGGTCCGAGGTATTCGCACTGGATACGACTG
ATTG-3'

Forward primer:
5'-TGCCAGTACTGCAGACAGTGGCA-3'

MiR-497:
SL-primer:
5'-GTCGTATCCAGTGCAGGGTCCGAGGTATTCGCACTGGATACGACAC
AAAC-3'

Forward primer:
5'-TGCCAGCAGCAGCACACTGTGGT-3' miR-200c*:
SL-primer:
5'-GTCGTATCCAGTGCAGGGTCCGAGGTATTCGCACTGGATACGACCC
AAAC-3'

Forward primer:
5'-TGCCAGCGTCTTACCCAGCAGTGT-3' miR-95:
SL-primer:
5'-GTCGTATCCAGTGCAGGGTCCGAGGTATTCGCACTGGATACGACTG
CTCA-3'

Forward primer:
5'-TGCCAGTTCAACGGGTATTTATTG-3'
```

-continued

```
MiR-182
SL-primer:
5'-GTCGTATCCAGTGCAGGGTCCGAGGTATTCGCACTGGATACGACAG
TGTG-3'

Forward primer:
5'-GCCCGCTTTGGCAATGGTAGAACT-3'

MiR-193a-3p:
SL-primer:
5'-GTCGTATCCAGTGCAGGGTCCGAGGTATTCGCACTGGATACGACAC
TGGG-3'

Forward primer:
5'-TGCCAGAACTGGCCTACAAAGTCC-3'

MiR-610:
SL-primer:
5'-GTCGTATCCAGTGCAGGGTCCGAGGTATTCGCACTGGATACGACTC
CCAG-3'

Forward primer:
5'-TGCCAGTGAGCTAAATGTGTGCT-3' miR-10b*:
SL-primer:
5'-GTCGTATCCAGTGCAGGGTCCGAGGTATTCGCACTGGATACGAATT
CCC-3'

Forward primer:
5'-GCCCGCACAGATTCGATTCTAGGG-3'
```

Results

We undertook the exercise of generating a library of lentiviral constructs comprising in total 1120 miRNAs (14 plates, each containing 80 miR vectors), among which miRNAs as described in miRBase v12, supplemented by a selection of miRNAs that were previously discovered by our team (WO2007/081204, WO2007/081196). We examined the effect of the overexpression of these miRNAs on cell viability in a melanoma cell line containing a BRaf mutation, A375 (obtained from the Hubrecht Laboratory and originally described in Giard et al. J. Natl. Cancer Inst. 51, 1417, 1973A screen was performed where melanoma cells were infected with lentiviruses encoding a miRNA at varying MOI in a 96 well plate, where each well contained cells infected with an individual miRNA. As a negative control, cells were infected with a lentivirus containing an empty vector. As a technical positive control, cells infected with a BRaf specific shRNA were used. 93 miRNAs had either a Z-score<−2 (for inhibitors of cell viability) or >2 (for stimulators of cell viability) and these were selected for confirmation in a second screen. An example of the distribution of the Z-score of miRNAs for one of the calculation methods in two of the 14 screened plates is shown in FIG. 1. This shows that the majority of the miRNAs do not have a significant effect on cell growth. miRNAs 129-2, 203 and 184 were selected from these plates, since they showed a Z-score below the threshold of −2.

In the second screen, the first screen was repeated with the same viral titers as used previously, in addition to a screen with fixed MOI (100 and 200). miRNAs that showed the same effect in two of these confirmatory screens were further selected for additional confirmation experiments. In addition to the 20 miRNAs described in Example 1, this concerned 15 miRNAs.

To determine whether the observed effect on cell growth could indeed be attributed to the expression of the mature miRNA, a quantitative RT-PCR was performed for cells infected with each of these 15 miRNAs. This confirmed for the miRNAs as listed in Table 7 that the precursor sequence as introduced by the lentivirus was expressed and indeed resulted in processing into a mature miRNA.

Additionally, DNA sequencing on cells infected with miRNAs as listed in Table 7 confirmed the sequence of these miRNAs as introduced.

EXAMPLE 3

Inhibition of Cell Viability by microRNA Mimics in A375

To validate the miRNAs from the screen, miRNA mimics (mature sequence represented by 19-22 synthetic double stranded oligonucleotides) were selected for transfection. Mimics (Pre-miR™ miRNA Precursor Molecule, Ambion) and siRNA's (ON-TARGETplus SMARTpool, Dharmacon) with available controls were ordered and tested. As a positive control, a BRAF siRNA pool was used. Cell viability was determined with the MTS assay as described in Example 1.

Materials and Methods

Confirmation of miRNA hits using mature miRNA oligonucleotide mimics were performed in triplicate using 0.5 uL X-tremeGene (Roche) and 3000 cells per well at 10 nM mimic concentration. The viability is expressed as % viable cells compared to the siRNA control pool vector. Absorbance was measured 72 hours after transfection using the MTS assay as described above.

The sequence of the positive control BRAF siRNA pool from Dharmacon was (Seq ID NOs: 64-67):

```
5'-CAUGAAGACCUCACAGUAA-3'

5'-UCAGUAAGGUACGGAGUAA-3'

5'-AGACGGGACUCGAGUGAUG-3'

5'-UUACCUGGCUCACUAACUA-3'
```

Sequences of the scrambled siRNA pool (Dharmacon) are proprietary and have not been disclosed by the supplier.

The sequence of negative controls scrambled miRNA mimic from Ambion was (Seq ID NOs: 68):

```
5'-UGU ACU GCU UAC GAU UCG GTT-3'
```

The sequences of the miRNA mimics are listed in Table 3 (Seq ID NOs: 96-129

Results

The results for the miRNA mimics are listed in Table 8. MiRNAs that induced a decrease in cell viability by more than 22% (Average of controls (siRNA pool, Ambion mimic control #2)−2*average(SD) of all mimics) are listed in Table 8.

EXAMPLE 4

Inhibition of Cell Viability by Combination of miRNAs

To validate the concept that combination of miRNAs is beneficial for inhibition of cell viability compared to the inhibition by a single miRNA, the miRNA mimics were tested in combinations.

Material and Methods

A375 (Hubrecht) cells were seeded in 96-well plates (2000 and 3000 cells). All combinations for 15 miRNAs, siRNA control pool and water were made as stock solutions. 24 hours after plating, cells were transfected in triplicate with 10 nM miRNA mimic or 10 nM miRNA mimic combination (5 nM per miRNA) and 0.3 uL or 0.5 uL X-tremeGene (Roche) respectively according to manufacturer's instructions. Absorbance was measured 72 hours after transfection using the CellTiter AQueous One Solution Cell Proliferation Assay (MTS, Promega) according manufacturer's protocol. The same experiment was performed using a concentration of 3 nM miRNA mimic. To select combinations of miRNAs with a beneficial effect, the % inhibition of cell viability induced by the miRNA mimic combinations was compared to the % inhibition of the two individual mimics. Combinations that show more than 10% increase of % inhibition of viability compared to the individual mimics are considered beneficial (see Table 9).

Results

The % remaining cell viability for the individual miRNAs and the % remaining cell viability of the miRNA beneficial combinations are shown in Table 9. Of the miRNAs that were tested miR-96 has a high frequency for beneficial effects as compared to the other miRNA's. MiR-10b, miR-16 and miR-203 are also well represented. The miRNAs were tested in four different conditions by varying cell density (2000 and 3000 cells) and mimic concentration (3 and 10 nM). Four miRNA combinations inhibit cell proliferation significantly better than the individual miRNA in three out of the four conditions. The following combinations: (1) miR-16 plus miR-10b, (2) miR-96 plus miR-10b, (3) miR-96 plus miR-16 and (4) miR-96 with miR-203 give the best inhibition for most conditions.

EXAMPLE 5

Inhibition of Cell Viability in Other Melanoma Cell Lines with BRAF Mutation

The A375 melanoma cell line is a commonly used cell line to represent melanoma. To study whether the miRNAs that were identified by screening in A375 cells are also active in other melanoma cell lines, the miRNAs were tested in (1) A375 from the Hubrecht Laboratory, (2) A375 cells obtained from the ATCC (CRL-1619™), (3) SK-MEL28 (obtained from the ATCC (HTB72)) and (4) SK-MEL24 (obtained from the ATCC (HTB71). SK-MEL-28 and SK-MEL-24 are both V600E BRAF mutated melanoma cell lines derived from the skin.

Material and Methods

Mimics (Pre-miR™ miRNA Precursor Molecule, Ambion) and siRNA's (ON-TARGETplus SMARTpool, Dharmacon) with available controls were ordered and tested (see for sequence example 3). The miRNAs synthetic mimics were transfected in the three cell lines using X-TremeGene (Roche), according to an optimized protocol for each cell line. Cell viability was determined with the MTS assay as described above. Absorbance was measured 72 hours after transfection. Experiments were performed in triplicate using 0.5 uL X-tremeGene (Roche) and 3000 cells (A375 Hubrecht and A375 ATCC), 0.3 uL X-tremeGene and 2000 cells (SK-MEL-28), or 0.5 uL X-tremeGene and 5000 cells (SK-MEL-24). The decrease in viability is expressed as % remaining viable cells compared to the siRNA control pool vector at a dose of 10 nM for all cell lines.

The beneficial effect of combinations of miRNAs was also tested in SK-MEL28 cells using the stock solutions of miRNAs as described in Example 4. Cell viability was determined with the MTS assay as described above. Absorbance was measured 72 hours after transfection. Experiments were performed in triplicate using 0.5 uL X-tremeGene (Roche) and 3000 cells (SK-MEL28) and 0.3 uL X-tremeGene and 2000 cells (SK-MEL-28).

Results

The results are depicted in Table 10. Out of 14 miRNA mimics that were tested in the A375ATCC cell line, 13 showed a remaining cell viability of less than 80% in A375 cells from the ATCC. This indicates that >90% of the mimics that were significantly inhibiting cell viability of A375 cells from the Hubrecht laboratory are also active in the A375 cell line from ATCC 15 miRNA mimics that significantly inhibit cell viability of A375 cells were tested in SK-MEL28. Table 10 shows that 10 of these 15 miRNA mimics inhibit the cell viability of SK-MEL28 cells by more than 80%. This indicates that 67% of the miRNA mimics that inhibit the cell viability of A375 cells inhibit the cell viability of another melanoma cell line that contains the activating BRAF V600E mutation.

The cross-reactivity of 10 miRNAs that are significantly inhibiting the cell viability of A375 cells with miRNAs that inhibit cell viability in SK-MEL24 is 30% (3 out of 10 using a cut-off or less than 80% remaining cell viability). This relatively low cross reactivity is ascribed to a sub-optimal transfection protocol.

In summary, the data in Table 10 suggest that the majority of miRNAs mimics that were identified by screening the inhibition of cell viability of A375 melanoma cells also inhibit cell proliferation in other melanoma cell lines that contain the activated BRAF pathway.

The % remaining cell viability upon transfection of a combination of miRNA mimics in SK-MEL28 is depicted in Table 9. These data show that miR-203 has a high frequency for beneficial effects as compared to the other miRNA's. Surprisingly, miR-18b and miR-18b*, do not induce a large decrease in cell viability after transfection in SK-MEL28 with the individual miRNA. However, in combination with miR-203, there is a 10% beneficial effect on decrease of cell viability after transfection with miR-18b or miR-18b* (see Table 9).

EXAMPLE 6

Inhibition of Cell Viability in Other Cancers with an Activated BRAF Pathway

The miRNAs that were identified from the lentiviral screen in A375 cells are expected to inhibit cell proliferation pathways including the activated BRAF pathway in the A375 cells. Since the BRAF pathway is activated in many other tumor types, these miRNAs were tested in a non-melanoma cancer cell line that also contains the V600E BRAF mutation. One such cell line is the ES-2 ovarian cancer cell line that has originally been derived from a poorly differentiated ovarian clear cell carcinoma with fibroblast morphology.

Material and Methods

3000 ES-2 (obtained from ATCC (CRL-1978™)) cells per well were seeded in a 96-wells plate on day one, using McCoy's 5a medium supplemented with 10% Fetal Calf Serum (FCS) and 100 U penicillin and 100 µg/mL streptomycin. At day two the cells were treated with 10 nM of mimic in 0.5 ug/mL of X-treme Gene. After 24 h the medium was discarded and cells were grown in fresh medium. At day five 100 µL fresh medium was added and 30 µL of MTS (3-(4,5-dimethylthiazol-2-yl)-5-(3-carboxymethoxyphenyl)-2-(4-sulfophenyl)-2H-tetrazolium), in the presence of phenazine methosulfate (PMS). This produces a formazan product that has an absorbance maximum at 490-500 nm in PBS which was measured after 4 hours on incubation.

Results

Table 10 shows the inhibition of metabolic activity of the ES-2 ovarian cancer cell line by the miRNA mimics that were identified from the lentiviral screen. Several miRNA mimics that inhibit cell viability of the melanoma cell lines A375 and SK-MEL-28 also inhibit the cell viability in the ovarian ES-2 cell line (e.g. miR-509-3p, miR-497, miR-96, miR-200c*, miR-10b, miR-3157, and miR-182). In total 20 miRNA mimics that inhibit cell viability of A375 cells were tested in ES-2 ovarian cancer cell line. 12 out of these 20 miRNA mimics inhibit the cell viability of ES-2 cells (60% cross reactivity). This indicates that the majority of the miRNAs that are listed in Table 1 and 7 are of interest for the treatment of cancers with an activated BRAF pathway.

EXAMPLE 7

Inhibition of Cell Viability in Endothelial Cells (BRAF WT).

To investigate whether the inhibitory miRNAs that have been identified by screening in A375 cells are indeed selectively inhibiting the BRAF pathway, the miRNAs were tested in normal endothelials cells (HUVEC) that lack the V600E BRAF mutation.

Material and Methods

MiRNAs were introduced into the A375 cells (Hubrecht) by using the lentiviral transduction procedure as described in Example 1 using 0.5 µl lentivirus from the library.

For culture and lentiviral transduction of HUVEC cells with the same set of miRNAs the following protocol was used:

Day −8: Start Cell Growth of HUVECs in a T25 Culture Flask

Coat a T25 culture flask per cell type with 2 ml 1% gelatin for an hour at 37° C. Thaw cells (these cells were frozen in 95% corresponding medium and 5% DMSO) obtained from the −80° C. deep freezer at 37° C. in a water bath. Clean the vial with 70% ethanol and transfer the cells in the culture flasks with 5 ml of the appropriate growth medium and place at 37° C., 95% humidity and 5% $CO_2$ 4 hours after seeding, the DMSO containing medium must be replaced by fresh warm culture medium. The cells are subsequently incubated for three days at 37° C., 95% humidity and 5% $CO_2$.

Day −5: Transfer of HUVECs to a T75 Culture Flask

Coat a T75 culture flask per cell line with 6 ml 1% gelatin for an hour at 37° C.

Remove gelatin.

Wash the T25 culture flask with cells once with 1×PBS.

Spread 0.5 ml TrypLE Express evenly over the cell surface and remove the excess.

Incubate at room temperature until all cells have detached.

Resuspend the cells in 15 ml cell specific growth medium (as done before) and incubate the cells in a T75 culture flask at 37° C., 95% humidity and 5% $CO_2$.

Day −1: Seeding of HUVECs in 96 Well Plates

Coat the 96 well plates with 30 µl/well 1% gelatin for an hour at 37° C.

Wash the T75 culture flask with cells once with 1×PBS.

Spread 1.0 ml TrypLE Express evenly over the cell surface and remove the excess.

Incubate at room temperature until all cells have detached.

Inactivate the trypsin process through addition of 5 ml/T75 fresh specific growth medium.

Add 20 µl 0.4% trypan blue solution to the same volume of cell suspension and count the cells using the Fuchs-Rosenthal chamber. This is done by counting 3 of the 16 squares consisting of 16 squares each. To calculate the amount of cells (n) per ml the average cell number is corrected for dilution and multiplied by 5000 (c/ml=n×2× 5000).

To seed one 96 well plate with HUVECs at a concentration of 2000 cells/well, 2.4E+5 cells need to be suspended in an end volume of 18 ml. 150 µl suspension is to be added to each well.

The plated cells will be incubated at 37° C., 95% humidity and 5% $CO_2$ overnight.

Day 0: Transduction of HUVECs in the Morning

HUVECs were exposed to 6 µg/ml polybrene.

For every lentiviral transduction, depending on the titer, a specific volume was added to the cells to obtain a final concentration of lentivirus corresponding to MOI of 200.

After addition of the virus to the cells cells were incubated at 37° C., 95% humidity and 5% $CO_2$ for 24 hours. Experiments were performed in duplicate and empty vector lentivirus was used as negative control.

Day 1: Medium Refreshment of HUVECs 24 Hours after Transduction

Remove all virus containing medium using a multichannel and dispose of it according to the MLII procedure.

Add 150 µl fresh and warm (37° C.) medium to the cells and incubate at 37° C., 95% humidity and 5% $CO_2$. Also refresh medium untransduced plate(s).

Day 4: Medium Refreshment of HUVECs 96 Hours after Transduction

Remove 100 µl virus containing medium using a multichannel and dispose of it according to the MLII protocols.

Add 100 µl fresh and warm (37° C.) medium to the cells and incubate at 37° C., 95% humidity and 5% $CO_2$.

Day 7: Medium Refreshment of HUVECs 168 Hours after Transduction

Remove all virus containing medium using a multichannel and dispose of it according to the MLII protocols.

Add 150 µl fresh and warm (37° C.) medium to the cells and incubate at 37° C., 95% humidity and 5% $CO_2$.

Day 8: Cell Viability Assay, 8 Days after Transduction Using MTS

Add 20 µl/well MTS solution to 150 µl medium.

Incubate at 37° C., 95% humidity and 5% $CO_2$ for 4 hours. Shake the plates so that all non dissolved crystals dissolve and measure the absorbance at 492 nm using the Multiskan FC.

Results

The results are summarized in Table 11 and shows that the majority of the A375 hits do not inhibit the cell viability of normal cell types such as endothelial cells. In addition, the data indicate that the majority of the miRNAs do not affect the cell viability of a cell line that contains wild type BRAF. This suggests that the miRNAs that were identified by screening cell viability in A375 cells may be selective for cell lines bearing the V600E BRAF mutation. In addition, these data show that the miRNAs selectively inhibit proliferating tumor cells and do not inhibit proliferation of normal cells.

EXAMPLE 8

Involvement of the microRNA's in the Activated BRAF Pathway (pERK)

Activation of the BRAF pathway results in increased phosphorylation of ERK1 and ERK2 ('pERK'). Using a cell-based ELISA, we determined the effects of overexpression of the miRNAs on the levels of pERK in the melanoma cell line A375 (Hubrecht) after transfection with miRNA mimics.

Material and Methods

Melanoma cell line A375 (from Hubrecht) was transfected with different concentrations of siRNA (control pool or BRAF-specific) or miRNA mimics (mimic control or miRNA-specific) in a 96-well format (see Example 5 for sequence details). The effect on the levels of pERK was determined using a cell-based ELISA. Tubulin was used to normalize the pERK levels obtained with the ELISA. The normalized pERK levels for the untreated A375 cells ('0' concentration) were used as reference to calculate the change in pERK levels. The BRAF-specific siRNA was included as positive control. For Western blotting, cells were transfected with 100 nM miRNA/siRNA in a 6-well format, and harvested three days after transfection. Proteins were isolated and transferred onto PVDF membranes. BRAF, pERK and tubulin were detected using appropriate antibodies.

Results

The results are depicted in FIG. 4 and show that silencing BRAF with siRNA greatly reduces pERK levels, up to almost 80% at the highest concentration. In addition, we identified a number of miRNAs that also negatively affect the pERK levels, up to 40% (e.g. miR-96 and miR-129). This strongly suggests that these miRNAs modulate the BRAF pathway.

Figure 5:
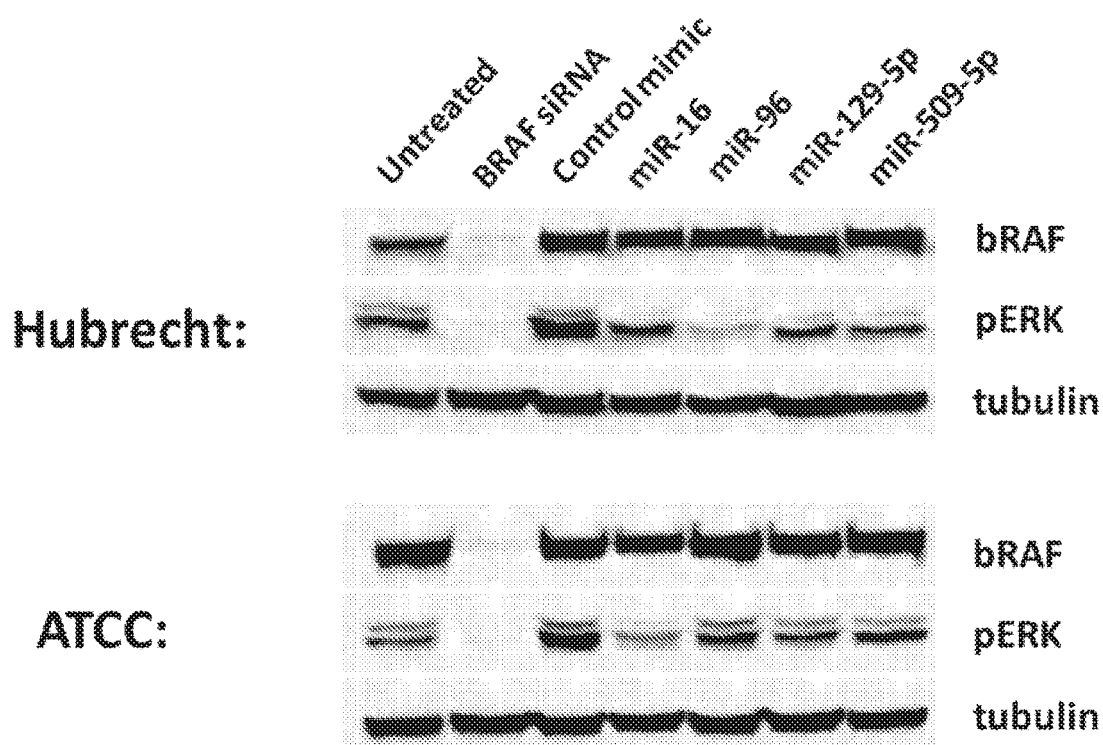
Figure 6:
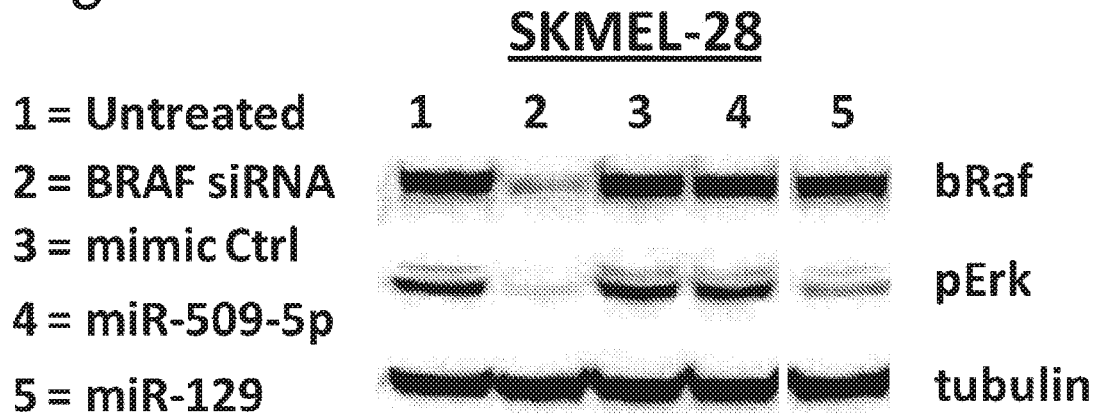

We selected the top five candidates (miR-96, -129, -509-5p, -128 and -16) to further examine their effect on pERK levels in A375 (Hubrecht) and A375 (ATCC) by Western blot analysis (FIG. 5). These microRNAs show, up to a certain extent, a reduction in the levels of pERK compared to scramled miRNA mimic. This nicely correlates with the ELISA, and further demonstrates that these miRNAs modulate the BRAF pathway. Compared to control scrambled mimic, the Western Blot data show that miR-16, miR-96 and miR-129 decrease pERK levels in the A375 cell line. FIG. 6 shows that that miR-129 also decreased pERK levels in the SK-MEL28 cell line.

TABLE 1 qRT-PCR results of selected miRNAs that affect cell growth in melanoma cells.
Quantitative RT-PCR is performed on melanoma cells infected with the listed miRNAs. Expression of the mature miRNA is detected and compared with the expression of the endogenous mature miRNA as detected in empty vector transfected melanoma cells. The measure of overexpression is determined by the difference in the number of PCR cycles necessary to generate detectable miRNA product as measured in empty vector vs miRNA infected cells (ΔΔCT). Additionally, this difference in necessary PCR cycles is translated to the fold increase in expression in miRNA vs empty vector infected cells.

| Mature miRNA | Overexpression (ΔΔCT) | Overexpression (fold increase) |
|---|---|---|
| miR-7 | | 34 |
| miR-10b | | 10 |
| miR-18b | | 42 |
| miR-18b* | | 13 |
| miR-96 | | 5 |
| miR-128 | | 67 |
| miR-129-5p | | 256 |
| miR-184 | | >1024 |
| miR-190b | | >1024 |
| miR-203 | | >1024 |
| miR-3157 | | 171 |

TABLE 2

Precursor sequences of miRNAs identified in screening
(see Table 1 and 7) List of miRNA precursor sequences
(5' to 3' direction). All sequences were obtained
from miRBase (release 15: April 2010; www.mirbase.org).

| SEQ ID NO | miRNA | Precursor sequence |
|---|---|---|
| 69 | Hsa-miR-7-1 | UUGGAUGUUGGCCUAGUUCUGUGUGGAAGACUAGUGAUUUUGUUGUU UUUAGAUAACUAAAUCGACAACAAAUCACAGUCUGCCAUAUGGCACA GGCCAUGCCUCUACAG |
| 70 | Hsa-miR-7-2 | CUGGAUACAGAGUGGACCGGCUGGCCCCAUCUGGAAGACUAGUGAUU UUGUUGUUGUCUUACUGCGCUCAACAACAAAUCCCAGUCUACCUAAU GGUGCCAGCCAUCGCA |
| 71 | Hsa-miR-7-3 | AGAUUAGAGUGGCUGUGGUCUAGUGCUGUGUGGAAGACUAGUGAUUU UGUUGUUCUGAUGUACUACGACAACAAGUCACAGCCGGCCUCAUAGC GCAGACUCCCUUCGAC |
| 72 | Hsa-miR-10b | CCAGAGGUUGUAACGUUGUCUAUAUAUACCCUGUAGAACCGAAUUUG UGUGGUAUCCGUAUAGUCACAGAUUCGAUUCUAGGGGAAUAUAUGGU CGAUGCAAAAACUUCA |
| 73 | Hsa-miR-18b | UGUGUUAAGGUGCAUCUAGUGCAGUUAGUGAAGCAGCUUAGAAUCUA CUGCCCUAAAUGCCCCUUCUGGCA |
| 74 | Hsa-miR-96 | UGGCCGAUUUUGGCACUAGCACAUUUUUGCUUGUGUCUCUCCGCUCU GAGCAAUCAUGUGCAGUGCCAAUAUGGGAAA |
| 75 | Hsa-miR-128-1 | UGAGCUGUUGGAUUCGGGGCCGUAGCACUGUCUGAGAGGUUUACAUU UCUCACAGUGAACCGUCUCUUUUUCAGCUGCUUC |
| 76 | Hsa-iR-128-2 | UGUGCAGUGGGAAGGGGGGCCGAUACACUGUACGAGAGUGAGUAGCA GGUCUCACAGUGAACCGGUCUCUUUCCCUACUGUGUC |
| 77 | Hsa-miR-129-1 | GGAUCUUUUUGCGGUCUGGGCUUGCUGUUCCUCUCAACAGUAGUCAG GAAGCCCUUACCCCAAAAAGUAUCU |
| 78 | Hsa-miR-129-2 | UGCCCUUCGCGAAUCUUUUUGCGGUCUGGGCUUGCUGUACAUAACUC AAUAGCCGGAAGCCCUUACCCCAAAAAGCAUUUGCGGAGGGCG |
| 79 | Hsa-miR-184 | CCAGUCACGUCCCCUUAUCACUUUUCCAGCCCAGCUUUUGUGACUGUA AGUGUUGGACGGAGAACUGAUAAGGGUAGGUGAUUGA |
| 80 | Hsa-miR-190b | UGCUUCUGUGUGAUAUGUUUGAUAUUGGGUUGUUUAAUUAGGAACCA ACUAAAUGUCAAACAUAUUCUUACAGCAGCAG |
| 81 | Hsa-miR-203 | GUGUUGGGGACUCGCGCGCUGGGUCCAGUGGUUCUUAACAGUUCAAC AGUUCUGUAGCGCAAUUGUGAAAUGUUUAGGACCACUAGACCCGGCG GGCGCGGCGACAGCGA |
| 82 | Hsa-miR-3157 | GGGAAGGGCUUCAGCCAGGCUAGUGCAGUCUGCUUUGUGCCAACACU GGGGUGAUGACUGCCCUAGUCUAGCUGAAGCUUUUCCC |
| 83 | Hsa-miR-16-1 | GUCAGCAGUGCCUUAGCAGCACGUAAAUAUUGGCGUUAAGAUUCUAA AAUUAUCUCCAGUAUUAACUGUGCUGCUGAAGUAAGGUUGAC |
| 84 | Hsa-miR-16-2 | GUUCCACUCUAGCAGCACGUAAAUAUUGGCGUAGUGAAAUAUAUAUU AAACACCAAUAUUACUGUGCUGCUUUAGUGUGAC |
| 85 | Hsa-miR-133a-1 | ACAAUGCUUUGCUAGAGCUGGUAAAAUGGAACCAAAUCGCCUCUUCA AUGGAUUUGGUCCCCUUCAACCAGCUGUAGCUAUGCAUUGA |
| 86 | Hsa-miR-133a-2 | GGGAGCCAAAUGCUUUGCUAGAGCUGGUAAAAUGGAACCAAAUCGAC UGUCCAAUGGAUUUGGUCCCCUUCAACCAGCUGUAGCUGUGCAUUGA UGGCGCCG |
| 87 | Hsa-miR-509-1 | CAUGCUGUGUGUGGUACCCUACUGCAGACAGUGGCAAUCAUGUAUAA UUAAAAAUGAUUGGUACGUCUGUGGGUAGAGUACUGCAUGACACAUG |
| 88 | Hsa-miR-509-2 | CAUGCUGUGUGUGGUACCCUACUGCAGACAGUGGCAAUCAUGUAUAA UUAAAAAUGAUUGGUACGUCUGUGGGUAGAGUACUGCAUGACAC |
| 89 | Hsa-miR-509-3 | GUGGUACCCUACUGCAGACAGUGGCAAUCAUGUAUAAUUAAAAAUGAU UGGUACGUCUGUGGGUAGAGUACUGCAU |
| 90 | Hsa-miR-497 | CCACCCCGGUCCUGCUCCCGCCCCAGCAGCACACUGUGGUUUGUACG GCACUGUGGCCACGUCCAAACCACACUGUGGUGUUAGAGCGAGGGUG GGGGAGGCACCGCCGAGG |

TABLE 2-continued

Precursor sequences of miRNAs identified in screening
(see Table 1 and 7) List of miRNA precursor sequences
(5' to 3' direction). All sequences were obtained
from miRBase (release 15: April 2010; www.mirbase.org).

| SEQ ID NO | miRNA | Precursor sequence |
|---|---|---|
| 91 | Hsa-miR-200c | CCCUCGUCUUACCCAGCAGUGUUUGGGUGCGGUUGGGAGUCUCUAAU ACUGCCGGGUAAUGAUGGAGG |
| 92 | Hsa-miR-95 | AACACAGUGGGCACUCAAUAAAUGUCUGUUGAAUUGAAAUGCGUUAC AUUCAACGGGUAUUUAUUGAGCACCCACUCUGUG |
| 93 | Hsa-miR-182 | GAGCUGCUUGCCUCCCCCCGUUUUUGGCAAUGGUAGAACUCACACUG GUGAGGUAACAGGAUCCGGUGGUUCUAGACUUGCCAACUAUGGGGCG AGGACUCAGCCGGCAC |
| 94 | Hsa-miR-193a | CGAGGAUGGGAGCUGAGGGCUGGGUCUUUGCGGGCGAGAUGAGGGUG UCGGAUCAACUGGCCUACAAAGUCCCAGUUCUCGGCCCCCG |
| 95 | Hsa-miR-610 | UCUAUUUGUCUUAGGUGAGCUAAAUGUGUGCUGGGACACAUUUGAGC CAAAUGUCCCAGCACACAUUUAGCUCACAUAAGAAAAAUGGACUCUA GU |

TABLE 3

Mature sequences of miRNAs precursor (hairpin) identified
in screening. List of mature miRNA sequences
(5' to 3' direction) processed from miRNA precursor hairpins.
All sequences were obtained from miRBase (release 15: April
2010; www.mirbase.org). The sequences of the mature
miRNAs listed in Table 1 and 7 are enclosed in this Table.

| miRNA | Mature miRNA | Seq ID | Sequence mature miRNA |
|---|---|---|---|
| Hsa-mir-7-1 | miR-7 | 96 | UGGAAGACUAGUGAUUUUGUUGU |
| | miR-7-1* | 97 | CAACAAAUCACAGUCUGCCAUA |
| Hsa-miR-7-2 | miR-7 | 96 | UGGAAGACUAGUGAUUUUGUUGU |
| | miR-7-2* | 98 | CAACAAAUCCCAGUCUACCUAA |
| Hsa-miR-7-3 | miR-7 | 96 | UGGAAGACUAGUGAUUUUGUUGU |
| Hsa-miR-10b | miR-10b | 99 | UACCCUGUAGAACCGAAUUUGUG |
| | miR-10b* | 100 | ACAGAUUCGAUUCUAGGGGAAU |
| Hsa-miR-18b | miR-18b | 101 | UAAGGUGCAUCUAGUGCAGUUAG |
| | miR-18b* | 102 | UGCCCUAAAUGCCCCUUCUGGC |
| Hsa-miR-96 | miR-96 | 103 | UUUGGCACUAGCACAUUUUUGCU |
| | miR-96* | 104 | AAUCAUGUGCAGUGCCAAUAUG |
| Hsa-miR-128-1 Hsa-miR-128-2 | miR-128 | 105 | UCACAGUGAACCGGUCUCUUU |
| Hsa-miR-129-1 | miR-129-5p | 106 | CUUUUUGCGGUCUGGGCUUGC |
| | miR-129* | 107 | AAGCCCUUACCCCAAAAAGUAU |
| Hsa-miR-129-2 | miR-129-5p | 106 | CUUUUUGCGGUCUGGGCUUGC |
| | miR-129-3p | 108 | AAGCCCUUACCCCAAAAAGCAU |
| Hsa-miR-184 | miR-184 | 109 | UGGACGGAGAACUGAUAAGGGU |
| Hsa-miR-190b | miR-190b | 110 | UGAUAUGUUUGAUAUUGGGUU |
| Hsa-miR-203 | miR-203 | 111 | GUGAAAUGUUUAGGACCACUAG |
| Hsa-miR-3157 | miR-3157 | 112 | UUCAGCCAGGCUAGUGCAGUCU |
| Hsa-miR-16-1 | miR-16 | 113 | UAGCAGCACGUAAAUAUUGGCG |
| | miR-16-1* | 114 | CCAGUAUUAACUGUGCUGCUGA |
| Hsa-miR-16-2 | miR-16 | 113 | UAGCAGCACGUAAAUAUUGGCG |
| | miR-16-2* | 115 | CCAAUAUUACUGUGCUGCUUUA |
| Hsa-miR-133a-1 Hsa-miR-133a-2 | miR-133a | 116 | UUUGGUCCCCUUCAACCAGCUG |

TABLE 3-continued

Mature sequences of miRNAs precursor (hairpin) identified in screening. List of mature miRNA sequences (5' to 3' direction) processed from miRNA precursor hairpins. All sequences were obtained from miRBase (release 15: April 2010; www.mirbase.org). The sequences of the mature miRNAs listed in Table 1 and 7 are enclosed in this Table.

| miRNA | Mature miRNA | Seq ID | Sequence mature miRNA |
|---|---|---|---|
| Hsa-miR-509-1 | miR-509-3p | 117 | UGAUUGGUACGUCUGUGGGUAG |
| Hsa-miR-509-2 | miR-509-5p | 118 | UACUGCAGACAGUGGCAAUCA |
| Hsa-miR-509-3 | miR-509-3p | 117 | UGAUUGGUACGUCUGUGGGUAG |
|  | miR-509-3-5p | 119 | UACUGCAGACGUGGGCAAUCAUG |
| Hsa-miR-497 | miR-497 | 120 | CAGCAGCACACUGUGGUUUGU |
|  | miR-497* | 121 | CAAACCACACUGUGGUGUUAGA |
| Hsa-miR-200c | miR-200c | 122 | UAAUACUGCCGGGUAAUGAUGGA |
|  | miR-200c* | 123 | CGUCUUACCCAGCAGUGUUUGG |
| Hsa-miR-95 | miR-95 | 124 | UUCAACGGGUAUUUAUUGAGCA |
| Hsa-miR-182 | miR-182 | 125 | UUUGGCAAUGGUAGAACUCACACU |
|  | miR-182* | 126 | UGGUUCUAGACUUGCCAACUA |
| Hsa-miR-193a | miR-193a-3p | 127 | AACUGGCCUACAAAGUCCCAGU |
|  | miR-193a-5p | 128 | UGGGUCUUUGCGGGCGAGAUGA |
| Hsa-miR-610 | miR-610 | 129 | UGAGCUAAAUGUGUGCUGGGA |

TABLE 4

Sequences of miRNAs identified in screening as cloned in lentiviral vectors

| SEQ ID NO | miRNA | Cloned sequence in lentiviral vector |
|---|---|---|
| 130 | Hsa-miR-7-1 | GCCTTAACCAAGCAAACTTCTCATTTCTCTGGTGAAAACTGCTGCCAAAACCACTTGTTAAAAATTGTACAGAGCCTGTAGAAAATATAGAAGATTCATTGGATGTTGGCCTAGTTCTGTGTGGAAGACTAGTGATTTTGTTGTTTTTAGATAACTAAATCGACAACAAATCACAGTCTGCCATATGGCACAGGCCATGCCTCTACAGGACAAATGATTGGTGCTGTAAAATGCAGCATTTCACACCTTACTAGC |
| 131 | Hsa-miR-7-2 | TGAAGGAGCATCCAGACCGCTGACCTGGTGGCGAGGGGAGGGGGTGGTCCTCGAACGCCTTGCAGAACTGGCCTGGATACAGAGTGGACCGGCTGGCCCCATCTGGAAGACTAGTGATTTTGTTGTTGTCTTACTGCGCTCAACAACAAATCCCAGTCTACCTAATGGTGCCAGCCATCGCAGCGGGGTGCAGGAAATGGGGGCAGCCCCCCTTTTTGGCTATCCTTCCACGTGTTCT |
| 132 | Hsa-miR-7-3 | TCATAGCTTGGCTCAGGTGAGAAGGAGGAGCTGGGCAGGGGTCTCAGACATGGGGCAGAGGGTGGTGAAGAAGATTAGAGTGGCTGTGGTCTAGTGCTGTGTGGAAGACTAGTGATTTTGTTGTTCTGATGTACTACGACAACAAGTCACAGCCGGCCTCATAGCGCAGACTCCCTTCGACCTTCGCCTTCAATGGGCTGGCCAGTGGGGAGAACCGGGGAGGTCGGGGAAGAATCGCTTCCACTCGGAGTGGGGGGCTGGCTCACTCCAGGCGATACAG |
| 133 | Hsa-miR-10b | TGGCTCAGAGGAAGAGATTGGGGCCGGCAGCGACCTAGGTACCTCACTCTGGGTGGGACCCAGAGGTTGTAACGTTGTCTATATATACCCTGTAGAACCGAATTTGTGTGGTATCCGTATAGTCACAGATTCGATTCTAGGGGAATATATGGTCGATGCAAAAACTTCACGTTTCTTCGGAATAGCCAGAGACCAAAGTGCGACATGGAGACTAGAAGCA |
| 134 | Hsa-miR-18b | CCATGGTGATTTAGTCAATGGCTACTGAGAACTGTAGTTTGTGCATAATTAAGTAGTTGATGCTTTTGAGCTGCTTCTTATAATGTGTCTCTTGTGTTAAGGTGCATCTAGTGCAGTTAGTGAAGCAGCTTAGAATCTACTGCCCTAAATGCCCCTTCTGGCACAGGCTGCCTAATATACAGCATTTTAAAAGTATGCCTTGAGTAGTAATTTGAATAGGACACATTTCAGTGGTTTG |
| 135 | Hsa-miR-96 | CTCCTAGACGTCGGAAACAGGCTGCTTCCAAGGGTGCAGGGATGCAAGGCCCCTCGTCCAGTGTGTCCCCAGAGAGCCCGCACCAGTGCCATCTGCTTGGCCGATTTTGGCACTAGCACATTTTTGCTTGTGTCTCTCCGCTCTGAGCAATCATGTGCAGTGCCAATATGGGAAAAGCAGGACCCCGCAGCTGCGTCCGCCTCCCCTGCATCCTTGTGTCAGG |
| 136 | Hsa-miR-128-1 | TTGACAAGTTTGTAGCTTCACCATATACATTTAATATTTTGCAATAATTGGCCTTGTTCCTGAGCTGTTGGATTCGGGGCCGTAGCACTGTCTGAGAGGTTTACATTT |

TABLE 4-continued

Sequences of miRNAs identified in screening as cloned in lentiviral vectors

| SEQ ID NO | miRNA | Cloned sequence in lentiviral vector |
|---|---|---|
| | | CTCACAGTGAACCGGTCTCTTTTTCAGCTGCTTCCTGGCTTCTTTTTACTCAGG
TTTCCACTGCTTTTTTGCTTTTTTTAATGCTGTATGAAGGTGTTAACATTTGTT
TATATTTTTCATTAATTGTAATACCTTTAAATCATGCATCATACTCAGAAATAG
GGA |
| 137 | Hsa-miR-128-2 | TGACTCCATGGTTCACTTTCATGATGGCCACATGCCTCCTGCCCAGAGCCCGGC
AGCCACTGTGCAGTGGGAAGGGGGCCGATACACTGTACGAGAGTGAGTAGCAG
GTCTCACAGTGAACCGGTCTCTTTCCCTACTGTGTCACACTCCTAATGGAATGC
CGTTATCCAAAGAGCAGCAC |
| 138 | Hsa-miR-129-1 | GTACCAGCTAAGCCCTGGAGGGGCCACAGCCTCCCCTCCAGCCCCCCTGCCATG
GGATGGCTGCTGTCTCCTTTGGATCTTTTTGCGGTCTGGGCTTGCTGTTCCTCT
CAACAGTAGTCAGGAAGCCCTTACCCCAAAAAGTATCTGCGGGAGGCCTTGTCC
ACAGGGGAGGCTGCCCCAAGGGCTCCAGGTGAGTCACAGCAAACCCAAG |
| 139 | Hsa-miR-129-2 | GAGACATCCTGGGCTGAAGGCGGCGGCGAACCGAAGAAGCCGGCATATTCTGCC
CTTCGCGAATCTTTTTGCGGTCTGGGCTTGCTGTACATAACTCAATAGCCGGAA
GCCCTTACCCCAAAAAGCATTTGCGGAGGGCGCACTCGTCGAGAAGACGGCAGC
CATCCAGCGATCGCCGAAGCCCGCACCTTCCCGAAGCTGCTCCATCCGAGCCTT
ACC |
| 140 | Hsa-miR-184 | TACATCTTGTCCTGCAAAGCTTCATCAAAACTTCTTTGCCGGCCAGTCACGTCC
CCTTATCACTTTTCCAGCCCAGCTTTGTGACTGTAAGTGTTGGACGGAGAACTG
ATAAGGGTAGGTGATTGACACTCACAGCCTCCGGAACCCCCGCGCCGCCTGCAC
TTGCGTGATGG |
| 141 | Hsa-miR-190b | TCTTTGCAACTGGAAGGAAGGCAGATGACCCCCAAAGCTCTCCTGCCTGCTTCT
GTGTGATATGTTTGATATTGGGTTGTTTAATTAGGAACCAACTAAATGTCAAAC
ATATTCTTACAGCAGCAGGTGATTCAGCACCACCCTCTTTCATACTTCAATCTC
TGGGGCTCCTGTCTCTTTTACTGAACCTCTTCTCTCCAGG |
| 142 | Hsa-miR-203 | GACCAGCGGGGATCTGGGCGCAGGGGCCGGTCCCCGGGATCCGCAGGCGACGCG
GGCGGTCCCAAGGGCGTCGGGGGCTCCTCTCTCCGCAGCTCGGCGAACCGACGG
TGTTGGGGACTCGCGCGCTGGGTCCAGTGGTTCTTAACAGTTCAACAGTTCTGT
AGCGCAATTGTGAAATGTTTAGGACCACTAGACCCGGCGGGCGCGGCGACAGCG
ACGGAGCGTCCCACGCGCGGCCTGGAGTCAGAGTCACAGTCAGGGG |
| 143 | Hsa-miR-3157 | ACAACTTCTCAATGAGTCTGCCCTCACTGTCCAACAATTGAGCTGAGAATATAA
GAAGGGAAGGGCTTCAGCCAGGCTAGTGCAGTCTGCTTTGTGCCAACACTGGGG
TGATGACTGCCCTAGTCTAGCTGAAGCTTTTCCCTTCTTTCTACACCCAGCTCA
AGTCCCAGGTCCATAAAACCTTTAGAAACTCTTCAGAAACTCTTTAGAGCTTCA
GAAGCTCTTGAGAATTGGAAGATG |
| 144 | Hsa-miR-16-1 | TTGTGGATTTTGAAAAGGTGCAGGCCATATTGTGCTGCCTCAAAAATACAAGGA
TCTGATCTTCTGAAGAAAATATATTTCTTTTATTCATAGCTCTTATGATAGCA
ATGTCAGCAGTGCCTTAGCAGCACGTAAATATTGGCGTTAAGATTCTAAAATTA
TCTCCAGTATTAACTGTGCTGCTGAAGTAAGGTTGACCATACTCTACAGTTGTG
TTTTAATGTATATTAATGTTACTAATGTGTTTTCAGTTTTATTGA |
| 145 | Hsa-miR-16-2 | TTTCATCATCAGATGTTCGTTTTATGTTTGGATGAACTGACATACTTGTTCCAC
TCTAGCAGCACGTAAATATTGGCGTAGTGAAATATATATTAAACACCAATATTA
CTGTGCTGCTTTAGTGTGACAGGGATACAGCAACTATTTTATCAATTGTTTGTA
TTTCCCTTTAAGG |
| 146 | Hsa-miR-133a-1 | CTTGTAGAAGGTCCATGACTGTAATTTTACCAATGAAAAGCATTTAACTGTTTT
GGATTCCAAACTAGCAGCACTACAATGCTTTGCTAGAGCTGGTAAAATGGAACC
AAATCGCCTCTTCAATGGATTTGGTCCCCTTCAACCAGCTGTAGCTATGCATTG
ATTACTACGGGACAACCAACGTTTTCATTTGTGAATATCAATTACTTGCCAACT
AATTTCAACTT |
| 147 | Hsa-miR-133a-2 | GGGACTGCTTGGTGGAGCCGCCTTCTTCACCGACGTCGCTGTTCCTCGGATCTG
GGAGCCAAATGCTTTGCTAGAGCTGGTAAAATGGAACCAAATCGACTGTCCAAT
GGATTTGGTCCCCTTCAACCAGCTGTAGCTGTGCATTGATGGCGCCGTGCGGCC
CGGCCGCAGGTCCCGCAGCCGTGGAGAGGACCCAGCAGGTGGCGCGGGGAGAGC
CCGGCTCGGCACGTGGTCAGCTCCAAGTAAGTGAA |
| 148 | Hsa-miR-509-1 | TGAATGGGTGGGTATTAAGGCAAGGCTGCCATCCTCAGACATGCTGTGTGTGGT
ACCCTACTGCAGACAGTGGCAATCATGTATAATTAAAAATGATTGGTACGTCTG
TGGGTAGAGTACTGCATGACACATGCAACATACATGATGACACTGTGTGTGT
TGGAGGCATTTAGTTGCATGCAGAGG |
| 149 | Hsa-miR-509-2 | TGAATGGGTGGGTATTAAGGCAAGGCTGCCATCCTCAGACATGCTGTGTGTGGT
ACCCTACTGCAGACAGTGGCAATCATGTATAATTAAAAATGATTGGTACGTCTG
TGGGTAGAGTACTGCATGACACGTGCAACATACATGATGACACTGTGTGTGTGT
TGGAGGCATTTAGTTGCATGCAGAGG |

TABLE 4-continued

Sequences of miRNAs identified in screening as cloned in lentiviral vectors

| SEQ ID NO | miRNA | Cloned sequence in lentiviral vector |
|---|---|---|
| 150 | Hsa-miR-509-3 | TGAATGGGTGGGTATTAAGGCAAGGCTGCCATCCTCAGACATGCTGTGTGTGGT ACCCTACTGCAGACGTGGCAATCATGTATAATTAAAAATGATTGGTACGTCTGT GGGTAGAGTACTGCATGACACGTGCAACATACATGATGACACTGTGTGTGTT GGAGGCATTTAGTTGCATGCAGAGG |
| 151 | Hsa-miR-497 | TCCCAGCACTGCTATGTGCTCTCTTCCTTTCAACCCACCCCGGTCCTGCTCCCG CCCCAGCAGCACACTGTGGTTTGTACGGCACTGTGGCCACGTCCAAACCACACT GTGGTGTTAGAGCGAGGGTGGGGGAGGCACCGCCGAGGCTTGGCCCTGGGAGGC CATCCTGGAGAAGTGACACA |
| 152 | Hsa-miR-200c | AAGCTGCCTGACCCAAGGTGGGCGGGCTGGGCGGGGGCCCTCGTCTTACCCAGC AGTGTTTGGGTGCGGTTGGGAGTCTCTAATACTGCCGGGTAATGATGGAGGCCC CTGTCCCTGTGTCAGCAACATCCATCGCCTCA |
| 153 | Hsa-miR-95 | AACAAAGCATTTGCACACAGCAAGGCACGCCACCTGCACCCCGGGACGTCCATC TGTAGCGCGCCCAAGGAAGGTAGGATTGTGACACCCAACACAGTGGGCACTCAA TAAATGTCTGTTGAATTGAAATGCGTTACATTCAACGGGTATTTATTGAGCACC CACTCTGTGCCAGACGCTGAGCGGGGCGCCGAGGGGGACAGAGAAGACAAGAGC AGCC |
| 154 | Hsa-miR-182 | CTGTCTCTTCCTCAGCACAGACCGAGGCCTCCCCAGCTCCTGGGGGGAGCTGCT TGCCTCCCCCCGTTTTTGGCAATGGTAGAACTCACACTGGTGAGGTAACAGGAT CCGGTGGTTCTAGACTTGCCAACTATGGGGCGAGGACTCAGCCGGCACCCTGTG CACAGCCAGCGAGGGAAGGGCCGGCCATGCTGGACCTGCTGTTCTCC |
| 155 | Hsa-miR-193a | AGGGACACCCAGAGCTTCGGCGGAGCGGAGCGCGGTGCACAGAGCCGGCGACCG GACCCAGCCCCGGGAAGCCCGTCGGGGACGCACCCCGAACTCCGAGGATGGGAG CTGAGGGCTGGGTCTTTGCGGGCGAGATGAGGGTGTCGGATCAACTGGCCTACA AAGTCCCAGTTCTCGGCCCCCGGGACCAGCGTCTTCTCCCCGGTCCTCGCCCCA GGCCGGCTTCCTCCCGGGCTGGCGTGCGCTCCGGCCAGGCTGCCTCTCAGGTCC ACGCTGGAGAAGGAGTGGTGAGGT |
| 156 | Hsa-miR-610 | ATTGTATTCAGAGGGGCAACACTTAACATAAAATCTGACTTCAACAGACTATTA TTCTCTGTGAATAAGGTCTTACATATTAGCCCTTCACTCCCAACTATTTGTCTA TTTGTCTTAGGTGAGCTAAATGTGTGCTGGGACACATTTGAGCCAAATGTCCCA GCACACATTTAGCTCACATAAGAAAAATGGACTCTAGTTGGGAGTGAGGGGCTA ATAAACACCAGATCCCAAGAAAATT |

TABLE 5

Seed sequences of miRNAs identified in screening
List of miRNA seed sequences (5' to 3' direction). Seed sequence is defined as nucleotide 2-8 (5' to 3' direction) of the mature miRNA sequence processed from miRNA precursor hairpins. All sequences were obtained from miRBase (release 15: April 2010; www.mirbase.org). The seed sequences of the mature miRNAs listed in Table 1 and 7 are enclosed in this Table.

| miRNA | Mature miRNA | Seq ID | Sequence mature miRNA |
|---|---|---|---|
| Hsa-miR-7-1 | miR-7 | 157 | GGAAGAC |
|  | miR-7-1* | 158 | AACAAAU |
| Hsa-miR-7-2 | miR-7 | 157 | GGAAGAC |
|  | miR-7-2* | 159 | AACAAAU |
| Hsa-miR-7-3 | miR-7 | 157 | GGAAGAC |
| Hsa-miR-10b | miR-10b | 160 | ACCCUGU |
|  | miR-10b* | 161 | CAGAUUC |
| Hsa-miR-18b | miR-18b | 162 | AAGGUGC |
|  | miR-18b* | 163 | GCCCUAA |
| Hsa-miR-96 | miR-96 | 164 | UUGGCAC |
|  | miR-96* | 165 | AUCAUGU |
| Hsa-miR-128-1 Hsa-miR-128-2 | miR-128 | 166 | CACAGUG |
| Hsa-miR-129-1 | miR-129-5p |  | UUUUUGC |
|  | miR-129* | 168 | AGCCCUU |

TABLE 5-continued

Seed sequences of miRNAs identified in screening
List of miRNA seed sequences (5' to 3' direction). Seed sequence is defined as nucleotide 2-8 (5' to 3' direction) of the mature miRNA sequence processed from miRNA precursor hairpins. All sequences were obtained from miRBase (release 15: April 2010; www.mirbase.org). The seed sequences of the mature miRNAs listed in Table 1 and 7 are enclosed in this Table.

| miRNA | Mature miRNA | Seq ID | Sequence mature miRNA |
|---|---|---|---|
| Hsa-miR-129-2 | miR-129-5p | 167 | UUUUUGC |
|  | miR-129-3p | 169 | AGCCCUU |
| Hsa-miR-184 | miR-184 | 170 | GGACGGA |
| Hsa-miR-190b | miR-190b | 171 | GAUAUGU |
| Hsa-miR-203 | miR-203 | 172 | UGAAAUG |
| Hsa-miR-3157 | miR-3157 | 173 | UCAGCCA |
| Hsa-miR-16-1 | miR-16 | 174 | AGCAGCA |
|  | miR-16-1* | 175 | CAGUAUU |
| Hsa-miR-16-2 | miR-16 | 174 | AGCAGCA |
|  | miR-16-2* | 176 | CAAUAUU |
| Hsa-miR-133a-1 | miR-133a | 177 | UUGGUCC |
| Hsa-miR-133a-2 |  |  |  |
| Hsa-miR-509-1 | miR-509-3p | 178 | GAUUGGU |
| Hsa-miR-509-2 | miR-509-5p | 179 | ACUGCAG |
| Hsa-miR-509-3 | miR-509-3p | 178 | GAUUGGU |
|  | miR-509-3-5p | 180 | ACUGCAG |
| Hsa-miR-497 | miR-497 | 181 | AGCAGCA |
|  | miR-497* | 182 | AAACCAC |
| Hsa-miR-200c | miR-200c | 183 | AAUACUG |
|  | miR-200c* | 184 | GUCUUAC |
| Hsa-miR-95 | miR-95 | 185 | UCAACGG |
| Hsa-miR-182 | miR-182 | 186 | UUGGCAA |
|  | miR-182* | 187 | GGUUCUA |
| Hsa-miR-193a | miR-193a-3p | 188 | ACUGGCC |
|  | miR-193a-5p | 189 | GGGUCUU |
| Hsa-miR-610 | miR-610 | 190 | GAGCUAA |

TABLE 6

IsomiR sequences of miRNAs identified in screening (see Table 3) These isomiRs have been detected after the analysis of 100 human tissue an cell line libraries using high-throughput deep sequencing and only isomiRs that represent >2.5% of the total number of cloned sequences are listed here.

| miRNA | Mature miRNA | Seq ID | IsomiR sequence |
|---|---|---|---|
| Hsa-miR-7-1 | miR-7 | 191 | UGGAAGACUAGUGAUUUUGUUGUU |
| Hsa-mir-7-2 |  | 192 | UGGAAGACUAGUGAUUUUGUUG |
| Hsa-miR-7-3 | miR-7 | 191 | UGGAAGACUAGUGAUUUUGUUGUU |
|  |  | 193 | UGGAAGACUAGUGAUUUUGUUGUUC |
|  |  | 192 | UGGAAGACUAGUGAUUUUGUUG |
| Hsa-miR-10b | miR-10b | 194 | UACCCUGUAGAACCGAAUUUGU |
|  |  | 195 | ACCCUGUAGAACCGAAUUUGUG |
|  |  | 196 | UACCCUGUAGAACCGAAUUUG |
|  |  | 197 | ACCCUGUAGAACCGAAUUUGU |
|  |  | 198 | ACCCUGUAGAACCGAAUUUGUGU |
|  | miR-10b* | 199 | AGAUUCGAUUCUAGGGGAAUA |
|  |  | 200 | ACAGAUUCGAUUCUAGGGGAA |
|  |  | 201 | CAGAUUCGAUUCUAGGGGAAU |

TABLE 6-continued

IsomiR sequences of miRNAs identified in screening (see Table 3) These isomiRs have been detected after the analysis of 100 human tissue an cell line libraries using high-throughput deep sequencing and only isomiRs that represent >2.5% of the total number of cloned sequences are listed here.

| miRNA | Mature miRNA | Seq ID | IsomiR sequence |
|---|---|---|---|
| | | 202 | CAGAUUCGAUUCUAGGGGAAUA |
| | | 203 | AGAUUCGAUUCUAGGGGAA |
| | | 204 | CAGAUUCGAUUCUAGGGGAA |
| | | 205 | AGAUUCGAUUCUAGGGGAAU |
| | | 206 | AGAUUCGAUUCUAGGGGAAUAU |
| Hsa-miR-18b | miR-18b | 207 | UAAGGUGCAUCUAGUGCAGUU |
| | | 208 | UAAGGUGCAUCUAGUGCAGUUA |
| | | 209 | UAAGGUGCAUCUAGUGCAG |
| | | 210 | UAAGGUGCAUCUAGUGCAGU |
| | | 211 | AAGGUGCAUCUAGUGCAGU |
| | miR-18b* | 212 | UACUGCCCUAAAUGCCCCUUCU |
| | | 213 | UACUGCCCUAAAUGCCCCUUCUG |
| | | 214 | UACUGCCCUAAAUGCCCCUU |
| | | 215 | ACUGCCCUAAAUGCCCCUUCU |
| | | 216 | ACUGCCCUAAAUGCCCCUUCUG |
| | | 217 | UACUGCCCUAAAUGCCCCUUC |
| | | 218 | UACUGCCCUAAAUGCCCCUUCUGGC |
| | | 219 | UACUGCCCUAAAUGCCCCU |
| | | 220 | ACUGCCCUAAAUGCCCCUUCGGC |
| | | 221 | ACUGCCCUAAAUGCCCCUUCUGG |
| Hsa-miR-96 | miR-96 | 222 | UUUGGCACUAGCACUUUUG |
| | | 223 | UUUGGCACUAGCACAUUUUUGC |
| | | 224 | UUUGGCACUAGCACAUUUUU |
| Hsa-miR-128-1 | miR-128 | 225 | UCACAGUGAACCGGUCUCUUUU |
| | | 226 | UCACAGUGAACCGGUCUCUU |
| | | 227 | UCACAGUGAACCGGUCUCU |
| Hsa-miR-128-2 | miR-128 | 228 | UCACAGUGAACCGGUCUCUUUC |
| | | 226 | UCACAGUGAACCGGUCUCUU |
| | | 227 | UCACAGUGAACCGGUCUCU |
| | | 229 | UCACAGUGAACCGGUCUCUUUCC |
| Hsa-miR-129-1 | miR-129-5p | 230 | CUUUUUGCGGUCUGGGCUUG |
| | | 231 | CUUUUUGCGGUCUGGGCUU |
| | | 232 | CUUUUUGCGGUCUGGGCU |
| | | 233 | CUUUUUGCGGUCUGGGCUUGCU |
| Hsa-miR-129-2 | miR-129-5p | 230 | CUUUUUGCGGUCUGGGCUUG |
| | | 231 | CUUUUUGCGGUCUGGGCUU |
| | | 233 | CUUUUUGCGGUCUGGGCUUGCU |
| | | 232 | CUUUUUGCGGUCUGGGCU |
| Hsa-miR-184 | miR-184 | 234 | UGGACGGAGAACUGAUAAGGGUA |
| | | 235 | UGGACGGAGAACUGAUAAGGG |
| | | 236 | UGGACGGAGAACUGAUAAGG |
| Hsa-miR-190b | miR-190b | 237 | UGAUAUGUUUGAUAUUGGGUUG |
| | | 238 | UGAUAUGUUUGAUAUUGGGUUGU |
| Hsa-miR-203 | miR-203 | 239 | UGAAAUGUUUAGGACCACUAG |
| | | 240 | GUGAAAUGUUUAGGACCACUA |
| | | 241 | GUGAAAUGUUUAGGACCACU |
| | | 242 | GUGAAAUGUUUAGGACCACUAGA |
| Hsa-miR-3157 | miR-3157 | 243 | UUCAGCCAGGCUAGUGCAGUC |
| | | 244 | CUUCAGCCAGGCUAGUGCAGUC |
| | | 245 | UCAGCCAGGCUAGUGCAGUCU |
| | | 246 | UUCAGCCAGGCUAGUGCAGU |
| | | 247 | CUUCAGCCAGGCUAGUGCAGUCUG |

TABLE 6-continued

IsomiR sequences of miRNAs identified in screening (see Table 3) These isomiRs have been detected after the analysis of 100 human tissue an cell line libraries using high-throughput deep sequencing and only isomiRs that represent >2.5% of the total number of cloned sequences are listed here.

| miRNA | Mature miRNA | Seq ID | IsomiR sequence |
|---|---|---|---|
| Hsa-miR-16-1 | miR-16 | 248 | UAGCAGCACGUAAAUAUUGGC |
| Hsa-miR-16-2 | | 249 | UAGCAGCACGUAAAUAUUG |
| | | 250 | UAGCAGCACGUAAAUAUUGGCGU |
| | | 251 | UAGCAGCACGUAAAUAUUGG |
| Hsa-miR-133a-1 | miR-133a | 252 | UUGGUCCCCUUCAACCAGCUGU |
| Hsa-miR-133a-2 | | 253 | UUUGGUCCCCUUCAACCAGCU |
| | | 254 | UUUGGUCCCCUUCAACCAGCUGU |
| | | 255 | UUGGUCCCCUUCAACCAGCUG |
| | | 256 | UUGGUCCCCUUCAACCAGCU |
| Hsa-miR-509-1 | miR-509-3p | 257 | UGAUUGGUACGUCUGUGGGUAGA |
| Hsa-miR-509-2 | | 258 | UGAUUGGUACGUCUGUGGGUA |
| | | 259 | AUUGGUACGUCUGUGGGUAGA |
| | miR-509-5p | 260 | UACUGCAGACAGUGGCAAUCAUG |
| | | 261 | UACUGCAGACAGUGGCAAUCAU |
| | | 262 | UACGCAGACAGUGGCAAUC |
| | | 263 | UACUGCAGACAGUGGCAAUCAUGU |
| Hsa-miR-509-3 | miR-509-3-3p | 257 | UGAUUGGUACGUCUGUGGGUAGA |
| | | 258 | UGAUUGGUACGUCUGUGGGUA |
| | | 259 | AUUGGUACGUCUGUGGGUAGA |
| | miR-509-3-5p | 264 | UACUGCAGACGUGGCAAUCAU |
| | | 265 | UACUGCAGACGUGGCAAUCA |
| Hsa-miR-497 | miR-497 | 266 | CAGCAGCACACUGUGGUUUGUA |
| | | 267 | AGCAGCACACUGUGGUUUGU |
| | | 268 | AGCAGCACACUGUGGUUUGUA |
| | | 269 | AGCAGCACACUGUGGUUUGUAC |
| | | 270 | CAGCAGCACACUGUGGUUUG |
| Hsa-miR-200c | miR-200c* | 271 | CGUCUUACCCAGCAGUGUUUG |
| | | 272 | CGUCUUACCCAGCAGUGUUU |
| | | 273 | GUCUUACCCAGCAGUGUUUGG |
| Hsa-miR-95 | miR-95 | 274 | UUCAACGGGUAUUUAUUGAGC |
| | | 275 | UUCAACGGGUAUUUAUUGAG |
| Hsa-miR-182 | miR-182 | 276 | UUUGGCAAUGGUAGAACUCACACUG |
| | | 277 | UUUGGCAAUGGUAGAACUCACAC |
| | | 278 | UUUGGCAAUGGUAGAACUCACACUGG |
| | | 279 | UUUGGCAAUGGUAGAACUCACA |
| | | 280 | UUUGGCAAUGGUAGAACUC |
| | | 281 | UUUGGCAAUGGUAGAACUCA |
| | | 282 | UUUGGCAAUGGUAGAACUCAC |

TABLE 6-continued

IsomiR sequences of miRNAs identified in screening (see Table 3) These isomiRs have been detected after the analysis of 100 human tissue an cell line libraries using high-throughput deep sequencing and only isomiRs that represent >2.5% of the total number of cloned sequences are listed here.

| miRNA | Mature miRNA | Seq ID | IsomiR sequence |
|---|---|---|---|
| Hsa-miR-193a | miR-193a-3p | 283 | AACUGGCCUACAAAGUCCCA |
|  |  | 284 | AACUGGCCUACAAAGUCCCAG |
| Hsa-miR-610 | miR-610 | 285 | UGAGCUAAAUGUGUGCUGGGAC |
|  |  | 286 | UGAGCUAAAUGUGUGCUGGGACAC |
|  |  | 287 | AGCUAAAUGUGUGCUGGGACAC |
|  |  | 288 | GAGCUAAAUGUGUGCUGGGAC |
|  |  | 289 | AGGUGAGCUAAAUGUGUGCUG |
|  |  | 290 | AGCUAAAUGUGUGCUGGGACA |
|  |  | 291 | UGAGCUAAAUGUGUGCUGGGACACAU |
|  |  | 292 | GAGCUAAAUGUGUGCUGGG |
|  |  | 293 | UGAGCUAAAUGUGUGCUGGGACA |
|  |  | 294 | UGAGCUAAAUGUGUGCUGGGACACA |

TABLE 7 qRT-PCR results of selected additional miRNAs that affect cell growth in melanoma cells.

Quantitative RT-PCR is performed on melanoma cells infected with the listed miRNAs. Expression of the mature miRNA is detected and compared with the expression of the endogenous mature miRNA as detected in empty vector transfected melanoma cells. The measure of overexpression is determined by the difference in the number of PCR cycles necessary to generate detectable miRNA product as measured in empty vector vs miRNA infected cells ($\Delta\Delta CT$). Additionally, this difference in necessary PCR cycles is translated to the fold increase in expression in miRNA vs empty vector infected cells.

| Mature miRNA | Overexpression ($\Delta\Delta CT$) | Overexpression (fold increase) |
|---|---|---|
| miR-16 | — 0* | — 0* |
| miR-133a | 6.92 | 121 |
| miR-509-3p | 7.84 | 230 |
| miR-509-5p | 7.38 | 167 |
| miR-497 | 5.57 | 48 |
| miR-200c* | 6.96 | 125 |
| miR-95 | 9.23 | 599 |
| miR-182 | 6.29 | 78 |
| miR-193a-3p | 0.73 | 2 |
| miR-610 | 8.28 | 310 |
| miR-10b* | 5.90 | 60 |

*The fold increase for miR-16 is low, while there is a functional response after transduction with Hsa-miR-16-2 and after transfection with miRNA-16 mimic. Most likely, processing of Has-miR-16-2 results in an isomiR that is not picked up by the 5'primer in the RT-qPCR. The isomiR and the miR-16 mimic have the same seed sequence, resulting in a functional response with both procedures.

TABLE 8

List of miRNAs mimics that significantly inhibit cell viability compared to scrambled siRNA pool. The % remaining cell viability after transfection with 10 nM small RNA in A375 cells mimic is depicted. siRNA against BRAF is used as positive control. Scrambled miRNA mimic (Ambion) and scrambled siRNA pool (Dharmacon) are used as negative control . . .

| MiR Hairpin | MiR expressed and active as mimic miRNA | % viable cells compared to siRNA control pool | Standard Deviation | Number of experiments |
|---|---|---|---|---|
| hsa-mir-203 | miR-203 | 68 | 7.2 | 5 |
| hsa-mir-16-2 | miR-16 | 62 | 7.6 | 5 |
| hsa-mir-184 | miR-184 | 62 | 10.1 | 3 |
| hsa-mir-133a-1 | miR-133a | 60 | 17.6 | 2 |
| hsa-mir-509-1 | miR-509-3p | 66 |  | 1 |
|  | miR-509-5p | 56 |  | 1 |
| hsa-mir-497 | miR-497 | 61 | 8.2 | 2 |
| hsa-mir-96 | miR-96 | 53 | 2.1 | 2 |
| hsa-mir-200c | miR-200c* | 76 | 13.0 | 2 |
| hsa-mir-95 | miR-95 | 74 |  | 1 |
| hsa-mir-7 | miR-7 | 51 | 1.5 | 2 |
| hsa-mir-10b | miR-10b | 67 | 20.3 | 2 |
| hsa-mir-129-2 | miR-129-5p | 63 | 14.3 | 4 |
| hsa-mir-190b | miR-190b | 63 | 17.1 | 2 |
| hsa-mir-3157 | miR-3157 | 51 | 9.2 | 3 |
| hsa-mir-182 | miR-182 | 69 | 11.1 | 7 |
| hsa-mir-193a | miR-193a-3P | 54 | 19.4 | 2 |
| hsa-mir-610 | miR-610 | 78 |  | 1 |
| Negative control scr miRNA Ambion #2 |  | 93 | 7.7 | 6 |
| Negative control siRNA pool |  | 100 | 0.0 | 8 |
| Positive control siBRAF |  | 36 | 10.9 | 5 |

TABLE 9

List of miRNAs mimic combinations that significantly inhibit cell viability compared to negative control scrambled siRNA pool. The % remaining cell viability after transfection with 10 nM and 3 nM miRNA mimic in A375 cells or SK-MEL28 cells (2000 or 3000 cells) is depicted.

| miRNA 1 | miRNA 2 | A375 % viable cells 3 nM (2000) | A375 % viable cells 10 nM (2000) | A375 % viable cells 3 nM (3000) | A375 % viable cells 10 nM (3000) | SK-MEL28 % viable cells 3 nM (2000) | SK-MEL28 % viable cells 10 nM (2000) | SK-MEL28 % viable cells 3 nM (3000) | SK-MEL28 % viable cells 10 nM (3000) |
|---|---|---|---|---|---|---|---|---|---|
| miR-128 | miR-10b* | 59 | | 81 | | | | | |
| miR-129-5p | miR-203 | | 36 | | | | | | |
| miR-16 | miR-203 | | 42 | | 43 | | | | |
| miR-16 | miR-10b | | 49 | 62 | 41 | | | | |
| miR-203 | miR-10b | 52 | | | | | | | |
| miR-7 | miR-3157 | | | | 57 | | | | |
| miR-96 | miR-10b* | | 45 | | | | | | |
| miR-96 | miR-129-5p | | | | 40 | | | | |
| miR-96 | miR-182 | 46 | | | | | | | |
| miR-96 | miR-184 | | | | 46 | | | | |
| miR-96 | miR-190b | | | 55 | | | | | |
| miR-96 | miR-10b | | 44 | 57 | 40 | | | | |
| miR-96 | miR-16 | 47 | | 56 | 37 | | 37 | | |
| miR-96 | miR-203 | 43 | 37 | | 38 | | | | |
| miR-18b | miR-203 | | | | | | 69 | | 82 |
| miR-18b* | miR-203 | | | | | | 64 | | |
| miR-190b | miR-203 | | | | | 75 | 69 | | 81 |
| miR-7 | miR-203 | | | | | 72 | | | 78 |
| miR-16 | | | | | | 63 | 49 | 80 | 65 |
| miR-18b | | | | | | 99 | 96 | 101 | 99 |
| miR-18b* | | | | | | 95 | 81 | 99 | 94 |
| miR-7 | | 54 | 50 | 70 | 52 | 95 | 58 | 97 | 99 |
| miR-10b | | 65 | 54 | 76 | 53 | | | | |
| miR-10b* | | 79 | 72 | 96 | 79 | | | | |
| miR-96 | | 58 | 59 | 69 | 55 | | | | |
| miR-128 | | 72 | 69 | 92 | 72 | | | | |
| miR-129-5p | | 55 | 46 | 64 | 53 | | | | |
| miR-182 | | 56 | 51 | 78 | 52 | | | | |
| miR-184 | | 56 | 53 | 70 | 54 | | | | |
| miR-190b | | 50 | 42 | 68 | 51 | 96 | 83 | 99 | 94 |
| miR-203 | | 66 | 58 | 81 | 62 | 86 | 83 | 96 | 82 |
| miR-3157 | | 45 | 40 | 60 | 42 | | | | |

TABLE 10

Percentage remaining cell viability compared to the scrambled siRNA pool after transfection of miRNA mimics in various cell lines with the activated BRAF pathway (V600E mutation). The % remaining cell viability after transfection with 10 nM miRNA mimic is depicted for A375 cells from the Hubrecht laboratory (A375Hu), A375 cells from the ATCC, SKMEL28, SKMEL24 and ES-2.

| MiRNA hit expressed | A375Hu % viable cells | A375ATCC % viable cells | SKMEL28 % viable cells | SKMEL24 % viable cells | ES-2 % viable cells |
|---|---|---|---|---|---|
| miR-203 | 68 | 48 | 87 | 93 | 105 |
| miR-16 | 62 | 64 | 51 | 64 | 92 |
| miR-184 | 62 | 83 | | 99 | 84 |
| miR-133a | 60 | | 94 | | 95 |
| miR-509-3p | 66 | 62 | 66 | | 49 |
| miR-509-5p | 56 | 78 | 91 | | 78 |
| miR-497 | 61 | | 64 | | 63 |
| miR-96 | 53 | 70 | 47 | | 75 |
| miR-200c* | 76 | | 67 | | 76 |
| miR-95 | 74 | | 86 | | 72 |
| miR-7 | 51 | 59 | | | 67 |
| miR-10b | 67 | 66 | 56 | 95 | 49 |
| miR-10b* | 84 | 57 | | 56 | 69 |
| miR-128 | 81 | 72 | | 97 | 93 |
| miR-129-5p | 63 | 59 | 56 | 88 | 105 |
| miR-190b | 63 | 66 | | 103 | 84 |
| miR-3157 | 51 | 46 | 62 | 66 | 78 |
| miR-182 | 69 | 65 | 46 | 93 | 67 |
| miR-193a-3P | 54 | | 90 | | 79 |
| miR-610 | 78 | | 71 | | 91 |
| miR-18b | 94 | 89 | | | 55 |
| Neg control scr miRNA Ambion #2 | 93 | 95 | 96 | 102 | 97 |
| Neg control siRNA pool | 100 | 100 | 100 | 100 | 100 |
| Positive control siBRAF | 36 | 50 | 57 | 79 | 85 |

TABLE 11

Percentage inhibition of cell viability in A375 cells after lentiviral transduction with miRNAs listed in Table 1 and 7. The decrease of cell viability of HUVEC cells after lentiviral transduction is depicted by relative absorbance change. The absorbance at 490 nM was normalized to 1.0 for the empty vector.

| Lentivirus | A375 % inhibition compared to Empty vector | HUVEC Relative absorbance change (MOI 200) |
| --- | --- | --- |
| Empty vector | 0.0 | 1.0 |
| hsa-mir-203 | 24.2 | Not active |
| hsa-mir-16 | 26.7 | Not active |
| hsa-mir-184 | 30.4 | Not active |
| hsa-mir-18b | 18.7 | Not active |
| hsa-mir-133a | 18.7 | Not active |
| hsa-mir-509 | 16.6 | Not active |
| hsa-mir-497 | 39.3 | Not active |
| hsa-mir-96 | 34.0 | Not active |
| hsa-mir-95 | 20.7 | Not active |
| hsa-mir-10b | 26.3 | Not active |
| hsa-mir-128-1 | 26.5 | Not active |
| hsa-mir-128-2 | 23.2 | Not active |
| hsa-mir-129 | 30.2 | Not active |
| hsa-mir-3157 | 38.3* | Not active |
| hsa-mir-182 | 27.2 | Not active |
| hsa-mir-193a-3P | 23.8 | Not active |
| hsa-mir-610 | 18.8* | Not active |

*Data obtained in separate experiment

REFERENCE LIST

Davies, H. et al. Mutations of the BRAF gene in human cancer. Nature 417: 949, 2002.
Houben, R. at al. Constitutive activation of the Ras-Raf signalling pathway in metastatic melanoma is associated with poor prognosis. J. Carcinog. 3: 6, 2004.
Giard, D. J. et al. In vitro cultivation of human tumors: establishment of cell lines derived from a series of solid tumors. J. Natl. Cancer Inst. 51, 1417, 1973
Ikenoue, T. et al. Functional analysis of mutations within the kinase activation segment of BRAF in human colorectal tumors. Cancer res. 63: 8132, 2003
Ikenoue, T., et al. Different effects of point mutations within the BRAF glycine-rich loop in colorectal tumors on mitogen-activated protein/extracellular signal-regulated kinase kinase/extracellular signal-regulated kinase and nuclear factor κB pathway and cellular transformation. Cancer res. 64: 3428, 2004.
Hingorani, S. R., et al. Suppression of BRAF (V599E) in human melanoma abrogates tarnsformation. Cancer res. 63: 5198, 2003.
Karasarides, M. et al. BRAF is a therapeutic target in melanoma. Oncogene 23: 6292, 2004.
Pfaffl M. W. et al. Nucleic Acids Res. 29: e45 (2001)

Abbreviations miR, miRNA—microRNA
Hsa-miR—precursor of miR
MOI—multiplicity of infection
MTT—(3-(4,5-Dimethylthiazol-2-yl)-2,5-diphenyltetrazolium bromide
qPCR—quantitative PCR
CGH—Comparative Genomic Hybridization
PVDF—Polyvinylidene difluoride
HUVEC—Human umbilical vein endothelial cells

---

The invention claimed is:

1. A method for inhibiting growth and/or reducing viability of melanoma cells, the method comprising: administering to said cells an effective amount of at least one miRNA molecule or a composition comprising an effective amount of said at least one miRNA molecule, wherein said at least one miRNA molecule is selected from the group consisting of:

an miRNA molecule from 6 to 30 nucleotides comprising at least 6 of the nucleotides present in a seed sequence selected from the group consisting of SEQ ID NOs:160 and 161 and having at least 70% identity with SEQ ID NO:99 or 100 (miRNA-10b), an miRNA molecule from 6 to 30 nucleotides comprising at least 6 of the nucleotides present in a seed sequence selected from the group consisting of SEQ ID NOs:162 and 163 and having at least 70% identity with SEQ ID NO:101 or 102 (miRNA-18b), an miRNA molecule from 6 to 30 nucleotides comprising at least 6 of the nucleotides present in seed sequence SEQ ID NO:166 and having at least 70% identity with SEQ ID NO:105 (miRNA-128), an miRNA molecule from 6 to 30 nucleotides comprising at least 6 of the nucleotides present in seed sequence SEQ ID NO:170 and having at least 70% identity with SEQ ID NO:109 (miRNA-184), an miRNA molecule from 6 to 30 nucleotides comprising at least 6 of the nucleotides present in seed sequence SEQ ID NO:171 and having at least 70% identity with SEQ ID NO:110 (miRNA-190b), an miRNA molecule from 6 to 30 nucleotides comprising at least 6 of the nucleotides present in seed sequence SEQ ID NO:173 and having at least 70% identity with SEQ ID NO:112 (miRNA-3157), an miRNA molecule from 6 to 30 nucleotides comprising at least 6 of the nucleotides present in a seed sequence selected from the group consisting of SEQ ID NOs: 157, 158 and 159 and having at least 70% identity with SEQ ID NO:96, 97 or 98 (miRNA-7) and/or a precursor of said miRNA molecule.

2. The method of claim 1, wherein said composition further comprises an miRNA molecule, isomiR, or precursor thereof, selected from the group consisting of:

a) at least one of miRNA-137, Let-7, and Let-7a, and/or an isomiR or a precursor thereof and/or, b) at least one antagomir of miRNA-221 and/or miRNA-222, and/or a precursor thereof.

3. The method of claim 1, wherein said at least one miRNA molecule is an miRNA-7 molecule or an isomiR thereof or a precursor thereof.

4. The method of claim 1, wherein a precursor of said miRNA is administered.

5. The method of claim 1, wherein an isomiR of said miRNA is administered.

6. The method of claim 1, wherein the miRNA molecule is a modified miRNA molecule.

7. A method for inhibiting growth and/or reducing viability of melanoma cells, said method comprising: administering to said cells an effective amount of at least one miRNA molecule or a composition comprising an effective amount of said at least one miRNA molecule, wherein said at least one miRNA molecule is selected from the group consisting of:

an miRNA molecule from 6 to 30 nucleotides comprising at least 6 of the nucleotides present in seed sequence SEQ ID NO:190 and having at least 70% identity with SEQ ID NO:129 (miRNA-610), an miRNA molecule from 6 to 30 nucleotides comprising at least 6 of the nucleotides present in seed sequence SEQ ID NO:185 and having at least 70% identity with SEQ ID NO:124 (miRNA-95), and/or a precursor of said miRNA molecule.

8. The method according to claim 7, wherein said composition further comprises an miRNA molecule, isomiR, or precursor thereof, selected from the group consisting of:

a) at least one of miRNA-137, Let-7, and Let-7a, and/or an isomiR or a precursor thereof and/or,
b) at least one antagomir of miRNA-221 and/or miRNA-222, and/or a precursor thereof.

9. The method according to claim 7, wherein a precursor of said miRNA is administered.

10. The method according to claim 7, wherein an isomiR of said miRNA is administered.

11. The method according to claim 7, wherein the miRNA molecule is a modified miRNA molecule.

12. A method for inhibiting growth and/or reducing viability of melanoma cells, said method comprising: administering to said cells an effective amount of an miRNA molecule from 6 to 30 nucleotides comprising at least 6 of the nucleotides present in seed sequence SEQ ID NO:188 and having at least 70% identity with SEQ ID NO: 127 (miRNA-193a) and/or a precursor of said miRNA molecule or a composition comprising an effective amount of said miRNA molecule and/or said precursor of said miRNA molecule.

13. The method according to claim 12, wherein said composition further comprises an miRNA molecule, isomiR, or precursor thereof, selected from the group consisting of:
a) at least one of miRNA-137, Let-7, and Let-7a, and/or an isomiR or a precursor thereof and/or,
b) at least one antagomir of miRNA-221 and/or miRNA-222, and/or a precursor thereof.

14. The method according to claim 12, wherein a precursor of said miRNA is administered.

15. The method according to claim 12, wherein an isomiR of said miRNA is administered.

16. The method according to claim 12, wherein the miRNA molecule is a modified miRNA molecule.

* * * * *

SEQUENCE LISTING

```
<160> NUMBER OF SEQ ID NOS: 296

<210> SEQ ID NO 1
<211> LENGTH: 23
<212> TYPE: DNA
<213> ORGANISM: Artificial sequence
<220> FEATURE:
<223> OTHER INFORMATION: pCDH specific primer

<400> SEQUENCE: 1
cacgctgttt tgacctccat aga                                            23

<210> SEQ ID NO 2
<211> LENGTH: 18
<212> TYPE: DNA
<213> ORGANISM: Artificial sequence
<220> FEATURE:
<223> OTHER INFORMATION: pCDH specific primer

<400> SEQUENCE: 2
cactgacggg caccggag                                                  18

<210> SEQ ID NO 3
<211> LENGTH: 28
<212> TYPE: DNA
<213> ORGANISM: Artificial sequence
<220> FEATURE:
<223> OTHER INFORMATION: pCDH specific primer

<400> SEQUENCE: 3
```

```
gacctccata gaagattcta gagctagc                                              28

<210> SEQ ID NO 4
<211> LENGTH: 49
<212> TYPE: DNA
<213> ORGANISM: Artificial sequence
<220> FEATURE:
<223> OTHER INFORMATION: PCR primer

<400> SEQUENCE: 4
gtcgtatcca gtgcagggtc cgaggtattc gcactggata cgaacaaca                       49

<210> SEQ ID NO 5
<211> LENGTH: 26
<212> TYPE: DNA
<213> ORGANISM: Artificial sequence
<220> FEATURE:
<223> OTHER INFORMATION: PCR primer

<400> SEQUENCE: 5
gcccgcttgg aagactagtg attttg                                                26

<210> SEQ ID NO 6
<211> LENGTH: 49
<212> TYPE: DNA
<213> ORGANISM: Artificial sequence
<220> FEATURE:
<223> OTHER INFORMATION: PCR primer

<400> SEQUENCE: 6
gtcgtatcca gtgcagggtc cgaggtattc gcactggata cgacacaaa                       49

<210> SEQ ID NO 7
<211> LENGTH: 26
<212> TYPE: DNA
<213> ORGANISM: Artificial sequence
<220> FEATURE:
<223> OTHER INFORMATION: PCR primer

<400> SEQUENCE: 7
gcccgcttac cctgtagaac cgaatt                                                26

<210> SEQ ID NO 8
<211> LENGTH: 49
<212> TYPE: DNA
<213> ORGANISM: Artificial sequence
<220> FEATURE:
<223> OTHER INFORMATION: PCR primer

<400> SEQUENCE: 8
gtcgtatcca gtgcagggtc cgaggtattc gcactggata cgaattccc                       49

<210> SEQ ID NO 9
<211> LENGTH: 25
<212> TYPE: DNA
<213> ORGANISM: Artificial sequence
<220> FEATURE:
<223> OTHER INFORMATION: PCR primer

<400> SEQUENCE: 9
gcccgctaca gattcgattc taggg                                                 25

<210> SEQ ID NO 10
<211> LENGTH: 49
<212> TYPE: DNA
<213> ORGANISM: Artificial sequence
```

```
<220> FEATURE:
<223> OTHER INFORMATION: PCR primer

<400> SEQUENCE: 10
gtcgtatcca gtgcagggtc cgaggtattc gcactggata cgactaact            49

<210> SEQ ID NO 11
<211> LENGTH: 26
<212> TYPE: DNA
<213> ORGANISM: Artificial sequence
<220> FEATURE:
<223> OTHER INFORMATION: PCR primer

<400> SEQUENCE: 11
gcccgcttaa ggtgcatcta gtgcag                                     26

<210> SEQ ID NO 12
<211> LENGTH: 49
<212> TYPE: DNA
<213> ORGANISM: Artificial sequence
<220> FEATURE:
<223> OTHER INFORMATION: PCR primer

<400> SEQUENCE: 12
gtcgtatcca gtgcagggtc cgaggtattc gcactggata cgagccaga            49

<210> SEQ ID NO 13
<211> LENGTH: 25
<212> TYPE: DNA
<213> ORGANISM: Artificial sequence
<220> FEATURE:
<223> OTHER INFORMATION: PCR primer

<400> SEQUENCE: 13
gcccgcttgc cctaaatgcc ccttc                                      25

<210> SEQ ID NO 14
<211> LENGTH: 49
<212> TYPE: DNA
<213> ORGANISM: Artificial sequence
<220> FEATURE:
<223> OTHER INFORMATION: PCR primer

<400> SEQUENCE: 14
gtcgtatcca gtgcagggtc cgaggtattc gcactggata cgaagcaaa            49

<210> SEQ ID NO 15
<211> LENGTH: 26
<212> TYPE: DNA
<213> ORGANISM: Artificial sequence
<220> FEATURE:
<223> OTHER INFORMATION: PCR primer

<400> SEQUENCE: 15
gcccgctttt ggcactagca catttt                                     26

<210> SEQ ID NO 16
<211> LENGTH: 51
<212> TYPE: DNA
<213> ORGANISM: Artificial sequence
<220> FEATURE:
<223> OTHER INFORMATION: PCR primer

<400> SEQUENCE: 16
gtcgtatcca gtgcagggtc cgaggtaatt cgcactggat acgaccaaaa a         51
```

<210> SEQ ID NO 17
<211> LENGTH: 23
<212> TYPE: DNA
<213> ORGANISM: Artificial sequence
<220> FEATURE:
<223> OTHER INFORMATION: PCR primer

<400> SEQUENCE: 17
tgccagtttg gcactagcac att                                          23

<210> SEQ ID NO 18
<211> LENGTH: 48
<212> TYPE: DNA
<213> ORGANISM: Artificial sequence
<220> FEATURE:
<223> OTHER INFORMATION: PCR primer

<400> SEQUENCE: 18
gtcgtatcca gtgcagggtc cgaggtattc gcactggata cgaaaaga               48

<210> SEQ ID NO 19
<211> LENGTH: 24
<212> TYPE: DNA
<213> ORGANISM: Artificial sequence
<220> FEATURE:
<223> OTHER INFORMATION: PCR primer

<400> SEQUENCE: 19
gcccgcttca cagtgaaccg gtct                                         24

<210> SEQ ID NO 20
<211> LENGTH: 51
<212> TYPE: DNA
<213> ORGANISM: Artificial sequence
<220> FEATURE:
<223> OTHER INFORMATION: PCR primer

<400> SEQUENCE: 20
gtcgtatcca gtgcagggtc cgaggtaatt cgcactggat acgacgaaag a           51

<210> SEQ ID NO 21
<211> LENGTH: 24
<212> TYPE: DNA
<213> ORGANISM: Artificial sequence
<220> FEATURE:
<223> OTHER INFORMATION: PCR primer

<400> SEQUENCE: 21
tgccagtcac agtgaaccgg tctc                                         24

<210> SEQ ID NO 22
<211> LENGTH: 48
<212> TYPE: DNA
<213> ORGANISM: Artificial sequence
<220> FEATURE:
<223> OTHER INFORMATION: PCR primer

<400> SEQUENCE: 22
gtcgtatcca gtgcagggtc cgaggtattc gcactggata cgaaaaga               48

<210> SEQ ID NO 23
<211> LENGTH: 24
<212> TYPE: DNA
<213> ORGANISM: Artificial sequence
<220> FEATURE:
<223> OTHER INFORMATION: PCR primer

<400> SEQUENCE: 23
gcccgcttca cagtgaaccg gtct                                          24

<210> SEQ ID NO 24
<211> LENGTH: 51
<212> TYPE: DNA
<213> ORGANISM: Artificial sequence
<220> FEATURE:
<223> OTHER INFORMATION: PCR primer

<400> SEQUENCE: 24
gtcgtatcca gtgcagggtc cgaggtaatt cgcactggat acgacaagag a            51

<210> SEQ ID NO 25
<211> LENGTH: 22
<212> TYPE: DNA
<213> ORGANISM: Artificial sequence
<220> FEATURE:
<223> OTHER INFORMATION: PCR primer

<400> SEQUENCE: 25
tgccagtcac agtgaaccgg tc                                            22

<210> SEQ ID NO 26
<211> LENGTH: 49
<212> TYPE: DNA
<213> ORGANISM: Artificial sequence
<220> FEATURE:
<223> OTHER INFORMATION: PCR primer

<400> SEQUENCE: 26
gtcgtatcca gtgcagggtc cgaggtattc gcactggata cgagcaagc               49

<210> SEQ ID NO 27
<211> LENGTH: 23
<212> TYPE: DNA
<213> ORGANISM: Artificial sequence
<220> FEATURE:
<223> OTHER INFORMATION: PCR primer

<400> SEQUENCE: 27 tgccagctt ttgcggtctg ggc                                            23

<210> SEQ ID NO 28
<211> LENGTH: 49
<212> TYPE: DNA
<213> ORGANISM: Artificial sequence
<220> FEATURE:
<223> OTHER INFORMATION: PCR primer

<400> SEQUENCE: 28
gtcgtatcca gtgcagggtc cgaggtattc gcactggata cgaaccctt               49

<210> SEQ ID NO 29
<211> LENGTH: 25
<212> TYPE: DNA
<213> ORGANISM: Artificial sequence
<220> FEATURE:
<223> OTHER INFORMATION: PCR primer

<400> SEQUENCE: 29
gcccgcttgg acggagaact gataa                                         25

<210> SEQ ID NO 30

<211> LENGTH: 49
<212> TYPE: DNA
<213> ORGANISM: Artificial sequence
<220> FEATURE:
<223> OTHER INFORMATION: PCR primer

<400> SEQUENCE: 30
gtcgtatcca gtgcagggtc cgaggtattc gcactggata cgaaaccca          49

<210> SEQ ID NO 31
<211> LENGTH: 24
<212> TYPE: DNA
<213> ORGANISM: Artificial sequence
<220> FEATURE:
<223> OTHER INFORMATION: PCR primer

<400> SEQUENCE: 31
gcccgcttga tatgtttgat attg          24

<210> SEQ ID NO 32
<211> LENGTH: 49
<212> TYPE: DNA
<213> ORGANISM: Artificial sequence
<220> FEATURE:
<223> OTHER INFORMATION: PCR primer

<400> SEQUENCE: 32
gtcgtatcca gtgcagggtc cgaggtattc gcactggata cgactagtg          49

<210> SEQ ID NO 33
<211> LENGTH: 25
<212> TYPE: DNA
<213> ORGANISM: Artificial sequence
<220> FEATURE:
<223> OTHER INFORMATION: PCR primer

<400> SEQUENCE: 33
gcccgctgtg aaatgtttag gacca          25

<210> SEQ ID NO 34
<211> LENGTH: 51
<212> TYPE: DNA
<213> ORGANISM: Artificial sequence
<220> FEATURE:
<223> OTHER INFORMATION: PCR primer

<400> SEQUENCE: 34
gtcgtatcca gtgcagggtc cgaggtaatt cgcactggat acgacagact g          51

<210> SEQ ID NO 35
<211> LENGTH: 24
<212> TYPE: DNA
<213> ORGANISM: Artificial sequence
<220> FEATURE:
<223> OTHER INFORMATION: PCR primer

<400> SEQUENCE: 35
tgccagttca gccaggctag tgca          24

<210> SEQ ID NO 36
<211> LENGTH: 50
<212> TYPE: DNA
<213> ORGANISM: Artificial sequence
<220> FEATURE:
<223> OTHER INFORMATION: PCR primer

<400> SEQUENCE: 36

-continued gtcgtatcca gtgcagggtc cgaggtattc gcactggata cgaccgccaa                    50

<210> SEQ ID NO 37
<211> LENGTH: 24
<212> TYPE: DNA
<213> ORGANISM: Artificial sequence
<220> FEATURE:
<223> OTHER INFORMATION: PCR primer

<400> SEQUENCE: 37
gcccgcccaa tattactgtg ctgc                                                24

<210> SEQ ID NO 38
<211> LENGTH: 50
<212> TYPE: DNA
<213> ORGANISM: Artificial sequence
<220> FEATURE:
<223> OTHER INFORMATION: PCR primer

<400> SEQUENCE: 38
gtcgtatcca gtgcagggtc cgaggtattc gcactggata cgaccagctg                    50

<210> SEQ ID NO 39
<211> LENGTH: 24
<212> TYPE: DNA
<213> ORGANISM: Artificial sequence
<220> FEATURE:
<223> OTHER INFORMATION: PCR primer

<400> SEQUENCE: 39
gcccgctttg gtccccttca acca                                                24

<210> SEQ ID NO 40
<211> LENGTH: 50
<212> TYPE: DNA
<213> ORGANISM: Artificial sequence
<220> FEATURE:
<223> OTHER INFORMATION: PCR primer

<400> SEQUENCE: 40
gtcgtatcca gtgcagggtc cgaggtattc gcactggata cgacctaccc                    50

<210> SEQ ID NO 41
<211> LENGTH: 24
<212> TYPE: DNA
<213> ORGANISM: Artificial sequence
<220> FEATURE:
<223> OTHER INFORMATION: PCR primer

<400> SEQUENCE: 41
tgccagtgat tggtacgtct gtgg                                                24

<210> SEQ ID NO 42
<211> LENGTH: 50
<212> TYPE: DNA
<213> ORGANISM: Artificial sequence
<220> FEATURE:
<223> OTHER INFORMATION: PCR primer

<400> SEQUENCE: 42
gtcgtatcca gtgcagggtc cgaggtattc gcactggata cgactgattg                    50

<210> SEQ ID NO 43
<211> LENGTH: 23
<212> TYPE: DNA

```
<213> ORGANISM: Artificial sequence
<220> FEATURE:
<223> OTHER INFORMATION: PCR primer

<400> SEQUENCE: 43
tgccagtact gcagacagtg gca                                           23

<210> SEQ ID NO 44
<211> LENGTH: 50
<212> TYPE: DNA
<213> ORGANISM: Artificial sequence
<220> FEATURE:
<223> OTHER INFORMATION: PCR primer

<400> SEQUENCE: 44
gtcgtatcca gtgcagggtc cgaggtattc gcactggata cgacacaaac              50

<210> SEQ ID NO 45
<211> LENGTH: 23
<212> TYPE: DNA
<213> ORGANISM: Artificial sequence
<220> FEATURE:
<223> OTHER INFORMATION: PCR primer

<400> SEQUENCE: 45
tgccagcagc agcacactgt ggt                                           23

<210> SEQ ID NO 46
<211> LENGTH: 50
<212> TYPE: DNA
<213> ORGANISM: Artificial sequence
<220> FEATURE:
<223> OTHER INFORMATION: PCR primer

<400> SEQUENCE: 46
gtcgtatcca gtgcagggtc cgaggtattc gcactggata cgacccaaac              50

<210> SEQ ID NO 47
<211> LENGTH: 24
<212> TYPE: DNA
<213> ORGANISM: Artificial sequence
<220> FEATURE:
<223> OTHER INFORMATION: PCR primer

<400> SEQUENCE: 47
tgccagcgtc ttacccagca gtgt                                          24

<210> SEQ ID NO 48
<211> LENGTH: 50
<212> TYPE: DNA
<213> ORGANISM: Artificial sequence
<220> FEATURE:
<223> OTHER INFORMATION: PCR primer

<400> SEQUENCE: 48
gtcgtatcca gtgcagggtc cgaggtattc gcactggata cgactgctca              50

<210> SEQ ID NO 49
<211> LENGTH: 24
<212> TYPE: DNA
<213> ORGANISM: Artificial sequence
<220> FEATURE:
<223> OTHER INFORMATION: PCR primer

<400> SEQUENCE: 49
tgccagttca acgggtattt attg                                          24
```

<210> SEQ ID NO 50
<211> LENGTH: 50
<212> TYPE: DNA
<213> ORGANISM: Artificial sequence
<220> FEATURE:
<223> OTHER INFORMATION: PCR primer

<400> SEQUENCE: 50
gtcgtatcca gtgcagggtc cgaggtattc gcactggata cgacagtgtg         50

<210> SEQ ID NO 51
<211> LENGTH: 24
<212> TYPE: DNA
<213> ORGANISM: Artificial sequence
<220> FEATURE:
<223> OTHER INFORMATION: PCR primer

<400> SEQUENCE: 51
gcccgctttg gcaatggtag aact         24

<210> SEQ ID NO 52
<211> LENGTH: 50
<212> TYPE: DNA
<213> ORGANISM: Artificial sequence
<220> FEATURE:
<223> OTHER INFORMATION: PCR primer

<400> SEQUENCE: 52
gtcgtatcca gtgcagggtc cgaggtattc gcactggata cgacactggg         50

<210> SEQ ID NO 53
<211> LENGTH: 24
<212> TYPE: DNA
<213> ORGANISM: Artificial sequence
<220> FEATURE:
<223> OTHER INFORMATION: PCR primer

<400> SEQUENCE: 53
tgccagaact ggcctacaaa gtcc         24

<210> SEQ ID NO 54
<211> LENGTH: 50
<212> TYPE: DNA
<213> ORGANISM: Artificial sequence
<220> FEATURE:
<223> OTHER INFORMATION: PCR primer

<400> SEQUENCE: 54
gtcgtatcca gtgcagggtc cgaggtattc gcactggata cgactcccag         50

<210> SEQ ID NO 55
<211> LENGTH: 23
<212> TYPE: DNA
<213> ORGANISM: Artificial sequence
<220> FEATURE:
<223> OTHER INFORMATION: PCR primer

<400> SEQUENCE: 55
tgccagtgag ctaaatgtgt gct         23

<210> SEQ ID NO 56
<211> LENGTH: 49
<212> TYPE: DNA
<213> ORGANISM: Artificial sequence
<220> FEATURE:

<223> OTHER INFORMATION: PCR primer

<400> SEQUENCE: 56
gtcgtatcca gtgcagggtc cgaggtattc gcactggata cgaattccc          49

<210> SEQ ID NO 57
<211> LENGTH: 24
<212> TYPE: DNA
<213> ORGANISM: Artificial sequence
<220> FEATURE:
<223> OTHER INFORMATION: PCR primer

<400> SEQUENCE: 57
gcccgcacag attcgattct aggg                                     24

<210> SEQ ID NO 58
<211> LENGTH: 16
<212> TYPE: DNA
<213> ORGANISM: Artificial sequence
<220> FEATURE:
<223> OTHER INFORMATION: PCR primer

<400> SEQUENCE: 58
gtgcagggtc cgaggt                                              16

<210> SEQ ID NO 59
<211> LENGTH: 16
<212> TYPE: DNA
<213> ORGANISM: Artificial sequence
<220> FEATURE:
<223> OTHER INFORMATION: PCR primer

<400> SEQUENCE: 59
gtcatccttg cgcagg                                              16

<210> SEQ ID NO 60
<211> LENGTH: 20
<212> TYPE: DNA
<213> ORGANISM: Artificial sequence
<220> FEATURE:
<223> OTHER INFORMATION: PCR primer

<400> SEQUENCE: 60
cgcttcggca gcacatatac                                          20

<210> SEQ ID NO 61
<211> LENGTH: 20
<212> TYPE: DNA
<213> ORGANISM: Artificial sequence
<220> FEATURE:
<223> OTHER INFORMATION: PCR primer

<400> SEQUENCE: 61
aggggccatg ctaatcttct                                          20

<210> SEQ ID NO 62
<211> LENGTH: 23
<212> TYPE: DNA
<213> ORGANISM: Artificial sequence
<220> FEATURE:
<223> OTHER INFORMATION: PCR primer

<400> SEQUENCE: 62
cacgctgttt tgacctccat aga                                      23

```
<210> SEQ ID NO 63
<211> LENGTH: 18
<212> TYPE: DNA
<213> ORGANISM: Artificial sequence
<220> FEATURE:
<223> OTHER INFORMATION: PCR primer

<400> SEQUENCE: 63
cactgacggg caccggag                                                    18

<210> SEQ ID NO 64
<211> LENGTH: 19
<212> TYPE: RNA
<213> ORGANISM: Artificial sequence
<220> FEATURE:
<223> OTHER INFORMATION: BRAF siRNA

<400> SEQUENCE: 64
caugaagacc ucacaguaa                                                   19

<210> SEQ ID NO 65
<211> LENGTH: 19
<212> TYPE: RNA
<213> ORGANISM: Artificial sequence
<220> FEATURE:
<223> OTHER INFORMATION: BRAF siRNA

<400> SEQUENCE: 65
ucaguaaggu acggaguaa                                                   19

<210> SEQ ID NO 66
<211> LENGTH: 19
<212> TYPE: RNA
<213> ORGANISM: Artificial sequence
<220> FEATURE:
<223> OTHER INFORMATION: BRAF siRNA

<400> SEQUENCE: 66
agacgggacu cgagugaug                                                   19

<210> SEQ ID NO 67
<211> LENGTH: 19
<212> TYPE: RNA
<213> ORGANISM: Artificial sequence
<220> FEATURE:
<223> OTHER INFORMATION: BRAF siRNA

<400> SEQUENCE: 67
uuaccuggcu cacuaacua                                                   19

<210> SEQ ID NO 68
<211> LENGTH: 21
<212> TYPE: DNA
<213> ORGANISM: Artificial sequence
<220> FEATURE:
<223> OTHER INFORMATION: scrambled miRNA mimic

<400> SEQUENCE: 68
uguacugcuu acgauucggt t                                                21

<210> SEQ ID NO 69
<211> LENGTH: 110
<212> TYPE: RNA
<213> ORGANISM: Artificial sequence
<220> FEATURE:
<223> OTHER INFORMATION: Precursor sequence
```

-continued

```
<400> SEQUENCE: 69
uuggauguug gccuaguucu guguggaaga cuagugauuu uguuguuuuu agauaacuaa    60
aucgacaaca aaucacaguc ugccauaugg cacaggccau gccucuacag              110

<210> SEQ ID NO 70
<211> LENGTH: 110
<212> TYPE: RNA
<213> ORGANISM: Artificial sequence
<220> FEATURE:
<223> OTHER INFORMATION: Precursor sequence

<400> SEQUENCE: 70
cuggauacag aguggaccgg cuggccccau cuggaagacu agugauuuug uuguugucuu    60
acugcgcuca acaacaaauc ccagucuacc uaauggugcc agccaucgca              110

<210> SEQ ID NO 71
<211> LENGTH: 110
<212> TYPE: RNA
<213> ORGANISM: Artificial sequence
<220> FEATURE:
<223> OTHER INFORMATION: Precursor sequence

<400> SEQUENCE: 71
agauuagagu ggcugugguc uagugcugug uggaagacua gugauuuugu uguucugaug    60
uacuacgaca acaagucaca gccggccuca uagcgcagac ucccuucgac              110

<210> SEQ ID NO 72
<211> LENGTH: 110
<212> TYPE: RNA
<213> ORGANISM: Artificial sequence
<220> FEATURE:
<223> OTHER INFORMATION: Precursor sequence

<400> SEQUENCE: 72
ccagagguug uaacguuguc uauauauacc cuguagaacc gaauuugugu gguauccgua    60
uagucacaga uucgauucua ggggaauaua uggucgaugc aaaaacuuca              110

<210> SEQ ID NO 73
<211> LENGTH: 71
<212> TYPE: RNA
<213> ORGANISM: Artificial sequence
<220> FEATURE:
<223> OTHER INFORMATION: Precursor sequence

<400> SEQUENCE: 73
uguguuaagg ugcaucuagu gcaguuagug aagcagcuua gaaucuacug cccuaaaugc    60
cccuucuggc a                                                        71

<210> SEQ ID NO 74
<211> LENGTH: 78
<212> TYPE: RNA
<213> ORGANISM: Artificial sequence
<220> FEATURE:
<223> OTHER INFORMATION: Precursor sequence

<400> SEQUENCE: 74
uggccgauuu uggcacuagc acauuuugc uugugucucu ccgcucugag caaucaugug     60
cagugccaau augggaaa                                                 78

<210> SEQ ID NO 75
<211> LENGTH: 82
```

<212> TYPE: RNA
<213> ORGANISM: Artificial sequence
<220> FEATURE:
<223> OTHER INFORMATION: Precursor sequence

<400> SEQUENCE: 75
ugagcuguug gauucggggc cguagcacug ucugagaggu uuacauuucu cacagugaac    60
cggucucuuu uucagcugcu uc                                            82

<210> SEQ ID NO 76
<211> LENGTH: 84
<212> TYPE: RNA
<213> ORGANISM: Artificial sequence
<220> FEATURE:
<223> OTHER INFORMATION: Precursor sequence

<400> SEQUENCE: 76
ugugcagugg gaagggggc cgauacacug uacgagagug aguagcaggu cucacaguga    60
accggucucu uucccuacug uguc                                          84

<210> SEQ ID NO 77
<211> LENGTH: 72
<212> TYPE: RNA
<213> ORGANISM: Artificial sequence
<220> FEATURE:
<223> OTHER INFORMATION: Precursor sequence

<400> SEQUENCE: 77
ggaucuuuuu gcggucuggg cuugcuguuc cucucaacag uagucaggaa gcccuuaccc    60
caaaaaguau cu                                                       72

<210> SEQ ID NO 78
<211> LENGTH: 90
<212> TYPE: RNA
<213> ORGANISM: Artificial sequence
<220> FEATURE:
<223> OTHER INFORMATION: Precursor sequence

<400> SEQUENCE: 78
ugcccuucgc gaaucuuuuu gcggucuggg cuugcuguac auaacucaau agccggaagc    60
ccuuacccca aaaagcauuu gcggagggcg                                    90

<210> SEQ ID NO 79
<211> LENGTH: 84
<212> TYPE: RNA
<213> ORGANISM: Artificial sequence
<220> FEATURE:
<223> OTHER INFORMATION: Precursor sequence

<400> SEQUENCE: 79
ccagucacgu ccccuuauca cuuuuccagc ccagcuuugu gacuguaagu guuggacgga    60
gaacugauaa ggguaggguga uuga                                         84

<210> SEQ ID NO 80
<211> LENGTH: 79
<212> TYPE: RNA
<213> ORGANISM: Artificial sequence
<220> FEATURE:
<223> OTHER INFORMATION: Precursor sequence

<400> SEQUENCE: 80
ugcuucugug ugauauguuu gauauugggu uguuuaauua ggaaccaacu aaaugucaaa    60
cauauucuua cagcagcag                                                        79

<210> SEQ ID NO 81
<211> LENGTH: 110
<212> TYPE: RNA
<213> ORGANISM: Artificial sequence
<220> FEATURE:
<223> OTHER INFORMATION: Precursor sequence

<400> SEQUENCE: 81
guguugggga cucgcgcgcu ggguccagug guucuuaaca guucaacagu ucuguagcgc    60 aaugugaaa uguuuaggac cacuagaccc ggcgggcgcg gcgacagcga                110

<210> SEQ ID NO 82
<211> LENGTH: 85
<212> TYPE: RNA
<213> ORGANISM: Artificial sequence
<220> FEATURE:
<223> OTHER INFORMATION: Precursor sequence

<400> SEQUENCE: 82
gggaagggcu ucagccaggc uagugcaguc ugcuugugc caacacuggg gugaugacug    60
cccuagucua gcugaagcuu uuccc                                          85

<210> SEQ ID NO 83
<211> LENGTH: 89
<212> TYPE: RNA
<213> ORGANISM: Artificial sequence
<220> FEATURE:
<223> OTHER INFORMATION: Precursor sequence

<400> SEQUENCE: 83
gucagcagug ccuuagcagc acguaaauau uggcguuaag auucuaaaau uaucuccagu    60
auuaacugug cugcugaagu aagguugac                                      89

<210> SEQ ID NO 84
<211> LENGTH: 81
<212> TYPE: RNA
<213> ORGANISM: Artificial sequence
<220> FEATURE:
<223> OTHER INFORMATION: Precursor sequence

<400> SEQUENCE: 84
guuccacucu agcagcacgu aaauauuggc guagugaaau auauauuaaa caccaauauu    60
acugugcugc uuuaguguga c                                              81

<210> SEQ ID NO 85
<211> LENGTH: 88
<212> TYPE: RNA
<213> ORGANISM: Artificial sequence
<220> FEATURE:
<223> OTHER INFORMATION: Precursor sequence

<400> SEQUENCE: 85
acaaugcuuu gcuagagcug guaaaaugga accaaaucgc cucuucaaug gauuuggucc    60
ccuucaacca gcuguagcua ugcauuga                                       88

<210> SEQ ID NO 86
<211> LENGTH: 102
<212> TYPE: RNA
<213> ORGANISM: Artificial sequence
<220> FEATURE:
<223> OTHER INFORMATION: Precursor sequence

<400> SEQUENCE: 86
gggagccaaa ugcuuugcua gagcugguaa aauggaacca aaucgacugu ccaauggauu    60 uggucccuu caaccagcug uagcugugca uugauggcgc cg    102

<210> SEQ ID NO 87
<211> LENGTH: 94
<212> TYPE: RNA
<213> ORGANISM: Artificial sequence
<220> FEATURE:
<223> OTHER INFORMATION: Precursor sequence

<400> SEQUENCE: 87
caugcugugu gugguacccu acugcagaca guggcaauca uguauaauua aaaaugauug    60
guacgucugu ggguagagua cugcaugaca caug    94

<210> SEQ ID NO 88
<211> LENGTH: 91
<212> TYPE: RNA
<213> ORGANISM: Artificial sequence
<220> FEATURE:
<223> OTHER INFORMATION: Precursor sequence

<400> SEQUENCE: 88
caugcugugu gugguacccu acugcagaca guggcaauca uguauaauua aaaaugauug    60
guacgucugu ggguagagua cugcaugaca c    91

<210> SEQ ID NO 89
<211> LENGTH: 75
<212> TYPE: RNA
<213> ORGANISM: Artificial sequence
<220> FEATURE:
<223> OTHER INFORMATION: Precursor sequence

<400> SEQUENCE: 89
gugguacccu acugcagacg uggcaaucau guauaauuaa aaaugauugg uacgucugug    60
gguagaguac ugcau    75

<210> SEQ ID NO 90
<211> LENGTH: 112
<212> TYPE: RNA
<213> ORGANISM: Artificial sequence
<220> FEATURE:
<223> OTHER INFORMATION: Precursor sequence

<400> SEQUENCE: 90
ccaccccggu ccugcucccg ccccagcagc acacuguggu uugacggca cuguggccac    60 guccaaacca cacuguggug uuagagcgag ggugggggag gcaccgccga gg    112

<210> SEQ ID NO 91
<211> LENGTH: 68
<212> TYPE: RNA
<213> ORGANISM: Artificial sequence
<220> FEATURE:
<223> OTHER INFORMATION: Precursor sequence

<400> SEQUENCE: 91
cccucgucuu acccagcagu guuuggugc gguugggagu cucuaauacu gccgggauau    60
gauggagg    68

<210> SEQ ID NO 92

```
<211> LENGTH: 81
<212> TYPE: RNA
<213> ORGANISM: Artificial sequence
<220> FEATURE:
<223> OTHER INFORMATION: Precursor sequence

<400> SEQUENCE: 92
aacacagugg gcacucaaua aaugucuguu gaauugaaau gcguuacauu caacggguau    60
uuauugagca cccacucugu g                                             81

<210> SEQ ID NO 93
<211> LENGTH: 110
<212> TYPE: RNA
<213> ORGANISM: Artificial sequence
<220> FEATURE:
<223> OTHER INFORMATION: Precursor sequence

<400> SEQUENCE: 93
gagcugcuug ccuccccccg uuuuuggcaa ugguagaacu cacacuggug agguaacagg    60
auccgguggu ucuagacuug ccaacuaugg ggcgaggacu cagccggcac              110

<210> SEQ ID NO 94
<211> LENGTH: 88
<212> TYPE: RNA
<213> ORGANISM: Artificial sequence
<220> FEATURE:
<223> OTHER INFORMATION: Precursor sequence

<400> SEQUENCE: 94
cgaggauggg agcugagggc ugggucuuug cgggcgagau gagggugucg gaucaacugg    60
ccuacaaagu cccaguucuc ggcccccg                                      88

<210> SEQ ID NO 95
<211> LENGTH: 96
<212> TYPE: RNA
<213> ORGANISM: Artificial sequence
<220> FEATURE:
<223> OTHER INFORMATION: Precursor sequence

<400> SEQUENCE: 95
ucuauuuguc uuaggugagc uaaaugugug cugggacaca uuugagccaa augucccagc    60
acacauuuag cucacauaag aaaaauggac ucuagu                             96

<210> SEQ ID NO 96
<211> LENGTH: 23
<212> TYPE: RNA
<213> ORGANISM: Artificial sequence
<220> FEATURE:
<223> OTHER INFORMATION: mature sequence

<400> SEQUENCE: 96
uggaagacua gugauuuugu ugu                                           23

<210> SEQ ID NO 97
<211> LENGTH: 22
<212> TYPE: RNA
<213> ORGANISM: Artificial sequence
<220> FEATURE:
<223> OTHER INFORMATION: Mature sequence

<400> SEQUENCE: 97
caacaaauca cagucugcca ua                                            22
```

```
<210> SEQ ID NO 98
<211> LENGTH: 22
<212> TYPE: RNA
<213> ORGANISM: Artificial sequence
<220> FEATURE:
<223> OTHER INFORMATION: Mature sequence

<400> SEQUENCE: 98
caacaaaucc cagucuaccu aa                                              22

<210> SEQ ID NO 99
<211> LENGTH: 23
<212> TYPE: RNA
<213> ORGANISM: Artificial sequence
<220> FEATURE:
<223> OTHER INFORMATION: Mature sequence

<400> SEQUENCE: 99
uacccuguag aaccgaauuu gug                                             23

<210> SEQ ID NO 100
<211> LENGTH: 22
<212> TYPE: RNA
<213> ORGANISM: Artificial sequence
<220> FEATURE:
<223> OTHER INFORMATION: Mature sequence

<400> SEQUENCE: 100
acagauucga uucuagggga au                                              22

<210> SEQ ID NO 101
<211> LENGTH: 23
<212> TYPE: RNA
<213> ORGANISM: Artificial sequence
<220> FEATURE:
<223> OTHER INFORMATION: Mature sequence

<400> SEQUENCE: 101
uaaggugcau cuagugcagu uag                                             23

<210> SEQ ID NO 102
<211> LENGTH: 22
<212> TYPE: RNA
<213> ORGANISM: Artificial sequence
<220> FEATURE:
<223> OTHER INFORMATION: Mature sequence

<400> SEQUENCE: 102
ugcccuaaau gccccuucug gc                                              22

<210> SEQ ID NO 103
<211> LENGTH: 23
<212> TYPE: RNA
<213> ORGANISM: Artificial sequence
<220> FEATURE:
<223> OTHER INFORMATION: Mature sequence

<400> SEQUENCE: 103
uuuggcacua gcacauuuuu gcu                                             23

<210> SEQ ID NO 104
<211> LENGTH: 22
<212> TYPE: RNA
<213> ORGANISM: Artificial sequence
<220> FEATURE:
<223> OTHER INFORMATION: Mature sequence
```

-continued

<400> SEQUENCE: 104
aaucaugugc agugccaaua ug                                              22

<210> SEQ ID NO 105
<211> LENGTH: 21
<212> TYPE: RNA
<213> ORGANISM: Artificial sequence
<220> FEATURE:
<223> OTHER INFORMATION: Mature sequence

<400> SEQUENCE: 105
ucacagugaa ccggucucuu u                                               21

<210> SEQ ID NO 106
<211> LENGTH: 21
<212> TYPE: RNA
<213> ORGANISM: Artificial sequence
<220> FEATURE:
<223> OTHER INFORMATION: Mature sequence

<400> SEQUENCE: 106
cuuuuugcgg ucugggcuug c                                               21

<210> SEQ ID NO 107
<211> LENGTH: 22
<212> TYPE: RNA
<213> ORGANISM: Artificial sequence
<220> FEATURE:
<223> OTHER INFORMATION: Mature sequence

<400> SEQUENCE: 107
aagcccuuac cccaaaaagu au                                              22

<210> SEQ ID NO 108
<211> LENGTH: 22
<212> TYPE: RNA
<213> ORGANISM: Artificial sequence
<220> FEATURE:
<223> OTHER INFORMATION: Mature sequence

<400> SEQUENCE: 108
aagcccuuac cccaaaaagc au                                              22

<210> SEQ ID NO 109
<211> LENGTH: 22
<212> TYPE: RNA
<213> ORGANISM: Artificial sequence
<220> FEATURE:
<223> OTHER INFORMATION: Mature sequence

<400> SEQUENCE: 109
uggacggaga acugauaagg gu                                              22

<210> SEQ ID NO 110
<211> LENGTH: 21
<212> TYPE: RNA
<213> ORGANISM: Artificial sequence
<220> FEATURE:
<223> OTHER INFORMATION: Mature sequence

<400> SEQUENCE: 110
ugauauguuu gauauugggu u                                               21

<210> SEQ ID NO 111
<211> LENGTH: 22

```
<212> TYPE: RNA
<213> ORGANISM: Artificial sequence
<220> FEATURE:
<223> OTHER INFORMATION: Mature sequence

<400> SEQUENCE: 111
gugaaauguu uaggaccacu ag                                              22

<210> SEQ ID NO 112
<211> LENGTH: 22
<212> TYPE: RNA
<213> ORGANISM: Artificial sequence
<220> FEATURE:
<223> OTHER INFORMATION: Mature sequence

<400> SEQUENCE: 112
uucagccagg cuagugcagu cu                                              22

<210> SEQ ID NO 113
<211> LENGTH: 22
<212> TYPE: RNA
<213> ORGANISM: Artificial sequence
<220> FEATURE:
<223> OTHER INFORMATION: Mature sequence

<400> SEQUENCE: 113
uagcagcacg uaaauauugg cg                                              22

<210> SEQ ID NO 114
<211> LENGTH: 22
<212> TYPE: RNA
<213> ORGANISM: Artificial sequence
<220> FEATURE:
<223> OTHER INFORMATION: Mature sequence

<400> SEQUENCE: 114
ccaguauuaa cugugcugcu ga                                              22

<210> SEQ ID NO 115
<211> LENGTH: 22
<212> TYPE: RNA
<213> ORGANISM: Artificial sequence
<220> FEATURE:
<223> OTHER INFORMATION: Mature sequence

<400> SEQUENCE: 115
ccaauauuac ugugcugcuu ua                                              22

<210> SEQ ID NO 116
<211> LENGTH: 22
<212> TYPE: RNA
<213> ORGANISM: Artificial sequence
<220> FEATURE:
<223> OTHER INFORMATION: Mature sequence

<400> SEQUENCE: 116
uuuggucccc uucaaccagc ug                                              22

<210> SEQ ID NO 117
<211> LENGTH: 22
<212> TYPE: RNA
<213> ORGANISM: Artificial sequence
<220> FEATURE:
<223> OTHER INFORMATION: Mature sequence

<400> SEQUENCE: 117
``` ugauuggu ac gucuguggu ag                                                   22

<210> SEQ ID NO 118
<211> LENGTH: 21
<212> TYPE: RNA
<213> ORGANISM: Artificial sequence
<220> FEATURE:
<223> OTHER INFORMATION: Mature sequence

<400> SEQUENCE: 118
uacugcagac aguggcaauc a                                                    21

<210> SEQ ID NO 119
<211> LENGTH: 22
<212> TYPE: RNA
<213> ORGANISM: Artificial sequence
<220> FEATURE:
<223> OTHER INFORMATION: Mature sequence

<400> SEQUENCE: 119
uacugcagac guggcaauca ug                                                   22

<210> SEQ ID NO 120
<211> LENGTH: 21
<212> TYPE: RNA
<213> ORGANISM: Artificial sequence
<220> FEATURE:
<223> OTHER INFORMATION: Mature sequence

<400> SEQUENCE: 120
cagcagcaca cugugguuug u                                                    21

<210> SEQ ID NO 121
<211> LENGTH: 22
<212> TYPE: RNA
<213> ORGANISM: Artificial sequence
<220> FEATURE:
<223> OTHER INFORMATION: Mature sequence

<400> SEQUENCE: 121
caaaccacac ugugguguua ga                                                   22

<210> SEQ ID NO 122
<211> LENGTH: 23
<212> TYPE: RNA
<213> ORGANISM: Artificial sequence
<220> FEATURE:
<223> OTHER INFORMATION: Mature sequence

<400> SEQUENCE: 122
uaauacugcc ggguaaugau gga                                                  23

<210> SEQ ID NO 123
<211> LENGTH: 22
<212> TYPE: RNA
<213> ORGANISM: Artificial sequence
<220> FEATURE:
<223> OTHER INFORMATION: Mature sequence

<400> SEQUENCE: 123
cgucuuaccc agcaguguuu gg                                                   22

<210> SEQ ID NO 124
<211> LENGTH: 22
<212> TYPE: RNA
<213> ORGANISM: Artificial sequence

```
<220> FEATURE:
<223> OTHER INFORMATION: Mature sequence

<400> SEQUENCE: 124
uucaacgggu auuuauugag ca                                                  22

<210> SEQ ID NO 125
<211> LENGTH: 24
<212> TYPE: RNA
<213> ORGANISM: Artificial sequence
<220> FEATURE:
<223> OTHER INFORMATION: Mature sequence

<400> SEQUENCE: 125
uuuggcaaug guagaacuca cacu                                                24

<210> SEQ ID NO 126
<211> LENGTH: 21
<212> TYPE: RNA
<213> ORGANISM: Artificial sequence
<220> FEATURE:
<223> OTHER INFORMATION: Mature sequence

<400> SEQUENCE: 126
ugguucuaga cuugccaacu a                                                   21

<210> SEQ ID NO 127
<211> LENGTH: 22
<212> TYPE: RNA
<213> ORGANISM: Artificial sequence
<220> FEATURE:
<223> OTHER INFORMATION: Mature sequence

<400> SEQUENCE: 127
aacuggccua caaaguccca gu                                                  22

<210> SEQ ID NO 128
<211> LENGTH: 22
<212> TYPE: RNA
<213> ORGANISM: Artificial sequence
<220> FEATURE:
<223> OTHER INFORMATION: Mature sequence

<400> SEQUENCE: 128
ugggucuuug cgggcgagau ga                                                  22

<210> SEQ ID NO 129
<211> LENGTH: 21
<212> TYPE: RNA
<213> ORGANISM: Artificial sequence
<220> FEATURE:
<223> OTHER INFORMATION: Mature sequence

<400> SEQUENCE: 129
ugagcuaaau gugugcuggg a                                                   21

<210> SEQ ID NO 130
<211> LENGTH: 255
<212> TYPE: DNA
<213> ORGANISM: Artificial sequence
<220> FEATURE:
<223> OTHER INFORMATION: sequence cloned in lentiviral vector

<400> SEQUENCE: 130
gccuuaacca agcaaacuuc ucauuucucu ggugaaaacu gcugccaaaa ccacuugua          60
```

```
aaaattgtac agagcctgta gaaaatatag aagattcatt ggatgttggc ctagttctgt    120
gtggaagact agtgattttg ttgttttttag ataactaaat cgacaacaaa tcacagtctg    180
ccatatggca caggccatgc ctctacagga caaatgattg gtgctgtaaa atgcagcatt    240 tcacaccttta ctagc                                                    255

<210> SEQ ID NO 131
<211> LENGTH: 239
<212> TYPE: DNA
<213> ORGANISM: Artificial sequence
<220> FEATURE:
<223> OTHER INFORMATION: Sequence cloned in lentiviral vector

<400> SEQUENCE: 131
tgaaggagca tccagaccgc tgacctggtg gcgaggggag ggggtggtc ctcgaacgcc     60 ttgcagaact ggcctggata cagagtggac cggctggccc catctggaag actagtgatt   120
ttgttgttgt cttactgcgc tcaacaacaa atcccagtct acctaatggt gccagccatc   180
gcagcggggt gcaggaaatg ggggcagccc ccctttttgg ctatccttcc acgtgttct    239

<210> SEQ ID NO 132
<211> LENGTH: 282
<212> TYPE: DNA
<213> ORGANISM: Artificial sequence
<220> FEATURE:
<223> OTHER INFORMATION: Sequence cloned in lentiviral vector

<400> SEQUENCE: 132
tcatagcttg gctcaggtga aaggaggag ctgggcaggg gtctcagaca tggggcagag     60
ggtggtgaag aagattagag tggctgtggt ctagtgctgt gtggaagact agtgattttg   120
ttgttctgat gtactacgac aacaagtcac agccggcctc atagcgcaga ctcccttcga   180
ccttcgcctt caatgggctg gccagtgggg gagaaccggg gaggtcgggg aagaatcgct   240
tccactcgga gtgggggggc tggctcactc caggcgatac ag                     282

<210> SEQ ID NO 133
<211> LENGTH: 220
<212> TYPE: DNA
<213> ORGANISM: Artificial sequence
<220> FEATURE:
<223> OTHER INFORMATION: Sequence cloned in lentiviral vector

<400> SEQUENCE: 133
tggctcagag gaagagattg gggccggcag cgacctaggt acctcactct gggtgggacc     60
cagaggttgt aacgttgtct atatataccc tgtagaaccg aatttgtgtg gtatccgtat   120
agtcacagat tcgattctag gggaatatat ggtcgatgca aaaacttcac gtttcttcgg   180
aatagccaga gaccaaagtg cgacatggag actagaagca                         220

<210> SEQ ID NO 134
<211> LENGTH: 238
<212> TYPE: DNA
<213> ORGANISM: Artificial sequence
<220> FEATURE:
<223> OTHER INFORMATION: Sequence cloned in lentiviral vector

<400> SEQUENCE: 134
ccatggtgat ttagtcaatg gctactgaga actgtagttt gtgcataatt aagtagttga     60
tgcttttgag ctgcttctta taatgtgtct cttgtgttaa ggtgcatcta gtgcagttag   120
tgaagcagct tagaatctac tgccctaaat gccccttctg gcacaggctg cctaatatac   180
```
agcattttaa aagtatgcct tgagtagtaa tttgaatagg acacatttca gtggtttg          238

<210> SEQ ID NO 135
<211> LENGTH: 222
<212> TYPE: DNA
<213> ORGANISM: Artificial sequence
<220> FEATURE:
<223> OTHER INFORMATION: Sequence cloned in lentiviral vector

<400> SEQUENCE: 135
ctcctagacg tcggaaacag gctgcttcca agggtgcagg gatgcaaggc ccctcgtcca           60
gtgtgtcccc agagagcccg caccagtgcc atctgcttgg ccgattttgg cactagcaca          120
tttttgcttg tgtctctccg ctctgagcaa tcatgtgcag tgccaatatg ggaaaagcag          180
gacccgcagc tgcgtccgcc tccctgcat ccttgtgtca gg                             222

<210> SEQ ID NO 136
<211> LENGTH: 273
<212> TYPE: DNA
<213> ORGANISM: Artificial sequence
<220> FEATURE:
<223> OTHER INFORMATION: Sequence cloned in lentiviral vector

<400> SEQUENCE: 136
ttgacaagtt tgtagcttca ccatatacat ttaatatttt gcaataattg gccttgttcc          60
tgagctgttg gattcggggc cgtagcactg tctgagaggt ttacatttct cacagtgaac         120
cggtctcttt ttcagctgct tcctggcttc tttttactca ggtttccact gcttttttgc         180
tttttttaat gctgtatgaa ggtgttaaca tttgtttata tttttcatta attgtaatac         240
ctttaaatca tgcatcatac tcagaaatag gga                                      273

<210> SEQ ID NO 137
<211> LENGTH: 182
<212> TYPE: DNA
<213> ORGANISM: Artificial sequence
<220> FEATURE:
<223> OTHER INFORMATION: Sequence cloned in lentiviral vector

<400> SEQUENCE: 137
tgactccatg gttcactttc atgatggcca catgcctcct gcccagagcc cggcagccac           60
tgtgcagtgg aaggggggc cgatacactg tacgagagtg agtagcaggt ctcacagtga          120
accggtctct ttccctactg tgtcacactc ctaatggaat gccgttatcc aaagagcagc         180
ac                                                                        182

<210> SEQ ID NO 138
<211> LENGTH: 211
<212> TYPE: DNA
<213> ORGANISM: Artificial sequence
<220> FEATURE:
<223> OTHER INFORMATION: Sequence cloned in lentiviral vector

<400> SEQUENCE: 138
gtaccagcta agccctggag gggccacagc ctcccctcca gcccccctgc catgggatgg           60
ctgctgtctc ctttggatct ttttgcggtc tgggcttgct gttcctctca acagtagtca         120
ggaagccctt acccaaaaa gtatctgcgg gaggccttgt ccacagggga ggctgcccca          180
agggctccag gtgagtcaca gcaaacccaa g                                        211

<210> SEQ ID NO 139

```
<211> LENGTH: 219
<212> TYPE: DNA
<213> ORGANISM: Artificial sequence
<220> FEATURE:
<223> OTHER INFORMATION: Sequence cloned in lentiviral vector

<400> SEQUENCE: 139
gagacatcct gggctgaagg cggcggcgaa ccgaagaagc cggcatattc tgcccttcgc      60 gaatctttt  gcggtctggg cttgctgtac ataactcaat agccggaagc ccttacccca    120
aaaagcattt gcggagggcg cactcgtcga aagacggca gccatccagc gatcgccgaa     180
gcccgcacct tcccgaagct gctccatccg agccttacc                           219

<210> SEQ ID NO 140
<211> LENGTH: 173
<212> TYPE: DNA
<213> ORGANISM: Artificial sequence
<220> FEATURE:
<223> OTHER INFORMATION: Sequence cloned in lentiviral vector

<400> SEQUENCE: 140
tacatcttgt cctgcaaagc ttcatcaaaa cttctttgcc ggccagtcac gtccccttat     60
cacttttcca gccagctttt gtgactgtaa gtgttggacg gagaactgat aagggtaggt    120
gattgacact cacagcctcc ggaaccccg cgccgcctgc acttgcgtga tgg            173

<210> SEQ ID NO 141
<211> LENGTH: 202
<212> TYPE: DNA
<213> ORGANISM: Artificial sequence
<220> FEATURE:
<223> OTHER INFORMATION: Sequence cloned in lentiviral vector

<400> SEQUENCE: 141
tctttgcaac tggaaggaag gcagatgacc cccaaagctc tcctgcctgc ttctgtgtga     60
tatgtttgat attgggttgt ttaattagga accaactaaa tgtcaaacat attcttacag    120
cagcaggtga ttcagcacca ccctctttca tacttcaatc tctggggctc ctgtctcttt    180
tactgaacct cttctctcca gg                                             202

<210> SEQ ID NO 142
<211> LENGTH: 262
<212> TYPE: DNA
<213> ORGANISM: Artificial sequence
<220> FEATURE:
<223> OTHER INFORMATION: Sequence cloned in lentiviral vector

<400> SEQUENCE: 142
gaccagcggg gatctgggcg caggggccgg tccccgggat ccgcaggcga cgcgggcggt     60
cccaagggcg tcgggggctc ctctctccgc agctcggcga accgacggtg ttggggactc    120
gcgcgctggg tccagtggtt cttaacagtt caacagttct gtagcgcaat tgtgaaatgt    180
ttaggaccac tagacccggc gggcgcggcg acagcgacgg agcgtcccac gcgcggcctg    240
gagtcagagt cacagtcagg gg                                             262

<210> SEQ ID NO 143
<211> LENGTH: 240
<212> TYPE: DNA
<213> ORGANISM: Artificial sequence
<220> FEATURE:
<223> OTHER INFORMATION: Sequence cloned in lentiviral vector

<400> SEQUENCE: 143
```

```
acaacttctc aatgagtctg ccctcactgt ccaacaattg agctgagaat ataagaaggg     60
aagggcttca gccaggctag tgcagtctgc tttgtgccaa cactggggtg atgactgccc    120
tagtctagct gaagcttttc ccttctttct acacccagct caagtcccag gtccataaaa    180
cctttagaaa ctcttcagaa actctttaga gcttcagaag ctcttgagaa ttggaagatg    240
```

<210> SEQ ID NO 144
<211> LENGTH: 261
<212> TYPE: DNA
<213> ORGANISM: Artificial sequence
<220> FEATURE:
<223> OTHER INFORMATION: Sequence cloned in lentiviral vector

<400> SEQUENCE: 144

```
ttgtggattt tgaaaaggtg caggccatat tgtgctgcct caaaaataca aggatctgat     60
cttctgaaga aaatatattt cttttattc atagctctta tgatagcaat gtcagcagtg    120
ccttagcagc acgtaaatat tggcgttaag attctaaaat tatctccagt attaactgtg    180
ctgctgaagt aaggttgacc atactctaca gttgtgtttt aatgtatatt aatgttacta    240
atgtgttttc agttttattg a                                              261
```

<210> SEQ ID NO 145
<211> LENGTH: 175
<212> TYPE: DNA
<213> ORGANISM: Artificial sequence
<220> FEATURE:
<223> OTHER INFORMATION: Sequence cloned in lentiviral vector

<400> SEQUENCE: 145

```
tttcatcatc agatgttcgt tttatgtttg gatgaactga catacttgtt ccactctagc     60
agcacgtaaa tattggcgta gtgaaatata tattaaacac caatattact gtgctgcttt    120
agtgtgacag ggatacagca actattttat caattgtttg tatttccctt taagg         175
```

<210> SEQ ID NO 146
<211> LENGTH: 227
<212> TYPE: DNA
<213> ORGANISM: Artificial sequence
<220> FEATURE:
<223> OTHER INFORMATION: Sequence cloned in lentiviral vector

<400> SEQUENCE: 146

```
cttgtagaag gtccatgact gtaatttac caatgaaaag catttaactg ttttggattc      60
caaactagca gcactacaat gctttgctag agctggtaaa atggaaccaa atcgcctctt    120
caatggattt ggtccccttc aaccagctgt agctatgcat tgattactac gggacaacca    180
acgttttcat ttgtgaatat caattacttg ccaactaatt tcaactt                  227
```

<210> SEQ ID NO 147
<211> LENGTH: 251
<212> TYPE: DNA
<213> ORGANISM: Artificial sequence
<220> FEATURE:
<223> OTHER INFORMATION: Sequence cloned in lentiviral vector

<400> SEQUENCE: 147

```
gggactgctt ggtggagccg ccttcttcac cgacgtcgct gttcctcgga tctgggagcc     60
aaatgctttg ctagagctgg taaaatgaa ccaaatcgac tgtccaatgg atttggtccc     120
cttcaaccag ctgtagctgt gcattgatgg cgccgtgcgg cccggccgca ggtcccgcag    180
```

```
ccgtggagag gacccagcag gtggcgcggg gagagcccgg ctcggcacgt ggtcagctcc    240
aagtaagtga a                                                         251

<210> SEQ ID NO 148
<211> LENGTH: 188
<212> TYPE: DNA
<213> ORGANISM: Artificial sequence
<220> FEATURE:
<223> OTHER INFORMATION: Sequence cloned in lentiviral vector

<400> SEQUENCE: 148
tgaatgggtg ggtattaagg caaggctgcc atcctcagac atgctgtgtg tggtacccta    60
ctgcagacag tggcaatcat gtataattaa aaatgattgg tacgtctgtg ggtagagtac    120
tgcatgacac atgcaacata catgatgaca ctgtgtgtgt gttggaggca tttagttgca    180
tgcagagg                                                             188

<210> SEQ ID NO 149
<211> LENGTH: 188
<212> TYPE: DNA
<213> ORGANISM: Artificial sequence
<220> FEATURE:
<223> OTHER INFORMATION: Sequence cloned in lentiviral vector

<400> SEQUENCE: 149
tgaatgggtg ggtattaagg caaggctgcc atcctcagac atgctgtgtg tggtacccta    60
ctgcagacag tggcaatcat gtataattaa aaatgattgg tacgtctgtg ggtagagtac    120
tgcatgacac gtgcaacata catgatgaca ctgtgtgtgt gttggaggca tttagttgca    180
tgcagagg                                                             188

<210> SEQ ID NO 150
<211> LENGTH: 187
<212> TYPE: DNA
<213> ORGANISM: Artificial sequence
<220> FEATURE:
<223> OTHER INFORMATION: Sequence cloned in lentiviral vector

<400> SEQUENCE: 150
tgaatgggtg ggtattaagg caaggctgcc atcctcagac atgctgtgtg tggtacccta    60
ctgcagacgt ggcaatcatg tataattaaa aatgattggt acgtctgtgg gtagagtact    120
gcatgacacg tgcaacatac atgatgacac tgtgtgtgtg ttggaggcat ttagttgcat    180
gcagagg                                                              187

<210> SEQ ID NO 151
<211> LENGTH: 182
<212> TYPE: DNA
<213> ORGANISM: Artificial sequence
<220> FEATURE:
<223> OTHER INFORMATION: Sequence cloned in lentiviral vector

<400> SEQUENCE: 151
tcccagcact gctatgtgct ctcttccttt caacccaccc cggtcctgct cccgcccag     60 cagcacactg tggtttgtac ggcactgtgg ccacgtccaa accacactgt ggtgttagag    120
cgagggtggg ggaggcaccg ccgaggcttg gccctgggag gccatcctgg agaagtgaca    180
ca                                                                   182

<210> SEQ ID NO 152
<211> LENGTH: 140
```

-continued

<212> TYPE: DNA
<213> ORGANISM: Artificial sequence
<220> FEATURE:
<223> OTHER INFORMATION: Sequence cloned in lentiviral vector

<400> SEQUENCE: 152

```
aagctgcctg acccaaggtg ggcgggctgg gcgggggccc tcgtcttacc cagcagtgtt      60
tgggtgcggt tgggagtctc taatactgcc gggtaatgat ggaggcccct gtccctgtgt     120
cagcaacatc catcgcctca                                                  140
```

<210> SEQ ID NO 153
<211> LENGTH: 220
<212> TYPE: DNA
<213> ORGANISM: Artificial sequence
<220> FEATURE:
<223> OTHER INFORMATION: Sequence cloned in lentiviral vector

<400> SEQUENCE: 153

```
aacaaagcat ttgcacacag caaggcacgc cacctgcacc ccgggacgtc catctgtagc      60
gcgcccaagg aaggtaggat tgtgacaccc aacacagtgg gcactcaata aatgtctgtt     120
gaattgaaat gcgttacatt caacgggtat ttattgagca cccactctgt gccagacgct     180
gagcggggcg ccgaggggga cagagaagac aagagcagcc                            220
```

<210> SEQ ID NO 154
<211> LENGTH: 209
<212> TYPE: DNA
<213> ORGANISM: Artificial sequence
<220> FEATURE:
<223> OTHER INFORMATION: Sequence cloned in lentiviral vector

<400> SEQUENCE: 154

```
ctgtctcttc ctcagcacag accgaggcct ccccagctcc tgggggagc tgcttgcctc       60 cccccgtttt tggcaatggt agaactcaca ctggtgaggt aacaggatcc ggtggttcta     120
gacttgccaa ctatggggcg aggactcagc cggcaccctg tgcacagcca gcgagggaag    180
ggccggccat gctggacctg ctgttctcc                                        209
```

<210> SEQ ID NO 155
<211> LENGTH: 294
<212> TYPE: DNA
<213> ORGANISM: Artificial sequence
<220> FEATURE:
<223> OTHER INFORMATION: Sequence cloned in lentiviral vector

<400> SEQUENCE: 155

```
agggacaccc agagcttcgg cggagcggag cgcggtgcac agagccggcg accggaccca      60
gccccgggaa gcccgtcggg gacgcacccc gaactccgag gatggagct gagggctggg     120 tctttgcggg cgagatgagg gtgtcggatc aactggccta caaagtccca gttctcggcc    180
cccgggacca gcgtcttctc cccggtcctc gccccaggcc ggcttcctcc cgggctggcg    240
tgcgctccgg ccaggctgcc tctcaggtcc acgctggaga aggagtggtg aggt            294
```

<210> SEQ ID NO 156
<211> LENGTH: 241
<212> TYPE: DNA
<213> ORGANISM: Artificial sequence
<220> FEATURE:
<223> OTHER INFORMATION: Sequence cloned in lentiviral vector

<400> SEQUENCE: 156

```
attgtattca gaggggcaac acttaacata aaatctgact tcaacagact attattctct    60
gtgaataagg tcttacatat tagcccttca ctcccaacta tttgtctatt tgtcttaggt   120
gagctaaatg tgtgctggga cacatttgag ccaaatgtcc cagcacacat ttagctcaca   180
taagaaaaat ggactctagt tgggagtgag gggctaataa acaccagatc ccaagaaaat   240
t                                                                  241
```

```
<210> SEQ ID NO 157
<211> LENGTH: 7
<212> TYPE: RNA
<213> ORGANISM: Artificial sequence
<220> FEATURE:
<223> OTHER INFORMATION: Seed sequence

<400> SEQUENCE: 157 ggaagac                                                              7

<210> SEQ ID NO 158
<211> LENGTH: 7
<212> TYPE: RNA
<213> ORGANISM: Artificial sequence
<220> FEATURE:
<223> OTHER INFORMATION: Seed sequence

<400> SEQUENCE: 158 aacaaau                                                              7

<210> SEQ ID NO 159
<211> LENGTH: 7
<212> TYPE: RNA
<213> ORGANISM: Artificial sequence
<220> FEATURE:
<223> OTHER INFORMATION: Seed sequence

<400> SEQUENCE: 159 aacaaau                                                              7

<210> SEQ ID NO 160
<211> LENGTH: 7
<212> TYPE: RNA
<213> ORGANISM: Artificial sequence
<220> FEATURE:
<223> OTHER INFORMATION: Seed sequence

<400> SEQUENCE: 160 acccugu                                                              7

<210> SEQ ID NO 161
<211> LENGTH: 7
<212> TYPE: RNA
<213> ORGANISM: Artificial sequence
<220> FEATURE:
<223> OTHER INFORMATION: Seed sequence

<400> SEQUENCE: 161 cagauuc                                                              7

<210> SEQ ID NO 162
<211> LENGTH: 7
<212> TYPE: RNA
<213> ORGANISM: Artificial sequence
<220> FEATURE:
<223> OTHER INFORMATION: Seed sequence

<400> SEQUENCE: 162
``` aaggugc 7

<210> SEQ ID NO 163
<211> LENGTH: 7
<212> TYPE: RNA
<213> ORGANISM: Artificial sequence
<220> FEATURE:
<223> OTHER INFORMATION: Seed sequence

<400> SEQUENCE: 163 gcccuaa 7

<210> SEQ ID NO 164
<211> LENGTH: 7
<212> TYPE: RNA
<213> ORGANISM: Artificial sequence
<220> FEATURE:
<223> OTHER INFORMATION: Seed sequence

<400> SEQUENCE: 164 uuggcac 7

<210> SEQ ID NO 165
<211> LENGTH: 7
<212> TYPE: RNA
<213> ORGANISM: Artificial sequence
<220> FEATURE:
<223> OTHER INFORMATION: Seed sequence

<400> SEQUENCE: 165 aucaugu 7

<210> SEQ ID NO 166
<211> LENGTH: 7
<212> TYPE: RNA
<213> ORGANISM: Artificial sequence
<220> FEATURE:
<223> OTHER INFORMATION: Seed sequence

<400> SEQUENCE: 166 cacagug 7

<210> SEQ ID NO 167
<211> LENGTH: 7
<212> TYPE: RNA
<213> ORGANISM: Artificial sequence
<220> FEATURE:
<223> OTHER INFORMATION: Seed sequence

<400> SEQUENCE: 167 uuuuugc 7

<210> SEQ ID NO 168
<211> LENGTH: 7
<212> TYPE: RNA
<213> ORGANISM: Artificial sequence
<220> FEATURE:
<223> OTHER INFORMATION: Seed sequence

<400> SEQUENCE: 168 agcccuu 7

<210> SEQ ID NO 169
<211> LENGTH: 7
<212> TYPE: RNA

```
<213> ORGANISM: Artificial sequence
<220> FEATURE:
<223> OTHER INFORMATION: Seed sequence

<400> SEQUENCE: 169 agcccuu                                                                    7

<210> SEQ ID NO 170
<211> LENGTH: 7
<212> TYPE: RNA
<213> ORGANISM: Artificial sequence
<220> FEATURE:
<223> OTHER INFORMATION: Seed sequence

<400> SEQUENCE: 170 ggacgga                                                                    7

<210> SEQ ID NO 171
<211> LENGTH: 7
<212> TYPE: RNA
<213> ORGANISM: Artificial sequence
<220> FEATURE:
<223> OTHER INFORMATION: Seed sequence

<400> SEQUENCE: 171 gauaugu                                                                    7

<210> SEQ ID NO 172
<211> LENGTH: 7
<212> TYPE: RNA
<213> ORGANISM: Artificial sequence
<220> FEATURE:
<223> OTHER INFORMATION: Seed sequence

<400> SEQUENCE: 172 ugaaaug                                                                    7

<210> SEQ ID NO 173
<211> LENGTH: 7
<212> TYPE: RNA
<213> ORGANISM: Artificial sequence
<220> FEATURE:
<223> OTHER INFORMATION: Seed sequence

<400> SEQUENCE: 173 ucagcca                                                                    7

<210> SEQ ID NO 174
<211> LENGTH: 7
<212> TYPE: RNA
<213> ORGANISM: Artificial sequence
<220> FEATURE:
<223> OTHER INFORMATION: Seed sequence

<400> SEQUENCE: 174 agcagca                                                                    7

<210> SEQ ID NO 175
<211> LENGTH: 7
<212> TYPE: RNA
<213> ORGANISM: Artificial sequence
<220> FEATURE:
<223> OTHER INFORMATION: Seed sequence

<400> SEQUENCE: 175 caguauu                                                                    7
```

```
<210> SEQ ID NO 176
<211> LENGTH: 7
<212> TYPE: RNA
<213> ORGANISM: Artificial sequence
<220> FEATURE:
<223> OTHER INFORMATION: Seed sequence

<400> SEQUENCE: 176 caauauu                                                                    7

<210> SEQ ID NO 177
<211> LENGTH: 7
<212> TYPE: RNA
<213> ORGANISM: Artificial sequence
<220> FEATURE:
<223> OTHER INFORMATION: Seed sequence

<400> SEQUENCE: 177 uuggucc                                                                    7

<210> SEQ ID NO 178
<211> LENGTH: 7
<212> TYPE: RNA
<213> ORGANISM: Artificial sequence
<220> FEATURE:
<223> OTHER INFORMATION: Seed sequence

<400> SEQUENCE: 178 gauuggu                                                                    7

<210> SEQ ID NO 179
<211> LENGTH: 7
<212> TYPE: RNA
<213> ORGANISM: Artificial sequence
<220> FEATURE:
<223> OTHER INFORMATION: Seed sequence

<400> SEQUENCE: 179 acugcag                                                                    7

<210> SEQ ID NO 180
<211> LENGTH: 7
<212> TYPE: RNA
<213> ORGANISM: Artificial sequence
<220> FEATURE:
<223> OTHER INFORMATION: Seed sequence

<400> SEQUENCE: 180 acugcag                                                                    7

<210> SEQ ID NO 181
<211> LENGTH: 7
<212> TYPE: RNA
<213> ORGANISM: Artificial sequence
<220> FEATURE:
<223> OTHER INFORMATION: Seed sequence

<400> SEQUENCE: 181 agcagca                                                                    7

<210> SEQ ID NO 182
<211> LENGTH: 7
<212> TYPE: RNA
<213> ORGANISM: Artificial sequence
<220> FEATURE:
```

<223> OTHER INFORMATION: Seed sequence

<400> SEQUENCE: 182 aaaccac                                                                 7

<210> SEQ ID NO 183
<211> LENGTH: 7
<212> TYPE: RNA
<213> ORGANISM: Artificial sequence
<220> FEATURE:
<223> OTHER INFORMATION: Seed sequence

<400> SEQUENCE: 183 aauacug                                                                 7

<210> SEQ ID NO 184
<211> LENGTH: 7
<212> TYPE: RNA
<213> ORGANISM: Artificial sequence
<220> FEATURE:
<223> OTHER INFORMATION: Seed sequence

<400> SEQUENCE: 184 gucuuac                                                                 7

<210> SEQ ID NO 185
<211> LENGTH: 7
<212> TYPE: RNA
<213> ORGANISM: Artificial sequence
<220> FEATURE:
<223> OTHER INFORMATION: Seed sequence

<400> SEQUENCE: 185 ucaacgg                                                                 7

<210> SEQ ID NO 186
<211> LENGTH: 7
<212> TYPE: RNA
<213> ORGANISM: Artificial sequence
<220> FEATURE:
<223> OTHER INFORMATION: Seed sequence

<400> SEQUENCE: 186 uuggcaa                                                                 7

<210> SEQ ID NO 187
<211> LENGTH: 7
<212> TYPE: RNA
<213> ORGANISM: Artificial sequence
<220> FEATURE:
<223> OTHER INFORMATION: Seed sequence

<400> SEQUENCE: 187 gguucua                                                                 7

<210> SEQ ID NO 188
<211> LENGTH: 7
<212> TYPE: RNA
<213> ORGANISM: Artificial sequence
<220> FEATURE:
<223> OTHER INFORMATION: Seed sequence

<400> SEQUENCE: 188 acuggcc                                                                 7

```
<210> SEQ ID NO 189
<211> LENGTH: 7
<212> TYPE: RNA
<213> ORGANISM: Artificial sequence
<220> FEATURE:
<223> OTHER INFORMATION: Seed sequence

<400> SEQUENCE: 189 gggucuu                                                                    7

<210> SEQ ID NO 190
<211> LENGTH: 7
<212> TYPE: RNA
<213> ORGANISM: Artificial sequence
<220> FEATURE:
<223> OTHER INFORMATION: Seed sequence

<400> SEQUENCE: 190 gagcuaa                                                                    7

<210> SEQ ID NO 191
<211> LENGTH: 24
<212> TYPE: RNA
<213> ORGANISM: Artificial sequence
<220> FEATURE:
<223> OTHER INFORMATION: isomiR sequence

<400> SEQUENCE: 191
uggaagacua gugauuuugu uguu                                                 24

<210> SEQ ID NO 192
<211> LENGTH: 22
<212> TYPE: RNA
<213> ORGANISM: Artificial sequence
<220> FEATURE:
<223> OTHER INFORMATION: isomiR sequence

<400> SEQUENCE: 192
uggaagacua gugauuuugu ug                                                   22

<210> SEQ ID NO 193
<211> LENGTH: 25
<212> TYPE: RNA
<213> ORGANISM: Artificial sequence
<220> FEATURE:
<223> OTHER INFORMATION: isomiR sequence

<400> SEQUENCE: 193
uggaagacua gugauuuugu uguuc                                                25

<210> SEQ ID NO 194
<211> LENGTH: 22
<212> TYPE: RNA
<213> ORGANISM: Artificial sequence
<220> FEATURE:
<223> OTHER INFORMATION: isomiR sequence

<400> SEQUENCE: 194
uacccuguag aaccgaauuu gu                                                   22

<210> SEQ ID NO 195
<211> LENGTH: 22
<212> TYPE: RNA
<213> ORGANISM: Artificial sequence
<220> FEATURE:
<223> OTHER INFORMATION: isomiR sequence
```

```
<400> SEQUENCE: 195
acccuguaga accgaauuug ug                                          22

<210> SEQ ID NO 196
<211> LENGTH: 21
<212> TYPE: RNA
<213> ORGANISM: Artificial sequence
<220> FEATURE:
<223> OTHER INFORMATION: isomiR sequence

<400> SEQUENCE: 196
uacccuguag aaccgaauuu g                                           21

<210> SEQ ID NO 197
<211> LENGTH: 21
<212> TYPE: RNA
<213> ORGANISM: Artificial sequence
<220> FEATURE:
<223> OTHER INFORMATION: isomiR sequence

<400> SEQUENCE: 197
acccuguaga accgaauuug u                                           21

<210> SEQ ID NO 198
<211> LENGTH: 23
<212> TYPE: RNA
<213> ORGANISM: Artificial sequence
<220> FEATURE:
<223> OTHER INFORMATION: isomiR sequence

<400> SEQUENCE: 198
acccuguaga accgaauuug ugu                                         23

<210> SEQ ID NO 199
<211> LENGTH: 21
<212> TYPE: RNA
<213> ORGANISM: Artificial sequence
<220> FEATURE:
<223> OTHER INFORMATION: isomiR sequence

<400> SEQUENCE: 199
agauucgauu cuagggaau a                                            21

<210> SEQ ID NO 200
<211> LENGTH: 21
<212> TYPE: RNA
<213> ORGANISM: Artificial sequence
<220> FEATURE:
<223> OTHER INFORMATION: isomiR sequence

<400> SEQUENCE: 200
acagauucga uucuagggga a                                           21

<210> SEQ ID NO 201
<211> LENGTH: 21
<212> TYPE: RNA
<213> ORGANISM: Artificial sequence
<220> FEATURE:
<223> OTHER INFORMATION: isomiR sequence

<400> SEQUENCE: 201
cagauucgau ucuagggaa u                                            21

<210> SEQ ID NO 202
<211> LENGTH: 22
```

```
<212> TYPE: RNA
<213> ORGANISM: Artificial sequence
<220> FEATURE:
<223> OTHER INFORMATION: isomiR sequence

<400> SEQUENCE: 202
cagauucgau ucuaggggaa ua                                              22

<210> SEQ ID NO 203
<211> LENGTH: 19
<212> TYPE: RNA
<213> ORGANISM: Artificial sequence
<220> FEATURE:
<223> OTHER INFORMATION: isomiR sequence

<400> SEQUENCE: 203
agauucgauu cuaggggaa                                                  19

<210> SEQ ID NO 204
<211> LENGTH: 20
<212> TYPE: RNA
<213> ORGANISM: Artificial sequence
<220> FEATURE:
<223> OTHER INFORMATION: isomiR sequence

<400> SEQUENCE: 204
cagauucgau ucuaggggaa                                                 20

<210> SEQ ID NO 205
<211> LENGTH: 20
<212> TYPE: RNA
<213> ORGANISM: Artificial sequence
<220> FEATURE:
<223> OTHER INFORMATION: isomiR sequence

<400> SEQUENCE: 205
agauucgauu cuaggggaau                                                 20

<210> SEQ ID NO 206
<211> LENGTH: 22
<212> TYPE: RNA
<213> ORGANISM: Artificial sequence
<220> FEATURE:
<223> OTHER INFORMATION: isomiR sequence

<400> SEQUENCE: 206
agauucgauu cuaggggaau au                                              22

<210> SEQ ID NO 207
<211> LENGTH: 21
<212> TYPE: RNA
<213> ORGANISM: Artificial sequence
<220> FEATURE:
<223> OTHER INFORMATION: isomiR sequence

<400> SEQUENCE: 207
uaaggugcau cuagugcagu u                                               21

<210> SEQ ID NO 208
<211> LENGTH: 22
<212> TYPE: RNA
<213> ORGANISM: Artificial sequence
<220> FEATURE:
<223> OTHER INFORMATION: isomiR sequence

<400> SEQUENCE: 208
```
uaaggugcau cuagugcagu ua                                             22

<210> SEQ ID NO 209
<211> LENGTH: 19
<212> TYPE: RNA
<213> ORGANISM: Artificial sequence
<220> FEATURE:
<223> OTHER INFORMATION: isomiR sequence

<400> SEQUENCE: 209
uaaggugcau cuagugcag                                                 19

<210> SEQ ID NO 210
<211> LENGTH: 20
<212> TYPE: RNA
<213> ORGANISM: Artificial sequence
<220> FEATURE:
<223> OTHER INFORMATION: isomiR sequence

<400> SEQUENCE: 210
uaaggugcau cuagugcagu                                                20

<210> SEQ ID NO 211
<211> LENGTH: 19
<212> TYPE: RNA
<213> ORGANISM: Artificial sequence
<220> FEATURE:
<223> OTHER INFORMATION: isomiR sequence

<400> SEQUENCE: 211
aaggugcauc uagugcagu                                                 19

<210> SEQ ID NO 212
<211> LENGTH: 22
<212> TYPE: RNA
<213> ORGANISM: Artificial sequence
<220> FEATURE:
<223> OTHER INFORMATION: isomiR sequence

<400> SEQUENCE: 212
uacugcccua aaugccccuu cu                                             22

<210> SEQ ID NO 213
<211> LENGTH: 23
<212> TYPE: RNA
<213> ORGANISM: Artificial sequence
<220> FEATURE:
<223> OTHER INFORMATION: IsomiR sequence

<400> SEQUENCE: 213
uacugcccua aaugccccuu cug                                            23

<210> SEQ ID NO 214
<211> LENGTH: 20
<212> TYPE: RNA
<213> ORGANISM: Artificial sequence
<220> FEATURE:
<223> OTHER INFORMATION: IsomiR sequence

<400> SEQUENCE: 214
uacugcccua aaugccccuu                                                20

<210> SEQ ID NO 215
<211> LENGTH: 21
<212> TYPE: RNA
<213> ORGANISM: Artificial sequence

```
<220> FEATURE:
<223> OTHER INFORMATION: IsomiR sequence

<400> SEQUENCE: 215
acugcccuaa augcccuuc u                                              21

<210> SEQ ID NO 216
<211> LENGTH: 22
<212> TYPE: RNA
<213> ORGANISM: Artificial sequence
<220> FEATURE:
<223> OTHER INFORMATION: IsomiR sequence

<400> SEQUENCE: 216
acugcccuaa augcccuuc ug                                             22

<210> SEQ ID NO 217
<211> LENGTH: 21
<212> TYPE: RNA
<213> ORGANISM: Artificial sequence
<220> FEATURE:
<223> OTHER INFORMATION: IsomiR sequence

<400> SEQUENCE: 217
uacugcccua aaugcccuu c                                              21

<210> SEQ ID NO 218
<211> LENGTH: 25
<212> TYPE: RNA
<213> ORGANISM: Artificial sequence
<220> FEATURE:
<223> OTHER INFORMATION: IsomiR sequence

<400> SEQUENCE: 218
uacugcccua aaugcccuu cuggc                                          25

<210> SEQ ID NO 219
<211> LENGTH: 19
<212> TYPE: RNA
<213> ORGANISM: Artificial sequence
<220> FEATURE:
<223> OTHER INFORMATION: IsomiR sequence

<400> SEQUENCE: 219
uacugcccua aaugcccu                                                 19

<210> SEQ ID NO 220
<211> LENGTH: 24
<212> TYPE: RNA
<213> ORGANISM: Artificial sequence
<220> FEATURE:
<223> OTHER INFORMATION: IsomiR sequence

<400> SEQUENCE: 220
acugcccuaa augcccuuc uggc                                           24

<210> SEQ ID NO 221
<211> LENGTH: 23
<212> TYPE: RNA
<213> ORGANISM: Artificial sequence
<220> FEATURE:
<223> OTHER INFORMATION: isomiR sequence

<400> SEQUENCE: 221
acugcccuaa augcccuuc ugg                                            23
```

```
<210> SEQ ID NO 222
<211> LENGTH: 21
<212> TYPE: RNA
<213> ORGANISM: Artificial sequence
<220> FEATURE:
<223> OTHER INFORMATION: IsomiR sequence

<400> SEQUENCE: 222
uuuggcacua gcacauuuuu g                                              21

<210> SEQ ID NO 223
<211> LENGTH: 22
<212> TYPE: RNA
<213> ORGANISM: Artificial sequence
<220> FEATURE:
<223> OTHER INFORMATION: IsomiR sequence

<400> SEQUENCE: 223
uuuggcacua gcacauuuuu gc                                             22

<210> SEQ ID NO 224
<211> LENGTH: 20
<212> TYPE: RNA
<213> ORGANISM: Artificial sequence
<220> FEATURE:
<223> OTHER INFORMATION: IsomiR sequence

<400> SEQUENCE: 224
uuuggcacua gcacauuuuu                                                20

<210> SEQ ID NO 225
<211> LENGTH: 22
<212> TYPE: RNA
<213> ORGANISM: Artificial sequence
<220> FEATURE:
<223> OTHER INFORMATION: IsomiR sequence

<400> SEQUENCE: 225
ucacagugaa ccggucucuu uu                                             22

<210> SEQ ID NO 226
<211> LENGTH: 20
<212> TYPE: RNA
<213> ORGANISM: Artificial sequence
<220> FEATURE:
<223> OTHER INFORMATION: IsomiR sequence

<400> SEQUENCE: 226
ucacagugaa ccggucucuu                                                20

<210> SEQ ID NO 227
<211> LENGTH: 19
<212> TYPE: RNA
<213> ORGANISM: Artificial sequence
<220> FEATURE:
<223> OTHER INFORMATION: IsomiR sequence

<400> SEQUENCE: 227
ucacagugaa ccggucucu                                                 19

<210> SEQ ID NO 228
<211> LENGTH: 22
<212> TYPE: RNA
<213> ORGANISM: Artificial sequence
<220> FEATURE:
<223> OTHER INFORMATION: IsomiR sequence
```

```
<400> SEQUENCE: 228
ucacagugaa ccggucucuu uc                                              22

<210> SEQ ID NO 229
<211> LENGTH: 23
<212> TYPE: RNA
<213> ORGANISM: Artificial sequence
<220> FEATURE:
<223> OTHER INFORMATION: IsomiR sequence

<400> SEQUENCE: 229
ucacagugaa ccggucucuu ucc                                             23

<210> SEQ ID NO 230
<211> LENGTH: 20
<212> TYPE: RNA
<213> ORGANISM: Artificial sequence
<220> FEATURE:
<223> OTHER INFORMATION: IsomiR sequence

<400> SEQUENCE: 230
cuuuuugcgg ucugggcuug                                                 20

<210> SEQ ID NO 231
<211> LENGTH: 19
<212> TYPE: RNA
<213> ORGANISM: Artificial sequence
<220> FEATURE:
<223> OTHER INFORMATION: IsomiR sequence

<400> SEQUENCE: 231
cuuuuugcgg ucugggcuu                                                  19

<210> SEQ ID NO 232
<211> LENGTH: 18
<212> TYPE: RNA
<213> ORGANISM: Artificial sequence
<220> FEATURE:
<223> OTHER INFORMATION: IsomiR sequence

<400> SEQUENCE: 232
cuuuuugcgg ucugggcu                                                   18

<210> SEQ ID NO 233
<211> LENGTH: 22
<212> TYPE: RNA
<213> ORGANISM: Artificial sequence
<220> FEATURE:
<223> OTHER INFORMATION: IsomiR sequence

<400> SEQUENCE: 233
cuuuuugcgg ucugggcuug cu                                              22

<210> SEQ ID NO 234
<211> LENGTH: 23
<212> TYPE: RNA
<213> ORGANISM: Artificial sequence
<220> FEATURE:
<223> OTHER INFORMATION: IsomiR sequence

<400> SEQUENCE: 234
uggacggaga acugauaagg gua                                             23

<210> SEQ ID NO 235
```

```
<211> LENGTH: 21
<212> TYPE: RNA
<213> ORGANISM: Artificial sequence
<220> FEATURE:
<223> OTHER INFORMATION: IsomiR sequence

<400> SEQUENCE: 235
uggacggaga acugauaagg g                                            21

<210> SEQ ID NO 236
<211> LENGTH: 20
<212> TYPE: RNA
<213> ORGANISM: Artificial sequence
<220> FEATURE:
<223> OTHER INFORMATION: IsomiR sequence

<400> SEQUENCE: 236
uggacggaga acugauaagg                                              20

<210> SEQ ID NO 237
<211> LENGTH: 22
<212> TYPE: RNA
<213> ORGANISM: Artificial sequence
<220> FEATURE:
<223> OTHER INFORMATION: IsomiR sequence

<400> SEQUENCE: 237
ugauauguuu gauauugggu ug                                           22

<210> SEQ ID NO 238
<211> LENGTH: 23
<212> TYPE: RNA
<213> ORGANISM: Artificial sequence
<220> FEATURE:
<223> OTHER INFORMATION: IsomiR sequence

<400> SEQUENCE: 238
ugauauguuu gauauugggu ugu                                          23

<210> SEQ ID NO 239
<211> LENGTH: 21
<212> TYPE: RNA
<213> ORGANISM: Artificial sequence
<220> FEATURE:
<223> OTHER INFORMATION: IsomiR sequence

<400> SEQUENCE: 239
ugaaauguuu aggaccacua g                                            21

<210> SEQ ID NO 240
<211> LENGTH: 21
<212> TYPE: RNA
<213> ORGANISM: Artificial sequence
<220> FEATURE:
<223> OTHER INFORMATION: IsomiR sequence

<400> SEQUENCE: 240
gugaaauguu uaggaccacu a                                            21

<210> SEQ ID NO 241
<211> LENGTH: 20
<212> TYPE: RNA
<213> ORGANISM: Artificial sequence
<220> FEATURE:
<223> OTHER INFORMATION: IsomiR sequence

<400> SEQUENCE: 241
```

```
gugaaauguu uaggaccacu                                          20

<210> SEQ ID NO 242
<211> LENGTH: 23
<212> TYPE: RNA
<213> ORGANISM: Artificial sequence
<220> FEATURE:
<223> OTHER INFORMATION: IsomiR sequence

<400> SEQUENCE: 242
gugaaauguu uaggaccacu aga                                      23

<210> SEQ ID NO 243
<211> LENGTH: 21
<212> TYPE: RNA
<213> ORGANISM: Artificial sequence
<220> FEATURE:
<223> OTHER INFORMATION: IsomiR sequence

<400> SEQUENCE: 243
uucagccagg cuagugcagu c                                        21

<210> SEQ ID NO 244
<211> LENGTH: 22
<212> TYPE: RNA
<213> ORGANISM: Artificial sequence
<220> FEATURE:
<223> OTHER INFORMATION: IsomiR sequence

<400> SEQUENCE: 244
cuucagccag gcuagugcag uc                                       22

<210> SEQ ID NO 245
<211> LENGTH: 21
<212> TYPE: RNA
<213> ORGANISM: Artificial sequence
<220> FEATURE:
<223> OTHER INFORMATION: IsomiR sequence

<400> SEQUENCE: 245
ucagccaggc uagugcaguc u                                        21

<210> SEQ ID NO 246
<211> LENGTH: 20
<212> TYPE: RNA
<213> ORGANISM: Artificial sequence
<220> FEATURE:
<223> OTHER INFORMATION: IsomiR sequence

<400> SEQUENCE: 246
uucagccagg cuagugcagu                                          20

<210> SEQ ID NO 247
<211> LENGTH: 24
<212> TYPE: RNA
<213> ORGANISM: Artificial sequence
<220> FEATURE:
<223> OTHER INFORMATION: IsomiR sequence

<400> SEQUENCE: 247
cuucagccag gcuagugcag ucug                                     24

<210> SEQ ID NO 248
<211> LENGTH: 21
<212> TYPE: RNA
```

<213> ORGANISM: Artificial sequence
<220> FEATURE:
<223> OTHER INFORMATION: IsomiR sequence

<400> SEQUENCE: 248
uagcagcacg uaaauauugg c                                              21

<210> SEQ ID NO 249
<211> LENGTH: 19
<212> TYPE: RNA
<213> ORGANISM: Artificial sequence
<220> FEATURE:
<223> OTHER INFORMATION: IsomiR sequence

<400> SEQUENCE: 249
uagcagcacg uaaauauug                                                 19

<210> SEQ ID NO 250
<211> LENGTH: 23
<212> TYPE: RNA
<213> ORGANISM: Artificial sequence
<220> FEATURE:
<223> OTHER INFORMATION: IsomiR sequence

<400> SEQUENCE: 250
uagcagcacg uaaauauugg cgu                                            23

<210> SEQ ID NO 251
<211> LENGTH: 20
<212> TYPE: RNA
<213> ORGANISM: Artificial sequence
<220> FEATURE:
<223> OTHER INFORMATION: IsomiR sequence

<400> SEQUENCE: 251
uagcagcacg uaaauauugg                                                20

<210> SEQ ID NO 252
<211> LENGTH: 22
<212> TYPE: RNA
<213> ORGANISM: Artificial sequence
<220> FEATURE:
<223> OTHER INFORMATION: IsomiR sequence

<400> SEQUENCE: 252
uuggucsccu ucaaccagcu gu                                             22

<210> SEQ ID NO 253
<211> LENGTH: 21
<212> TYPE: RNA
<213> ORGANISM: Artificial sequence
<220> FEATURE:
<223> OTHER INFORMATION: IsomiR sequence

<400> SEQUENCE: 253
uuuggucccc uucaaccagc u                                              21

<210> SEQ ID NO 254
<211> LENGTH: 23
<212> TYPE: RNA
<213> ORGANISM: Artificial sequence
<220> FEATURE:
<223> OTHER INFORMATION: IsomiR sequence

<400> SEQUENCE: 254
uuuggucccc uucaaccagc ugu                                            23

<210> SEQ ID NO 255
<211> LENGTH: 21
<212> TYPE: RNA
<213> ORGANISM: Artificial sequence
<220> FEATURE:
<223> OTHER INFORMATION: IsomiR sequence

<400> SEQUENCE: 255
uugguccccu ucaaccagcu g                                             21

<210> SEQ ID NO 256
<211> LENGTH: 20
<212> TYPE: RNA
<213> ORGANISM: Artificial sequence
<220> FEATURE:
<223> OTHER INFORMATION: IsomiR sequence

<400> SEQUENCE: 256
uugguccccu ucaaccagcu                                               20

<210> SEQ ID NO 257
<211> LENGTH: 23
<212> TYPE: RNA
<213> ORGANISM: Artificial sequence
<220> FEATURE:
<223> OTHER INFORMATION: IsomiR sequence

<400> SEQUENCE: 257
ugauugguac gucugugggu aga                                           23

<210> SEQ ID NO 258
<211> LENGTH: 21
<212> TYPE: RNA
<213> ORGANISM: Artificial sequence
<220> FEATURE:
<223> OTHER INFORMATION: IsomiR sequence

<400> SEQUENCE: 258
ugauugguac gucugugggu a                                             21

<210> SEQ ID NO 259
<211> LENGTH: 21
<212> TYPE: RNA
<213> ORGANISM: Artificial sequence
<220> FEATURE:
<223> OTHER INFORMATION: IsomiR sequence

<400> SEQUENCE: 259
auugguacgu cuguggguag a                                             21

<210> SEQ ID NO 260
<211> LENGTH: 23
<212> TYPE: RNA
<213> ORGANISM: Artificial sequence
<220> FEATURE:
<223> OTHER INFORMATION: IsomiR sequence

<400> SEQUENCE: 260
uacugcagac aguggcaauc aug                                           23

<210> SEQ ID NO 261
<211> LENGTH: 22
<212> TYPE: RNA
<213> ORGANISM: Artificial sequence
<220> FEATURE:

```
<223> OTHER INFORMATION: IsomiR sequence

<400> SEQUENCE: 261
uacugcagac aguggcaauc au                                              22

<210> SEQ ID NO 262
<211> LENGTH: 20
<212> TYPE: RNA
<213> ORGANISM: Artificial sequence
<220> FEATURE:
<223> OTHER INFORMATION: IsomiR sequence

<400> SEQUENCE: 262
uacugcagac aguggcaauc                                                 20

<210> SEQ ID NO 263
<211> LENGTH: 24
<212> TYPE: RNA
<213> ORGANISM: Artificial sequence
<220> FEATURE:
<223> OTHER INFORMATION: IsomiR sequence

<400> SEQUENCE: 263
uacugcagac aguggcaauc augu                                            24

<210> SEQ ID NO 264
<211> LENGTH: 21
<212> TYPE: RNA
<213> ORGANISM: Artificial sequence
<220> FEATURE:
<223> OTHER INFORMATION: IsomiR sequence

<400> SEQUENCE: 264
uacugcagac guggcaauca u                                               21

<210> SEQ ID NO 265
<211> LENGTH: 20
<212> TYPE: RNA
<213> ORGANISM: Artificial sequence
<220> FEATURE:
<223> OTHER INFORMATION: IsomiR sequence

<400> SEQUENCE: 265
uacugcagac guggcaauca                                                 20

<210> SEQ ID NO 266
<211> LENGTH: 22
<212> TYPE: RNA
<213> ORGANISM: Artificial sequence
<220> FEATURE:
<223> OTHER INFORMATION: IsomiR sequence

<400> SEQUENCE: 266
cagcagcaca cugugguuug ua                                              22

<210> SEQ ID NO 267
<211> LENGTH: 20
<212> TYPE: RNA
<213> ORGANISM: Artificial sequence
<220> FEATURE:
<223> OTHER INFORMATION: IsomiR sequence

<400> SEQUENCE: 267
agcagcacac uguguuugu                                                  20
```

-continued

```
<210> SEQ ID NO 268
<211> LENGTH: 21
<212> TYPE: RNA
<213> ORGANISM: Artificial sequence
<220> FEATURE:
<223> OTHER INFORMATION: IsomiR sequence

<400> SEQUENCE: 268
agcagcacac ugugguuugu a                                             21

<210> SEQ ID NO 269
<211> LENGTH: 22
<212> TYPE: RNA
<213> ORGANISM: Artificial sequence
<220> FEATURE:
<223> OTHER INFORMATION: IsomiR sequence

<400> SEQUENCE: 269
agcagcacac ugugguuugu ac                                            22

<210> SEQ ID NO 270
<211> LENGTH: 20
<212> TYPE: RNA
<213> ORGANISM: Artificial sequence
<220> FEATURE:
<223> OTHER INFORMATION: IsomiR sequence

<400> SEQUENCE: 270
cagcagcaca cugugguuug                                               20

<210> SEQ ID NO 271
<211> LENGTH: 21
<212> TYPE: RNA
<213> ORGANISM: Artificial sequence
<220> FEATURE:
<223> OTHER INFORMATION: IsomiR sequence

<400> SEQUENCE: 271
cgucuuaccc agcaguguuu g                                             21

<210> SEQ ID NO 272
<211> LENGTH: 20
<212> TYPE: RNA
<213> ORGANISM: Artificial sequence
<220> FEATURE:
<223> OTHER INFORMATION: IsomiR sequence

<400> SEQUENCE: 272
cgucuuaccc agcaguguuu                                               20

<210> SEQ ID NO 273
<211> LENGTH: 21
<212> TYPE: RNA
<213> ORGANISM: Artificial sequence
<220> FEATURE:
<223> OTHER INFORMATION: IsomiR sequence

<400> SEQUENCE: 273
gucuuaccca gcaguguuug g                                             21

<210> SEQ ID NO 274
<211> LENGTH: 21
<212> TYPE: RNA
<213> ORGANISM: Artificial sequence
<220> FEATURE:
<223> OTHER INFORMATION: IsomiR sequence
```

```
<400> SEQUENCE: 274 uucaacggguauuuauugagc                                              21

<210> SEQ ID NO 275
<211> LENGTH: 20
<212> TYPE: RNA
<213> ORGANISM: Artificial sequence
<220> FEATURE:
<223> OTHER INFORMATION: IsomiR sequence

<400> SEQUENCE: 275 uucaacggguauuuauugag                                               20

<210> SEQ ID NO 276
<211> LENGTH: 25
<212> TYPE: RNA
<213> ORGANISM: Artificial sequence
<220> FEATURE:
<223> OTHER INFORMATION: IsomiR sequence

<400> SEQUENCE: 276 uuuggcaaugguagaacucacacug                                          25

<210> SEQ ID NO 277
<211> LENGTH: 23
<212> TYPE: RNA
<213> ORGANISM: Artificial sequence
<220> FEATURE:
<223> OTHER INFORMATION: IsomiR sequence

<400> SEQUENCE: 277 uuuggcaaugguagaacucacac                                            23

<210> SEQ ID NO 278
<211> LENGTH: 26
<212> TYPE: RNA
<213> ORGANISM: Artificial sequence
<220> FEATURE:
<223> OTHER INFORMATION: IsomiR sequence

<400> SEQUENCE: 278 uuuggcaaugguagaacucacacugg                                         26

<210> SEQ ID NO 279
<211> LENGTH: 22
<212> TYPE: RNA
<213> ORGANISM: Artificial sequence
<220> FEATURE:
<223> OTHER INFORMATION: IsomiR sequence

<400> SEQUENCE: 279 uuuggcaaugguagaacucaca                                             22

<210> SEQ ID NO 280
<211> LENGTH: 19
<212> TYPE: RNA
<213> ORGANISM: Artificial sequence
<220> FEATURE:
<223> OTHER INFORMATION: IsomiR sequence

<400> SEQUENCE: 280 uuuggcaaugguagaacuc                                                19

<210> SEQ ID NO 281
<211> LENGTH: 20
```

```
<212> TYPE: RNA
<213> ORGANISM: Artificial sequence
<220> FEATURE:
<223> OTHER INFORMATION: IsomiR sequence

<400> SEQUENCE: 281
uuuggcaaug guagaacuca                                           20

<210> SEQ ID NO 282
<211> LENGTH: 21
<212> TYPE: RNA
<213> ORGANISM: Artificial sequence
<220> FEATURE:
<223> OTHER INFORMATION: IsomiR sequence

<400> SEQUENCE: 282
uuuggcaaug guagaacuca c                                         21

<210> SEQ ID NO 283
<211> LENGTH: 20
<212> TYPE: RNA
<213> ORGANISM: Artificial sequence
<220> FEATURE:
<223> OTHER INFORMATION: IsomiR sequence

<400> SEQUENCE: 283
aacuggccua caaaguccca                                           20

<210> SEQ ID NO 284
<211> LENGTH: 21
<212> TYPE: RNA
<213> ORGANISM: Artificial sequence
<220> FEATURE:
<223> OTHER INFORMATION: IsomiR sequence

<400> SEQUENCE: 284
aacuggccua caaaguccca g                                         21

<210> SEQ ID NO 285
<211> LENGTH: 22
<212> TYPE: RNA
<213> ORGANISM: Artificial sequence
<220> FEATURE:
<223> OTHER INFORMATION: IsomiR sequence

<400> SEQUENCE: 285
ugagcuaaau gugugcuggg ac                                        22

<210> SEQ ID NO 286
<211> LENGTH: 24
<212> TYPE: RNA
<213> ORGANISM: Artificial sequence
<220> FEATURE:
<223> OTHER INFORMATION: IsomiR sequence

<400> SEQUENCE: 286
ugagcuaaau gugugcuggg acac                                      24

<210> SEQ ID NO 287
<211> LENGTH: 22
<212> TYPE: RNA
<213> ORGANISM: Artificial sequence
<220> FEATURE:
<223> OTHER INFORMATION: IsomiR sequence

<400> SEQUENCE: 287
```
agcuaaaugu gugcugggac ac                                                    22

<210> SEQ ID NO 288
<211> LENGTH: 21
<212> TYPE: RNA
<213> ORGANISM: Artificial sequence
<220> FEATURE:
<223> OTHER INFORMATION: IsomiR sequence

<400> SEQUENCE: 288
gagcuaaaug ugugcuggga c                                                     21

<210> SEQ ID NO 289
<211> LENGTH: 21
<212> TYPE: RNA
<213> ORGANISM: Artificial sequence
<220> FEATURE:
<223> OTHER INFORMATION: IsomiR sequence

<400> SEQUENCE: 289
aggugagcua aaugugugcu g                                                     21

<210> SEQ ID NO 290
<211> LENGTH: 21
<212> TYPE: RNA
<213> ORGANISM: Artificial sequence
<220> FEATURE:
<223> OTHER INFORMATION: IsomiR sequence

<400> SEQUENCE: 290
agcuaaaugu gugcugggac a                                                     21

<210> SEQ ID NO 291
<211> LENGTH: 26
<212> TYPE: RNA
<213> ORGANISM: Artificial sequence
<220> FEATURE:
<223> OTHER INFORMATION: IsomiR sequence

<400> SEQUENCE: 291
ugagcuaaau gugugcuggg acacau                                                26

<210> SEQ ID NO 292
<211> LENGTH: 19
<212> TYPE: RNA
<213> ORGANISM: Artificial sequence
<220> FEATURE:
<223> OTHER INFORMATION: IsomiR sequence

<400> SEQUENCE: 292
gagcuaaaug ugugcuggg                                                        19

<210> SEQ ID NO 293
<211> LENGTH: 23
<212> TYPE: RNA
<213> ORGANISM: Artificial sequence
<220> FEATURE:
<223> OTHER INFORMATION: IsomiR sequence

<400> SEQUENCE: 293
ugagcuaaau gugugcuggg aca                                                   23

<210> SEQ ID NO 294
<211> LENGTH: 25
<212> TYPE: RNA
<213> ORGANISM: Artificial sequence

```
<220> FEATURE:
<223> OTHER INFORMATION: IsomiR sequence

<400> SEQUENCE: 294
ugagcuaaau gugugcuggg acaca                                          25

<210> SEQ ID NO 295
<211> LENGTH: 23
<212> TYPE: RNA
<213> ORGANISM: Artificial sequence
<220> FEATURE:
<223> OTHER INFORMATION: Antagomir sequence

<400> SEQUENCE: 295
gaaacccagc agacaaugua gcu                                            23

<210> SEQ ID NO 296
<211> LENGTH: 24
<212> TYPE: RNA
<213> ORGANISM: Artificial sequence
<220> FEATURE:
<223> OTHER INFORMATION: Antagomir sequence

<400> SEQUENCE: 296
gagacccagu agccagaugu agcu                                           24
```